US006635750B1

(12) United States Patent
Coyle et al.

(10) Patent No.: US 6,635,750 B1
(45) Date of Patent: Oct. 21, 2003

(54) B7-H2 NUCLEIC ACIDS, MEMBERS OF THE B7 FAMILY

(75) Inventors: Anthony J. Coyle, Boston, MA (US); Christopher C. Fraser, Lexington, MA (US); Stephen Manning, Arlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/620,461

(22) Filed: Jul. 20, 2000

(51) Int. Cl.[7] .......................... C07H 21/04; C12N 15/09; C12N 15/12; C12N 15/63; C12N 15/85
(52) U.S. Cl. .................... 536/23.5; 536/23.1; 536/23.4; 435/69.1; 435/69.7; 435/455; 435/471; 435/252.3; 435/320.1; 435/810
(58) Field of Search ............................... 435/69.1, 69.7, 435/455, 471, 252.3, 320.1, 810; 536/23.1, 23.4, 23.5

(56) References Cited

U.S. PATENT DOCUMENTS

| | | |
|---|---|---|
| 5,521,288 A | 5/1996 | Linsley et al. |
| 5,861,310 A | 1/1999 | Freeman et al. |
| 5,942,607 A | 8/1999 | Freeman et al. |
| 5,968,510 A | 10/1999 | Linsley et al. |
| 2002/0095024 A1 * | 7/2002 | Mikesell et al. |
| 2002/0164600 A1 * | 11/2002 | Freeman et al. |

FOREIGN PATENT DOCUMENTS

| | | |
|---|---|---|
| EP | 1074617 A | 2/2001 |
| WO | WO 95/03408 A | 2/1995 |
| WO | WO 95/05464 A | 2/1995 |
| WO | WO 96/40915 | 12/1996 |
| WO | WO 97/24447 A | 7/1997 |
| WO | WO 00/37643 A | 6/2000 |
| WO | WO 00/55375 A | 9/2000 |
| WO | WO 00/61612 A | 10/2000 |
| WO | WO 01/34629 A | 5/2001 |
| WO | WO 01/49716 A | 7/2001 |
| WO | WO 01/83750 A | 11/2001 |
| WO | WO 01/94413 A | 12/2001 |

OTHER PUBLICATIONS

Peach et al. J. Biol. Chem. 1995; 270:21181–21187.*
Metzler et al. Nature Structural Biol. 1997; 4:527–531.*
Coyle et al. Nature Immunol. 2:203–209 2001.*
Skolnick et al. Trends in Biotech. 18:34–39 2000.*
Voet et al. In Biochemistry. John Wiley& Sons. 1990. Vol 1, pp. 126–128 and 230.*
Inobe, M. et al., J. of Immunology 157:582–588 (1996).
Database EMBL Sequence Database [Online] Hinxton, UK; Jun. 1, 1999 S. Y. Tseng et al.: "Mus Musculus Butyrophilin–like (Btdc) mRNA, Complete cds." EMBL Sequence Accession No. AF142780.
Database EMBL Sequence Database [Online]Hinxton, UK; Feb. 22, 2000 T. Isogai and T. Otsuki: Homo Sapiens cDNA FLJ11010 fis, clone PLACE1003145; XP002193892. EMBL Sequence Accession No. AK001872.
Yoshinaga, S.K. et al., "T–cell co–stimulation through B7RP–1 and ICOS", Nature, MacMillan Journals Ltd., London, GB, vol. 402, Dec. 16, 1999, 827–832.
Gerstmayer, Bernhard et al., "Costimulation of T–Cell Proliferation by a Chimeric B7–Antibody Fusion Protein", Cancer Immunology Immunotherapy, vol. 45, No. 3–4, Nov. 1997, 156–158.
Abbas et al., "T–Cell Stimulation: an Abundance of B7s, "Nature Medicine, Dec. 1999, pp. 1345–1346, vol. 5, No. 12.
Dong et al., "B7–H1, a Third Member of the B7 Family, Co–stimultes T–cell Proliferation and Interleukin–10 Secretion," Nature Medicine, Dec. 1999, pp. 1365–1369, vol. 5, No. 12.
Fargeas et al., "Identification of Residues in the V Domain of CD80 (B7–1) Implicated in Functional Interactions with CD28 and CTLA4,"J. Exp. Med., Sep. 1995, pp. 667–675, vol. 182.
Freeman et al., abstract, "The B7–Homologue, PD–I, is the Ligand of the PD–1 Immunoinhibitory Receptor," The FASEB Journal, Apr. 20, 2000, Abstract No. 153.34, p. A1170, vol. 14, No. 6.
Hutloff et al., "ICOS is an Inducible T–Cell Co–Stimulator Structurally and Functionally Related to CD28," Nature, Jan. 21, 1999, pp. 263–266, vol. 397.
Ling et al., "Cutting Edge: Identification of GL50, a Novel B7–Like Protein that Functionally Binds to ICOS Receptor," J. Immunol., Feb. 15, 2000, pp. 1653–1657, vol. 164, No. 4.
Mages et al., "Molecular Cloning and Characterization of Murine ICOS and Identification of B7h as ICOS Ligand," Eur. J. Immunol., Apr. 2000, pp. 1040–1047, vol. 30, No. 4.
Peach et al., "Both Extracellular Immunoglobin–like Domains of CD80 Contain Residues Critical for Binding T Cell Surface Receptors CTLA–4 and CD28," Journal of Biological Chemistry, Sep. 8, 1995, pp. 21181–21187, vol. 270, No. 36.
Yoshinaga et al., "T–Cell Co–Stimulation through B7RP–1 and ICOS," Nature, Dec. 16, 1999, pp. 827–832, vol. 402, No. 6763.

* cited by examiner

Primary Examiner—Phillip Gambel
Assistant Examiner—Jessica H. Roark
(74) Attorney, Agent, or Firm—Millennium Pharmaceuticals, Inc.

(57) ABSTRACT

B7-like polypeptides, proteins, and nucleic acid molecules are disclosed. In addition to isolated, full-length B7-like proteins, the invention further provides isolated B7-like fusion proteins, antigenic peptides, and anti-B7-like antibodies. The invention also provides B7-like nucleic acid molecules, recombinant expression vectors containing a nucleic acid molecule of the invention, host cells into which the expression vectors have been introduced, and nonhuman transgenic animals in which a B7-like gene has been introduced or disrupted. Diagnostic, screening, and therapeutic methods utilizing compositions of the invention are also provided.

47 Claims, 40 Drawing Sheets

```
hB7-1              ----------------SWAITLISVNGIFVICCLTYCFAPRCRER----RRNERL------  280
hB7-2              ----------------PWITAVLP----TVIICVMVFCLILWKKK----KKRPRNSY-----  274
hB7RP-1            -----------------------------------------------------IGERDK   241
hB7RP-2            ------------------------------------------------------------  236
hB7-H1             ------------------------------------------------------------  250
hB7-H2 long        -----------------LVI----LGAILL--C---------------------------  230
hB7-H2 short       -----------------PTW----LLHIFIPSC---------------------------  140
hBIN prot          SK----ERLLEELKWKKAT-----------------------------------------  299
hBIN2A1 prot       VK----EKLQEELRWRRTF-----------------------------------------  324
hBIN2A2 prot       ------QQLQEELRWRRTF-----------------------------------------  323
hBIN3A2 prot       ------------------------------------------------------------  318
hBI2.1 prot        RKKSS-----EKLQEELRWRRTF-------------------------------------  310
hBI3.2 prot        VK----------------------------------------------------------  326
hBI3.3 prot        RKKIQYLTRGEES-----------------------------------------------  388
hBIN3A3 prot (hB73) WRKIQYMARGEESSSDTKKSALMLKWKKALFKPGDKMLQMRVSPCKINWMYSKIYCRKGELIKFISGRVK  344
hBIN3A1 prot       WRKIQYMARGEKSLAYHE--KMALFKPADVIL----------------------------  344
hBIF5 prot         WRSIQYASRGERHSAYNE--KKALFKPGEEML----------------------------  344
hB7.3              WRSIQYASRGERHSAYNE--KKALFKPADVIL----------------------------  290
```

FIG. 1B-3.

Alignment Report of hB7lineup, using Clustal method with PAM250 residue weight table.

```
hB7-1          -------------------------------------------------------------TMERE---  280
hB7-2          ------------------------------KCGTN----------------------------------  284
hB7RP-1        ITENPVSTGEK-NAATWSI--------------------------------------------------  262
hB7RP-2        ITGQPMTFPPE---ALWVT--------------------------------------------------  256
hB7-H1         ----LGV-----------------------------------------------------LAV------  260
hB7-H2 long    ----I-I-----------------------------------------ALTFI---FR--VGLS-----  242
hB7-H2 short   ----I-I-----------------------------------------AFIFIATVIA----------  152
hBIN prot      ------------------------------------------------AFIFIATVIA----------  299
hBIN2A1 prot   ---------------------------------------------------------------------  324
hBIN2A2 prot   ---------------------------------------------------------------------  323
hBIN3A2 prot   ---------------------------------------------------------------------  318
hBT2.1 prot    ---------------------------------------------------------------------  310
hBT3.2 prot    -----------------------S---------------------DT----------------------  330
hBT3.3 prot    IENKPLSIKHQWAXSMWGGKQQKCXKRILVASWGRIRVLGKAXIDLTFISPLVTRPLGLSPMTLMRESHS  458
hBIN3A3 prot (hB73) ----------------------D-------P--------DT----------------------  348
hBIN3A1 prot   ----------------------Q-------P--------------------------------------  345
hBTF5 prot     ----------------------D-------P-----KT-------------------------------  348
hB7.3          ---------------------------------------------------------------------  290
```

FIG. 1C-1.

```
hB7-1                                                                                            -RRESVR       286
hB7-2                                                                             -----ESEQTKKREKIH            296
hB7RP-1                                                                           ----------------             262
hB7RP-2                                                                           ----------------             256
hB7-H1                                                                            ----------------             264
hB7-H2 long                                        ----LRKG---                    ----------------             247
hB7-H2 short                                       ----LRKQL--                    ----------------             157
hBIN prot                                          ----LRKQL--                    ----------------             331
hBIN2A1 prot                                              ---LHAVDVTLDPDTAHPHLFLFLYEDSKSVRLEDSR                 356
hBIN2A2 prot                                              ---LHAVDVVLDPDTAHPDLFLSEDRRSVRRCPFR                   355
hBIN2A3 prot                                              ---LHAADVVLDPDTAHPELFLSEDRRSVRRGPYR                   318
hBT2.1 prot                                               ---LHAVDVVLDPDTAHPDLFLSEDRRSVRRCPFR                   342
hBT3.2 prot                                                       --NKSALMLK---                                338
hBT3.3 prot    GQARDTGFWKDLLSMAQALHAVALKSRKNGRPHGHLLKLSAADVILYPDMANAILLVSEDQRSVQRAEEP                           528
hBIN3A3 prot (hB73)                                       -----ANAILLVSEDQRSVQRAEEP                             368
hBIN3A1 prot                                                                                                    345
hBTF5 prot                                                ------ANPILLVSEDQRSVQRAKEP                            368
hB7.3                                                                                                           290
```

Alignment Report of hB7lineup, using Clostal method with PAM250 residue weight table.

```
hB7-1                                                                                                              --PV,                       289
hB7-2                                                         -EAQRVFKSSKTSSCDKSDTCF                                                           323
hB7RP-1                                                                                                                                        298
hB7RP-2                                                                                                                                        291
hB7-H1              PETEL                                                                                                                      289
hB7-H2 long         DQDGE                                                                                                                      274
hB7-H2 short        ---CGIQDTNSKKQSDTHEE                                                                                                       182
hBIN prot           ---DTTKRPVTTTKREVNSAI,                                                                                                     466
hBIN2A1 prot        ---DTTKRPVTTTKREVNSA-                                                                                                      485
hBIN2A2 prot        LYGNG-YWALTPLRTPPAGPPRRVGIFLDYESGDISFYNMDGSDIYTFSNVTFSGPLRPFFCLWSSG                                                         481
hBIN3A1 prot        MHKEQ-YRAVSSPDRIPPKESLCRVGVFLDYEAGDVSFYNMRDRSHIYTCPRSAFSVPVR---                                                             318
hBIN3A2 prot        MFGNQ-YRALSSPERIPPKESLCRVGVFLDYEAGDVSFYNMRDRSHIYTCPRSAFTVPVR---                                                             477
hBT2.1 prot         MHKEQ-YRAVSSPDRIPPKESLCRVGVFLDYEAGDVSFYNMRDRSHIYTCPRSAFSGPDTS---QSGDP                                                       343
hBT3.2 prot         LTDNKYRALTEPRTNKPEPPRKVGVILDYETGHISFYNATDGSHIYTFLHASSSEPLYPVFRILTLE                                                         665
hBT3.3 prot         LTDNKYRALTEPRTNKPEPPRKVGIFLDYETGEISFYNATDGSHIYTFPHASFSEPLYPVFRILTLE                                                         505
hBIN3A3 prot (hB73) --MRH------FVK,                                                                                                            353
hBIF5 prot          LTDNKYRTLTEPRTNKPKPPKKVGVFLDYETGDISFYNAVDGSHIHTFLDVSFSEALYPVFRILTLE                                                         504
hB7.3                                                                                                                                          290
```

FIG. 1D-1.

```
                                                                                    289
                                                                                    323
                                                                                    306
                                                                                    312
                                                                                    289
                                                                                    274
                                                                                    182
                                                                                    527
                                                                                    528
                                                                                    524
                                                                                    318
                                                                                    530
                                                                                    350
                                                                                    734
                                                                                    575
                                                                                    353
                                                                                    514
                                                                                    290 hB7-1            ------------------------------------------------------------------
hB7-2            ------------------------------------------------------------------
hB7RP-1          ------------------------------------------------------------------
hB7RP-2          ------------------------------------------------------------------
hB7H1            ------------------------------------------------------------------
hB7-H2 long      --------------TESWNLL---------------------------------------------
hB7-H2 short     --------------GEGSKTALQDLKHSDSKEDDG-------------------------------
hB1N prot        KKPLTICIADGPERVTVIANAQDLSKEIPLSDMGEESAPRDADTLHSKLIPTQPSQGAP.
hB1N2A1 prot     ----DFFRLGCEDSPIFICPALTG--ANGVT---VPEEGLTLH-RVG----THQSL.
hB1N2A2 prot     ----DFFRLGSDDSPIFICPALTG--ASGVM---VPEEGLKLH-RVG----THQSL.
hB1N3A2 prot     ------------------------------------------------------------------
hB1N3A1 prot     PEPIESIRWSHSHVDKPWSFQQPPHNTHLPAASF----TPTTDLSPSFLLL----TRLCF.
hBT2.1 prot      ---------------------------------LKPG-----------------EEM
hBT3.2 prot      PTALTVCRIPK-VESSPDPDLVPDHSLEIPLTRGLANESGEPQAEVTSLLLPAQPGAKGLTLHNSQSEP.
hBT3.3 prot      PTALTICRIPKEVESSPDPDLVPDHSLETPLTRGLANESGEPQAEVTSLLLPAHPGAEVSPSATTNQNHK
hB1N3A3 prot (hB73) ------------------------------------------------------------------
hB1T5 prot       PTALSICPA.
hB7.3            ------------------------------------------------------------------
```

```
hB7-1              -------LLS
hB7-2              ----QEIA
hB7RP-1            --------T
hB7RP-2
hB7-H1             --------I
hB7-H2 long
hB7-H2 short
hBIN prot
hBIN2A1 prot
hBIN2A2 prot
hBIN3A2 prot       --------T
hBT2.1 prot
hBT3.2 prot        LQMRLHLVK
hBT3.3 prot
hBIN3A3 prot (hB73) LQARTEALY
hBIN3A1 prot
hBTF5 prot         --------M
hB7.3
```

hB7-H1 orf vs hB7-H2 long orf

GAP of : hB7-H1 orf from: 1 to: 873 to: hB7-H2 long orf from: 1 to: 822

Percent Similarity: 58.312   Percent Indentity: 58.312

```
  1 ATGAGGATATTTGCTGTCTTTATATT...CATGACCTACTGGCATTTGCT  47
    | ||| ||     |  | || ||   | ||   |     || |     |
  1 ...ATGATCTTCCTCCTGCTAATGTTGAGCCTGGAATTGCAGCTTCACCA  47

48 GAACGC......ATTTACTGTCACGGTTCCCAAGGACCTATATGTGGTAG  91
    || ||      ||| || || || || || |||| || ||  |  |||
 48 GATAGCAGCTTTATTCACAGTGACAGTCCCTAAGGAACTGTACATAATAG  97

92 AGTATGGTAGCAATATGACAATTGAATGCAAATTCCCAGTAGAAAAACAA 141
    || |||| |||||| ||||    | ||||||| ||         | || ||
 98 AGCATGGCAGCAATGTGACCCTGGAATGCAACTTTGACACTGGAAGTCAT 147

142 TTAGACCTGGCTGCACTAATTGTCTATTGGGAAATGGAGGATAAGAACAT 191
    |  |||| |   ||| ||| || || | ||| ||| ||      ||| ||
148 GTGAACCTTGGAGCAATAACAGCCAGTTTGCAAAAGGTG.....GAAAAT 192

192 TATTCAATTTGTGCATGGAGAGGAAGACCTGAAGGTTCAGCATAGTAGCT 241
    || ||                              || ||
193 GATACA..........................TCCCCA.......C 205

242 ACAGACAGAGGGCCCGGCTGTTGAAGGACCAGCTCTCCCTGGGAAATGCT 291
    || |   | ||  |||    || || |||| |||||  |||| || || ||
206 ACCGTGAAAGAGCCACTTTGCTGGAGGAGCAGCTGCCCCTAGGGAAGGCC 255

292 GCACTTCAGATCACAGATGTGAAATTGCAGGATGCAGGGGTGTACCGCTG 341
    |  || ||  |  || || ||  || | |||    ||||| ||
256 TCGTTCCACATAGCTCAAGTCCAAGTGAGGGACGAAGGACAGTACCAATG 305

342 CATGATCAGCTATGGTGGTGCC...GACTACAAGCGAATTACTGTGAAAG 388
    ||| |||| ||||||  |||   ||||||||| |  ||| ||||||
306 CATAATCATCTATGGGGTCGCCTGGGACTACAAGTACCTGACTCTGAAAG 355
```

FIG. 3A.

```
389  TCAATGCCCCATACAACAAAATCAACCAAAGAATTTTGGTTGTGGATCCA 438
     ||||  ||  |  ||||    |||||  |||    |         |    ||  ||||
356  TCAAAGCTTCCTACAGGAAAATAAAC...ACTCACATCCTAAAGGTTCCA 402

439  GTCACCTCTGAACATGAACTGACATGTCAGGCTGAGGGCTACCCCAAGGC 488
     |  ||   |||      ||  ||  ||  ||  ||||||   || || ||    |||
403  GAAACAGATGAGGTAGAGCTCACCTGCCAGGCTACAGGTTATCCTCTGGC 452

489  CGAAGTCATCTGGACAAGCAGTGACCATCAAGTCCTGAGTGGTAAGACCA 538
     |||||     ||||  |||  |  ||  |  |        |||||           |||
453  AGAAGTATCCTGGCCAAAC.GTCAGCGT....TCCTG..........CCA 487

539  CCACCACCAATTCCAAGAGAGAGGAGAAGCTTTTCAATGTGACCAGCACA 588
     |||||  |  |  ||||  ||      ||   ||  |  |  |  ||  |||||
488  ACACCAGCCACTCCAGGACCCCTGAAGGCCTCTACCAGGTCACCAGTGTT 537

589  CTGAGAATCAACACAACAACTAATGAGATTTTCTACTGCACTTTTAGGAG 638
     |||  |   |  ||  || |   ||    |  |||   |||    ||   |||
538  CTGCGCCTAAAGCCACCCCCTGGCAGAAACTTCAGCTGTGTGTTCTGGA. 586

639  ATTAGATCCTGAGGAAAACCATACAGCTGAATTGGTCATCCCAGAACTAC 688
     ||    ||||||  ||    |  |||         ||||  ||    ||  ||
587  ATACTCACGTGAGGGAA..CTTAC......TTTGGCCAGCATTGACCT.T 627

689  CTCTGGCACATCCTCCAAATGAAAGGACTCACTTGG.TAATTCTGGGAGC 737
     |      |  ||  ||        |    |  ||       |  ||||||  |       |||
628  CAAAGTCAGATGGAACCCAGGACCCATCCAACTTGGCTGCTTCACATTTT 677

738  CATCTTATTATGCCTTGGTG.TAGCACTGACATTCATCTTCCGTTTAAGA 786
     ||||      |   |||  |       ||  ||  |    |||    |  |   ||    ||
678  CATCCCCTCCTGCATCATTGCTTTCATTTCAT..AGCCACAGTGATAGC 725

787  AAAGGGAGAATGATGGATGTGAAAAAATGTGGCATCCAAGATACAAACTC 836
     || ||   |     ||| ||||  |||        |  ||| | ||| |   |
726  CCTAAGA.AAACAACTCTGTCAAAAGCTGTATTCTTCAAAAGACACA.AC 773

837  AAAGAAGCAAAGTGATACACATTTGGAGGAGACGTAA...........  873
     |||  |||     ||  |   ||||        |  ||  ||  |
774  AAA.AAGACCTGTCA.CCACAACAAAGAGGGAAGTGAACAGTGCTATCTG 821
```

FIG. 3B.

hB7-H1 orf vs hB7-H2 short orf

GAP of : hB7-H1 orf from: 1 to: 873 to: hB7-H2 short orf from: 1 to: 552

Percent Similarity: 59.811   Percent Indentity: 59.811

```
  1 ATGAGGATATTTGCTGTCTTTATATT...CATGACCTACTGGCATTTGCT  47
    | ||| ||    | | || ||  | ||   |    || ||   |
  1 ...ATGATCTTCCTCCTGCTAATGTTGAGCCTGGAATTGCAGCTTCACCA  47

48 GAACGC......ATTTACTGTCACGGTTCCCAAGGACCTATATGTGGTAG  91
    || ||       ||| || || || || || ||||| || ||   | |||
 48 GATAGCAGCTTTATTCACAGTGACAGTCCCTAAGGAACTGTACATAATAG  97

92 AGTATGGTAGCAATATGACAATTGAATGCAAATTCCCAGTAGAAAAACAA 141
    || |||| ||||||  |||| |  ||||||||| ||       | || ||
 98 AGCATGGCAGCAATGTGACCCTGGAATGCAACTTTGACACTGGAAGTCAT 147

142 TTAGACCTGGCTGCACTAATTGTCTATTGGGAAATGGAGGATAAGAACAT 191
    |  |||| |   ||| ||| | |  || | |||  ||    ||| ||
148 GTGAACCTTGGAGCAATAACAGCCAGTTTGCAAAAGGTG.....GAAAAT 192

192 TATTCAATTTGTGCATGGAGAGGAAGACCTGAAGGTTCAGCATAGTAGCT 241
    || ||                              || ||
193 GATACA............................TCCCCA.......C  205

242 ACAGACAGAGGGCCCGGCTGTTGAAGGACCAGCTCTCCCTGGGAAATGCT 291
    || |  | || |||    || || |||| |||| |||| |||| || || ||
206 ACCGTGAAAGAGCCACTTTGCTGGAGGAGCAGCTGCCCCTAGGGAAGGCC 255

292 GCACTTCAGATCACAGATGTGAAATTGCAGGATGCAGGGGTGTACCGCTG 341
    |  | || | | || || || ||| | ||  ||||| ||
256 TCGTTCCACATACCTCAAGTCCAAGTGAGGGACGAAGGACAGTACCAATG 305

342 CATGATCAGCTATGGTGGTGCC...GACTACAAGCGAATTACTGTGAAAG 388
    ||| ||||  |||||| | |||   |||||||||| ||| ||||||
306 CATAATCATCTATGGGGTCGCCTGGGACTACAAGTACCTGACTCTGAAAG 355
```

FIG. 4A.

```
389  TC.AATGCCCCATACAACAAAATCAACCAAAGAATTTTGGTTGTGGA... 434
     || || |  || |||    | | |||   || || | |  | |
356  TCAAAGGTCAGATGGAAC.CCAGGACCCATCCAACTTGGCTGCTTCACAT 404

435  .TCCAGTCACCTCTGAACATGAACTGACATGT...CAGGCTGAGGGCTAC 480
     | ||  | |  ||| |     ||  ||| |     || |  || | ||
405  TTTCATCCCCTCCTGCATCATTGCTTTCATTTTCATAGCCACAGTGATAG 454

481  CCCAAGGCCGAAGTCATCTG.GACAAGCAGTGACCATC.AAGTCCTGAGT 528
     ||| | |   ||    ||||  | ||||| ||   || ||  | |  |
455  CCCTAAG.AAAACAACTCTGTCAAAAGCTGTATTCTTCAAAAGACACAAC 503

529  GGTAAGACCACCACCACCAATTCCAAGAGAGAGGAGAAGCTTTTCAATGT 578
     ||||| |   |||||   | ||||| || | ||| | | ||| | |||
504  AAAAAGAC..CTGTCACCACAACAAAGAGGGAAGTGAA.CAGTGCTATCT 550

579  GACCAGCACACTGAGAATCAACACAACAACTAATGAGATTTTCTACTGCA 628
     ||
551  GA................................................ 552
```

FIG. 4B.

hB7-H2 long vs hB7-H1

GAP of: hB7-H2 long aa from: 1 to: 273 to: hB7-H1 aa from: 1 to: 290
Percent Similarity: 46.792  Percent Indentity: 37.358

```
  1  MIFLLLMLSLELQLHQIAALFTVTVPKELYIIEHGSNVTLECNFDTGSHV   50
        :  . : :       :   ||||||| :|| ::|:||| .|:| | |     .
  1  ..MRIFAVFIFMTYWHLLNAFTVTVPKDLYVVEYGSNMTIECKFPVEKQL   48

51  NLGAITASLQKVENDT..............SPHRERATLLEEQLPLGKAS   86
      .| |:     :   : .              |  :|:|| ||.:|| ||| |·
 49  DLAALIVYWEMEDKNIIQFVHGEEDLKVQHSSYRQRARLLKDQLSLGNAA   98

87  FHIPQVQVRDEGQYQCIIIYGVAWDYKYLTLKVKASYRKINTHILKV.PE  135
         |  |···| | |·|·| || | ||| :|·|| | | ||| || | |
 99  LQITDVKLQDAGVYRCMISYGGA.DYKRITVKVNAPYNKINQRILVVDPV  147

136  TDEVELTCQATGYPLAEVSWPN.....VSVPANTSHSRTPEGLYQVTSVL  180
      | | |||||| ||| ||| |  ·      ·|      |··|:   ||:  ||| |
148  TSEHELTCQAEGYPKAEVIWTSSDHQVLSGKTTTTNSKREEKLFNVTSTL  197

181  RLKPPPGRNFSCVF.....WNTHVRELTLASIDLQSQMEPRTHPTWLLHI  225
      |:         | | |              | ||:  : |       ||| :|
198  RINTTTNEIFYCTFRRLDPEENHTAELVIPELPLAHPPNERTHLV.ILGA  246

226  FIPSCIIAFIFIATVIALRKQLCQKLYSSKDTTKRPVTTTKREVNSAI   273
       :        :| || .   |    .|          .|: | |
247  ILLCLGVALTFIFRLRKGRMMDVKKCGIQDTNSKKQSDTHLEET....  290
```

FIG. 5.

hB7-H2 short vs hB7-H1

GAP of : hB7-H2 short aa from: 1 to: 183 to: hB7-H1 aa from: 1 to: 290

Percent Similarity: 41.243   Percent Indentity: 28.249

```
  1   MIFLLLMLSLELQLHQIAALFTVTVPKELYIIEHGSNVTLECNFDTGSHV   50
        .  .  :      :     ||||||:||::|:|||.|:|||  |
  1   ..MRIFAVFIFMTYWHLLNAFTVTVPKDLYVVEYGSNMTIECKFPVEKQL   48

51   NLGAITASLQKVENDT..............SPHRERATLLEEQLPLGKAS   86
       .|  |:    :  :               | :|:||  ||.:||  ||  |.
 49   DLAALIVYWEMEDKNIIQFVHGEEDLKVQHSSYRQRARLLKDQLSLGNAA   98

87   FHIPQVQVRDEGQYQCIIIYGVAWDYKYLTLKVKGQMEPRTHPTWLLHIF  136
       |  |...|  |  |.|.|  ||  |   |||  :|.||     |      :  :
 99   LQITDVKLQDAGVYRCMISYGGA.DYKRITVKVNA...PYNKINQRILVV  144

137   IPSCIIAFIFIATVIALRKQLCQKLYSSKDTTKRPVTTTKREVNSAI...  183
       |   :         : |.    . .: ||   :
145   DPVTSEHELTCQAEGYPKAEVIWTSSDHQVLSGKTTTTNSKREEKLFNVT  194
                                           :
                                           :
                                           :
```

FIG. 6.

hB7-H2 long orf vs hB7-H2 short orf

GAP of: hB7-H2 long orf from: 1 to: 822 to: hB7-H2 short orf from: 1 to: 552

Percent Similarity: 100.000  Percent Indentity: 100.000

```
  1 ATGATCTTCCTCCTGCTAATGTTGAGCCTGGAATTGCAGCTTCACCAGAT  50
    ||||||||||||||||||||||||||||||||||||||||||||||||||
  1 ATGATCTTCCTCCTGCTAATGTTGAGCCTGGAATTGCAGCTTCACCAGAT  50

51 AGCAGCTTTATTCACAGTGACAGTCCCTAAGGAACTGTACATAATAGAGC 100
    ||||||||||||||||||||||||||||||||||||||||||||||||||
 51 AGCAGCTTTATTCACAGTGACAGTCCCTAAGGAACTGTACATAATAGAGC 100

101 ATGGCAGCAATGTGACCCTGGAATGCAACTTTGACACTGGAAGTCATGTG 150
    ||||||||||||||||||||||||||||||||||||||||||||||||||
101 ATGGCAGCAATGTGACCCTGGAATGCAACTTTGACACTGGAAGTCATGTG 150

151 AACCTTGGAGCAATAACAGCCAGTTTGCAAAAGGTGGAAAATGATACATC 200
    ||||||||||||||||||||||||||||||||||||||||||||||||||
151 AACCTTGGAGCAATAACAGCCAGTTTGCAAAAGGTGGAAAATGATACATC 200

201 CCCACACCGTGAAAGAGCCACTTTGCTGGAGGAGCAGCTGCCCCTAGGGA 250
    ||||||||||||||||||||||||||||||||||||||||||||||||||
201 CCCACACCGTGAAAGAGCCACTTTGCTGGAGGAGCAGCTGCCCCTAGGGA 250

251 AGGCCTCGTTCCACATACCTCAAGTCCAAGTGAGGGACGAAGGACAGTAC 300
    ||||||||||||||||||||||||||||||||||||||||||||||||||
251 AGGCCTCGTTCCACATACCTCAAGTCCAAGTGAGGGACGAAGGACAGTAC 300

301 CAATGCATAATCATCTATGGGGTCGCCTGGGACTACAAGTACCTGACTCT 350
    ||||||||||||||||||||||||||||||||||||||||||||||||||
301 CAATGCATAATCATCTATGGGGTCGCCTGGGACTACAAGTACCTGACTCT 350

351 GAAAGTCAAAGCTTCCTACAGGAAAATAAACACTCACATCCTAAAGGTTC 400
    ||||||||||
351 GAAAGTCAAAG.................................. 361
```

FIG. 7A.

```
601 GAACTTACTTTGGCCAGCATTGACCTTCAAAGTCAGATGGAACCCAGGAC 650
                                  ||||||||||||||||||
362 ............................GTCAGATGGAACCCAGGAC 380

651 CCATCCAACTTGGCTGCTTCACATTTTCATCCCCTCCTGCATCATTGCTT 700
    ||||||||||||||||||||||||||||||||||||||||||||||||||
381 CCATCCAACTTGGCTGCTTCACATTTTCATCCCCTCCTGCATCATTGCTT 430

701 TCATTTTCATAGCCACAGTGATAGCCCTAAGAAAACAACTCTGTCAAAAG 750
    ||||||||||||||||||||||||||||||||||||||||||||||||||
431 TCATTTTCATAGCCACAGTGATAGCCCTAAGAAAACAACTCTGTCAAAAG 480

751 CTGTATTCTTCAAAAGACACAACAAAAAGACCTGTCACCACAACAAAGAG 800
    ||||||||||||||||||||||||||||||||||||||||||||||||||
481 CTGTATTCTTCAAAAGACACAACAAAAAGACCTGTCACCACAACAAAGAG 530

801 GGAAGTGAACAGTGCTATCTGA 822
    ||||||||||||||||||||||
531 GGAAGTGAACAGTGCTATCTGA 552
```

FIG. 7B.

hB7-H2 long vs hB7-H2 short

GAP of: hB7-H2 long aa from: 1 to: 273 to: hB7-H2 short aa from: 1 to: 183
Percent Similarity: 74.444   Percent Indentity: 71.667

```
  1  MIFLLLMLSLELQLHQIAALFTVTVPKELYIIEHGSNVTLECNFDTGSHV   50
     ||||||||||||||||||||||||||||||||||||||||||||||||||
  1  MIFLLLMLSLELQLHQIAALFTVTVPKELYIIEHGSNVTLECNFDTGSHV   50

51  NLGAITASLQKVENDTSPHRERATLLEEQLPLGKASFHIPQVQVRDEGQY  100
     ||||||||||||||||||||||||||||||||||||||||||||||||||
 51  NLGAITASLQKVENDTSPHRERATLLEEQLPLGKASFHIPQVQVRDEGQY  100

101  QCIIIYGVAWDYKYLTLKVKASY..RKINTHILKV.PETDEVELTCQATG  147
     ||||||||||||||||||||   |  |:|:  . :        ||
101  QCIIIYGVAWDYKYLTLKVKGQMEPRTHPTWLLHIFIPSCIIAFIFIATV  150

148  YPLAEVSWPNVSVPANTSHSRTPEGLYQVTSVLRLKPPPGRNFSCVFWNT  197
      |.   .|.          :| | :
151  IALRKQLCQKLYSSKDTTKRPVTTTKREVNSAI.................  183
```

```
                                                                    286      289
                                                                    311      323
                                                                    306      309
                                                                    305      317
                                                                    278      290
                                                                    262      274
                                                                    172      183 hB7-1       TLISVNGIFVCCLTYCFAPRCRERRRNERL----------------RRESVR--------------
hB7-2       AVLP----TVIICVMVFCLILWKWKKKRPRNSYKCGTNTMEREESEQTKKREKIHIPERSDEAQRVFKSS
hB7RP-1     TGEKNAATWSILAV-LCLLV----VVAVAIGWVCRDRCLGHSYAGAWAVSPELTESWNLL--------
hB7RP-2     FPPE--ALWYTVGLSVCLIA----VALAFVCWRKIKQSCEEENAGAEDQDGEGEGSKTALQPLKHS--
hB7-H1      -ERTHLVIGAILLIFGVI-----LFR-RKG--RMMDVKKCGIQDTN-----
hB7-H2 long -PRTHPTWLHLIPSQI-I-----AFIATLIARKGICQKLYSSKDQKRPV----
hB7-H2 short -PRTHPTWLHLIPSCI-I-----AFIATVIARKQLCQKLYSSKDTKRPV---- hB7-1       -------PV.
hB7-2       KTSSCCLKSDTCF
hB7RP-1     -------LLS
hB7RP-2     DSKEDDGQEIA.
hB7-H1      SKKQSDTHLEET
hB7-H2 long TTKREVNSAI.
hB7-H2 short TTKREVNSA-I Decoration 'Decoration #1': Shade (with dots) residues that match the Consensus exactly.
```

FIG. 11B.

☐ =Signal Sequence

▬ = Extracellular Domain

▭ =Transmembrane region

■ =Intracellular Domain

Alignment by Clustal W
In Sequence Explorer

Regions based on published data (B7-1, 2, RPI)
And ORF analysis (B7RP-1, 2)

```
hB7RP-1   ....MRLGSP .......... GLLFLLFSS LRADTQEKEV RAMVGSDVEL
hB7RP-2   ..MLRRRGSP GMGVHVGAAL GALWFCLTGA LEVQVPEDPV VALVGTDATL
hB7-1     MGHTRRQGTS PSKCPYLN.. FFQLLVLAGL SHFCSGVIHV TKEVKEVATL
hB7-2     ....MGLS N........... ILFVMAFL LSGAAP.LKI QAYFNETADL hB7RP-1   SCACPEGSRF DLNDVYYWQ TSESKTVVTY HIPQNSSLEN VDSRYRNRAL
hB7RP-2   CCSFSPEPGF SLAQLNLIWQ LTDTKQLVHS FAEG,...QD QGSAYANRTA
hB7-1     SCGHN.VSVE ELAQTRIYWQ KE.,KKMVLT MMSGD..MN IWPEYKNRTI
hB7-2     PCGFANSQNQ SLSELVVFWQ DQE.NLVLNE VYLGKEKFDS VHSKYMGRTS hB7RP-1   MSPAGMLRGD FSLRLFNVTP QDEQKFHCLV LSQSLGFQE. VLSVEVTLHV
hB7RP-2   LFPDLLAQGN ASLRLQRVRV ADEGSFTCFV SIRDGF.... ..SAAVSLQV
hB7-1     FD....ITNN LSIVILALRP SDEGTYECVV LKYEKDAFKR EHLAEVTLSV
hB7-2     FD.....SDS WTLRLHNLQI KDKGLYQCII HHKKPTGMIR IHDMNSELSV hB7RP-1   AANFSVPVVS APHSPSQ... DELTFTCTSI NGYPRPNVYW I.NKTDNSLL
hB7RP-2   AAPYSKPSMT LEPNKDLRPG DTVTITCSSY RGYPEAEVFW Q.DGQGVPLT
hB7-1     KADFPTPSIS DFEIPTS... NIRRIICSTS GGFPEPHLSW LENGEELNAI
hB7-2     LANFSQPEIV PISNITEN.. VYINLTCSSI HGYPEPKKMS VLLRTKNSTI hB7RP-1   DQALQNDTVF LNMRGLYDVV SVLRIAR... TPSVNIGCCI ENVLLQQNLT
hB7RP-2   GNVTT..SQM ANEQGLFDVH SVLRVVL... GANGTYSCLV RNPVLQQ..
hB7-1     NTTVS....Q DPETELYAVS SKLDFNM... TTNHSFMCLI KYGHLRVN..
hB7-2     EYDGIMQKSQ DNVTELYDVS ISLSVSFPDV TSNMTIFCIL ETDKTRLLS hB7RP-1   VGSQTGNDIG ERDKITENPV STGEKNAATW SILAVLCLLV VWAVAIGWVC
hB7RP-2   DAHGS..... VTIIGQPM TFPP..EALV VTVGLSVCLI ALLVALAFVC
hB7-1     ..QTFN..... WNTTKQEH FPDN.LLPSW AITLISVNGI FVICCLTYCF
hB7-2     ..SPFS..... IELEDPQ PPPD..HIPW ITAVLPTVII CVMVFCLILW
```

FIG. 12A.

| | | |
|---|---|---|
| hB7RP-1 | RDRCLQHS.Y AGAWAVSPET ELTGHV.... | .... |
| hB7RP-2 | WRKIKQSCEE ENAGAEDQDG EGEGSKTALQ PLKHSDSKED | DGQEIA.... |
| hB7-1 | APRCRERRRN ERLRRESVRP V......... | .... |
| hB7-2 | KWKKKKRPRN SYKCGTNTME REESEQTKKR EKIHIPERSD | EAQRVFKSSK |

| |
|---|
| hB7RP-1 ........... |
| hB7RP-2 ........... |
| hB7-1 ........... |
| hB7-2 TSSCDKSDTC F |

```
hB7-H1    RRNER-------------RR-SVR--------------------------  286
hB7-H2    KKRPRNSYKCGTNTMEREESEQTKKKREKIHIPERSDEAQRVF-------- 316
hB7RP-1   VVAVAIGWVCRDRCLQHSYAGAWAVSPETELTRSWNLL------------- 306
hB7RP-2   LL-VALAFVCWRKIKQSCEENAGAEDQDGEGEGSKTALQPLKHSDSKED   310 hB7-H1    ----PV.           289
hB7-H2    KSDTCF            323
hB7RP-1   ---LLS            309
hB7RP-2   QGQEIA.           317
```

Decoration 'Decoration #1': Shade residues that match the Consensus exactly.

Gap of: hB7RP-2 aa from: 1 to: 316 to: hB7-1 aa from: 1 to: 288
Percent Similarity: 32.734  Percent Indentity: 24.820

```
  1 ..MLRRRGSPGMGVHVGAALGALWFCLTGALEVQVPEDPVVALVGTDATL  48
      ||·|·        |  ||             |  |   |||
  1   MGHTRRQGTSPSKCPYLNFFQLL..VLAGLSHFCSGVIHVTKEVKEVATL 48

49 CCSFSPEPGFSLAQLNLIWQLTDTKQLVHSFAEGQDQGSAYANRTALFPD  98
    |  ·    |||  :||   :|  ··    ·     |  |||
 49 SCGHNVSVE.ELAQTRIYWQ.KEKKMVLTMMSGDMNIWPEYKNRTIFD..  94

99 LLAQGNASLRLQRVRVADEGSFTCFV......SIRDFGSAAVSLQVAAPY 142
    | |: :  ·| ·|||·: ||       · :    ||·| || |:
 95 ..ITNNLSIVILALRPSDEGTYECVVLKYEKDAFKREHLAEVTLSVKADF 142

143 SKPSMTLEPNKDLRPGDTVTITCSSYRGYPEAEVFWQDGQGVPLTGNVTT 192
    ||··   ·::    ·   |||·  |:||  ·|:   |   |        ||
143 PTPSIS...DFEIPTSNIRRIICSTSGGFPEPHLSWLE.NGEELNAINTT 188

193 SQMANEQGLFDVHSVLRVVLGANGTYSCLVRNPVLQQDAHGSVTITGQPM 242
       |  |: | | |   : |  ·: ||:: |·  ·   ·       | |
189 VSQDPETELYAVSSKLDFNMTTNHSFMCLIKYGHLRVNQTFNWNTTKQE. 237

243 TFPPEAL..WVTVGLSVCLIALLVALAFVCWRKIKQSCEEENAGAEDQDG 290
    ||    |  |    :||   |  ·:   |:         ·::     |   |
238 HFPDNLLPSWAITLISVNGIFVICCLTYCFAPRCRERRRNERLRRESVRP 287

291 EGEGSKTALQPLKHSDSKEDDGQEIA 316

Gap of: hB7RP-2 aa from: 1 to: 316 to: hB7-2 aa from: 1 to: 323
Percent Similarity: 31.186  Percent Indentity: 21.695

```
  1  MLRRRGSPGMGVHVGAALGALWFCLTGALEVQVPEDPVVALVGTDATLCC   50
                  | : | :   |     |    : |       | | |
  1  ...............MGLSNILFVMAFLLSGAAPL.KIQAYFNETADLPC   34

51  SFSPEPGFSLAQLNLIWQLTDTKQLVHSFAEGQDQGSAYANRTALFPDLL  100
     |.      ||..|  . ||    :     |    :    :     | :.       :
 35  QFANSQNQSLSELVVFWQDQENLVLNEVYLGKEKFDSVHSK..YMGRTSF   82

101  AQGNASLRLQRVRVADEGSFTCFVSIRD......FGSAAVSLQVAAPYSK  144
      . |||    ..:   |.|  :  |    :                           | | |  :|.
 83  DSDSWTLRLHNLQIKDKGLYQCIIHHKKPTGMIRIHQMNSELSVLANFSQ  132

145  PSMTLEPNKDLRPGDTVTITCSSYRGYPEAE...VFWQDGQGVPLTGNVT  191
     |  .    |    .:       : :||||   ||||  .    |  .                    :
133  PEIV..PISNITENVYINLTCSSIHGYPEPKKMSVLLRTKNSTIEYDGIM  180

192  TSQMANEQGLFDVHSVLRVV...LGANGTYSCLVRNPVLQQDAHGSVTIT  238
      |     |:||    | |          . |  |  |:.        .    .
181  QKSQDNVTELYDVSISLSVSFPDVTSNMTIFCILETDKTRLLSSPFSIEL  230

239  GQPMTFPPEALWVTVGLSVCLIALLV.ALAFVCWRKIKQSCEEENAGAED  287
      |      |    |:|    |       :|     .:|    |      |:|   |.                     |
231  EDPQPPPDHIPWITAVLPTVIICVMVFCLILWKWKKKKRPRNSYKCGTNT  280

288  QDGEGEGSKTALQPLKHSDSKEDDGQEIA..............  316
      :  | |   .|    .      |       :  |:  |    :
281  MERE.ESEQTKKREKIHIPERSDEAQRVFKSSKTSSCDKSDTCF  323
```

Gap of: hB7RP-1 aa from: 1 to: 302 to: hB7-2 aa from: 1 to: 323

Percent Similarity: 31.250  Percent Indentity: 21.181

```
  1  MRLGSPGLLFLLFSSLRADTQEKEVRAMVGSDVELSCACPEGSRFDLNDV   50
      :|  :||·: · |  ·    ·:·|     :| |          |·:·
  1  ..MGLSNILFVM.AFLLSGAAPLKIQAYFNETADLPCQFANSQNQSLSEL   47

51  YVYWQTSESKTVVTYHIPQNSSLENVDSRYRNRALMSPAGMLRGDFSLRL  100
     |:||   |·    ::  ·   ·:| |:| |          ··|||
 48  VVFWQDQENLVLNEVYLGK.EKFDSVHSKYMGRTSFD.....SDSWTLRL   91

101  FNVTPQDEQKFHCLV.LSQSLGFQEVLSVEVTLHVAANFSVP.VVSAPHS  148
     |·  ·|·  : |::   · |  : · || |||| | :|   ·
 92  HNLQIKDKGLYQCIIHHKKPTGMIRIHQMNSELSVLANFSQPEIVPISNI  141

149  PSQDELTFTCTSINGYPRP.NVYWINKTDNSLLDQALQNDTVFLNMRGLY  197
      :  ||·||·||| |  ·  : :| || ::          |·  ||
142  TENVYINLTCSSIHGYPEPKKMSVLLRTKNSTIEYDGIMQKSQDNVTELY  191

198  DVVSVLRIARTPSVNIGCCIENVLLQQNLTVGSQTGNDIGERDKITENPV  247
     ||   |  |·  ||      | :|   ·|  ·  |   ·  ·:
192  DVSISLSVS.FPDVTSNMTIFCILETDKTRLLSSPFSIELEDPQPPPDHI  240

248  STGEKNAATWSILAVLCLLVVVAVAIGWVCRDRCLQHSYAGAWAVSPETE  297
     |    ::|··|   :    | :|       | · |
241  PWITAVLPT....VIICVMVFCLILWKWKKKKRPRNSYKCGTNTMEREES  286

298  LTGHV..........................  302

287  EQTKKREKIHIPERSDEAQRVFKSSKTSSCDKSDTCF  323
```

Gap of: hB7RP-1 aa from: 1 to: 302 to: hB7-1 aa from: 1 to: 288

Percent Similarity: 30.292   Percent Indentity: 24.088

```
  1 ............MRLGSPGLLFLLFSSLRADTQEKEVRAMVGSDVELSC  37
               . | .|    .  |   |    |||
  1 MGHTRRQGTSPSKCPYLNFFQLLVLAGLSHFCSGVIHVTKEVKEVATLSC  50

38 ACPEGSRFDLNDVYVYWQTSESKTVVTYHIPQNSSLENVDSRYRNRALMS  87
    | :|    :|||  | | |·|     |   |:   |:|| :
 51 G.HNVSVEELAQTRIYWQ.KEKKMVLT....MMSGDMNIWPEYKNRTIFD  94

88 PAGMLRGDFSLRLFNVTPQDEQKFHCLVLS.QSLGFQEVLSVEVTLHVAA 136
     . |:: ·| || : |·||  : |·     ||||  |
 95 ....ITNNLSIVILALRPSDEGTYECVVLKYEKDAFKREHLAEVTLSVKA 140

137 NFSVPVVSAPHSPSQDELTFTCTSINGYPRPNVYWINKTDNSLLDQALQN 186
    ·|  | :|   |..    |·· |:| |··|:  :|      |:
141 DFPTPSISDFEIPTSNIRRIICSTSGGFPEPHLSWL...ENGEELNAINT 187

187 DTVFLNMRGLYDVVSVLRIARTPSVNIGCCIENVLLQQNLTVGSQTGNDI 236
    || | |      |·  || |·  | ||    |
188 TVSQDPETELYAVSSKLDFNMTTNHSFMCLIKYGHLRVNQTFNWNTTKQE 237

237 GERDKITENPVSTGEKNAATWSILAVLCLLVVVAVAIGWVCRDRCLQHSY 286
    |: .  |  . |  :|| |    |· |·
238 HFPDNLLPSWAIT...LISVNGIFVICCLTYCFAPRCRERRRNERLRRES 284

287 AGAWAVSPETELTGHV 302

285 VRPV............ 288
```

Gap of: hB7RP-1 aa from: 1 to: 302 to: hB7RP-2 aa from: 1 to: 316
Percent Similarity: 35.842  Percent Indentity: 30.824

```
  1  ..............MRLGSPGLLFLLFSSLRADTQEKEVRAMVGSDVELSC  37
                    | | |  ·|     | | |:|| ·|   | |
  1  MLRRRGSPGMGVHVGAALGALWFCLTGALEVQVPEDPVVALVGTDATLCC  50

38  ACPEGSRFDLNDVYVYWQTSESKTVVTYHIPQNSSLENVDSRYRNRALMS  87
        | | · || ·:·| ·|     · :·  | | |  :
 51  SFSPEPGFSLAQLNLIWQLTDTKQLV....HSFAEGQDQGSAYANRTALF  96

88  PAGMLRGDFSLRLFNVTPQDEQKFHCLVLSQSLGFQEVLSVEVTLHVAAN 137
      | : ·|· ||||  |   || | | | · |    |  | ·| |||
 97  PDLLAQGNASLRLQRVRVADEGSFTCFVSIRDFG.....SAAVSLQVAAP 141

138  FSVPVVSAPHSPS...QDELTFTCTSINGYPRPNVYWINKTDNSLLDQAL 184
     :| |  ··  ·     | ·| ||·| |||     |:| ·       |
142  YSKPSMTLEPNKDLRPGDTVTITCSSYRGYPEAEVFWQDGQGVPLTGNVT 191

185  QNDTVFLNMRGLYDVVSVLRIARTPSVNIGCCIENVLLQQNLTVGSQTGN 234
      ·     | ·||:|| ||||:    ·    |:| ·|||·   || |
192  TSQ..MANEQGLFDVHSVLRVVLGANGTYSCLVRNPVLQQD.AHGSVT.. 236

235  DIGERDKITENPVSTGEKNAATWSILAVLCLLVVVAVAIGWVCRDRCLQH 284
     || |··   · ||   · |:·||: ·|| : |
237  .......ITGQPMTFPPE..ALWVTVGLSVCLIALLVALAFVCWRKIKQS 277

285  .SYAGAWAVSPETELTGHV................302
      | |  : | |
278  CEEENAGAEDQDGEGEGSKTALQPLKHSDSKEDDGQEIA 316
```

Gap of: hB7-1 aa from: 1 to: 288 to: hB7-2 aa from: 1 to: 323

Percent Similarity: 33.579 Percent Indentity: 22.878

```
  1  MGHTRRQGTSPSKCPYLNFFQLLVLAGLSHFCSGVIHVTKEVKEVATLSC   50
                 : | .       . : :      | | | |
  1  ...............MGLSNILFVMAFLLSGAAPLKIQAYFNETADLPC   34

51  GH.NVSVEELAQTRIYWQKEKKMVLTMM....SGDMNIWPEYKNRTIFDI   95
       | : |·: :: || :· :||  ·       ·: ·|  || ||
 35  QFANSQNQSLSELVVFWQDQENLVLNEVYLGKEKFDSVHSKYMGRTSFD.  83

96  TNNLSIVILALRPSDEGTYECVVLKYEKDAFKREHLAEVTLSVKADFPTP  145
     ...  ·: :  |·  |·| |:|:·    · | |    ||| |·|  |
 84  SDSWTLRLHNLQIKDKGLYQCIIHHKKPTGMIRIHQMNSELSVLANFSQP  133

146  SISDFEIPTSNIR.RIICSTSGGFPEPHLSWLENGEELNAIN....TTVS  190
      |   | |:  : ||·  |:|||   ·  ·· |            |
134  EIVPISNITENVYINLTCSSIHGYPEPKKMSVLLRTKNSTIEYDGIMQKS  183

191  QDPETELYAVSSKLDF...NMTTNHSFMCLIKYGHLR.VNQTFNWNTTKQ  236
     ||  |||| ||   |       ··|·| ·  |:::     | ··   |·
184  QDNVTELYDVSISLSVSFPDVTSNMTIFCILETDKTRLLSSPFSIELEDP  233

237  EHFPDNLLPSWAITLISVNGIFVICCLTYCFAPRCRERRRNERLRRESVR  286
      : ||.:    |:   :  :||:: · :||  ·           |
234  QPPPDHIPWITAVLPTVIICVMVFCLILWKWKKKKRPRNSYKCGTNTMER  283

287  PV............................... 288

284  EESEQTKKREKIHIPERSDEAQRVFKSSKTSSCDKSDTCF  323
```

FIG. 19.

mB7RP-2 Nucleotide sequence

```
ATGCTTCGAGGATGGGGTGGCCCCAGTGTGGGTGTGTGTGTGCGCACAGCGCTGGGGGT
GCTGTGCCTCTGCCTCACAGGAGCTGTGGAAGTCCAGGTCTCTGAAGACCCCGTGGTGG
CCCTGGTGGACACGGATGCCACCCTACGCTGCTCCTTTTCCCCAGAGCCTGGCTTCAGT
CTGGCACAGCTCAACCTCATCTGGCAGCTGACAGACACCAAACAGCTGGTGCACAGCTT
CACGGAGGGCCGGGACCAAGGCAGTGCCTACTCCAACCGCACAGCGCTCTTCCCTGACC
TGTTGGTGCAAGGCAATGCGTCCTTGAGGCTGCAGCGCGTCCGAGTAACCGACGAGGGC
AGCTACACCTGCTTTGTGAGCATTCAGGACTTTGACAGCGCTGCTGTTAGCCTGCAGGT
GGCCGCCCCCTACTCGAAGCCCAGCATGACCCTGGAGCCCAACAAGGACCTACGTCCAG
GGAACATGGTGACCATCACGTGCTCTAGCTACCAGGGCTATCCGGAGGCCGAGGTGTTC
TGGAAGGATGGACAGGGAGTGCCCTTGACTGGCAATGTGACATCCCAGATGGCCAACGA
GCGGGGCTTGTTCGATGTTCACAGCGTGCTGAGGGTGGTGCTGGGTGCTAACGGCACCT
ACAGCTGCCTGGTACGCAACCCGGTGTTGCAGCAAGATGCTCACGGCTCAGTCACCATC
ACAGGGCAGCCCCTGACATTCCCCCCTGAGGCTCTGTGGGTAACCGTGGGGCTCTCTGT
CTGTCTTGTGGTACTACTGGTGGCCCTGGCTTTCGTGTGCTGGAGAAAGATCAAGCAGA
GCTGCGAGGAGGAGAATGCAGGTGCCAAGGACCAGGATGGAGATGGAGAAGGATCCAAG
ACAGCTCTACGGCCTCTGAAACCCTCTGAAAACAAAGAAGATGACGGACAAGAAATTGC
TTGA
```

FIG. 20.

mB7RP-2 Protein sequence

```
MLRGWGGPSVGVCVRTALGVLCLCLTGAVEVQVSEDPVVALVDTDATLRCSFSPEPGFS
LAQLNLIWQLTDTKQLVHSFTEGRDQGSAYSNRTALFPDLLVQGNASLRLQRVRVTDEG
SYTCFVSIQDFDSAAVSLQVAAPYSKPSMTLEPNKDLRPGNMVTITCSSYQGYPEAEVF
WKDGQGVPLTGNVTSQMANERGLFDVHSVLRVVLGANGTYSCLVRNPVLQQDAHGSVTI
TGQPLTFPPEALWVTVGLSVCLVVLLVALAFVCWRKIKQSCEEENAGAKDQDGDGEGSK
TALRPLKPSENKEDDGQEIA.
```

Gap of: mB7RP-2 aa from: 1 to: 315 to: hB7RP-2 aa from: 1 to: 316

Percent Similarity: 89.841   Percent Indentity: 88.254

```
  1 MLRGWGGPSVGVCVRTALGVLCLCLTGAVEVQVSEDPVVALVDTDATLRC  50
    ||| || ·|| | ||| |  ||||| ||||  ||||||||  ||||| |
  1 MLRRRGSPGMGVHVGAALGALWFCLTGALEVQVPEDPVVALVGTDATLCC  50

51 SFSPEPGFSLAQLNLIWQLTDTKQLVHSFTEGRDQGSAYSNRTALFPDLL 100
    |||||||||||||||||||||||||||||| ||·|||||| ||||||||
 51 SFSPEPGFSLAQLNLIWQLTDTKQLVHSFAEGQDQGSAYANRTALFPDLL 100

101 VQGNASLRLQRVRVTDEGSYTCFVSIQDFDSAAVSLQVAAPYSKPSMTLE 150
    |||||||||||| |||:||||||·|| |||||||||||||||||||||
101 AQGNASLRLQRVRVADEGSFTCFVSIRDFGSAAVSLQVAAPYSKPSMTLE 150

151 PNKDLRPGNMVTITCSSYQGYPEAEVFWKDGQGVPLTGNV.TSQMANERG 199
    |||||||· ||||||||·||||||||·|||||||||||| ||||||·|
151 PNKDLRPGDTVTITCSSYRGYPEAEVFWQDGQGVPLTGNVTTSQMANEQG 200

200 LFDVHSVLRVVLGANGTYSCLVRNPVLQQDAHGSVTITGQPLTFPPEALW 249
    |||||||||||||||||||||||||||||||||||||||| ||||||||
201 LFDVHSVLRVVLGANGTYSCLVRNPVLQQDAHGSVTITGQPMTFPPEALW 250

250 VTVGLSVCLVVLLVALAFVCWRKIKQSCEEENAGAKDQDGDGEGSKTALR 299
    ||||||||· ||||||||||||||||||||||||·||||·||||||||·
251 VTVGLSVCLIALLVALAFVCWRKIKQSCEEENAGAEDQDGEGEGSKTALQ 300

300 PLKPSENKEDDGQEIA 315
    ||| | ·||||||||
301 PLKHSDSKEDDGQEIA 316
```

Gap of: mB7RP-1 aa from: 1 to: 322 to: mB7RP-2 aa from: 1 to: 315

Percent Similarity: 32.192  Percent Indentity: 27.740

```
  1  MQLKCPCFVSLGTRQPVWKKLHVSSGFFSGLGLFLLLLSSLCAAS.AETE   49
        |      |   .||. | |.              .|
  1  ............MLRGWGGPSVGVCVRTALGVLCLCLTGAVEVQVSEDP   37

50  VGAMVGSNVVLSCIDPHRRHFNLSGLYVYWQIENPEVSVTYYLPYKSPGI   99
     | |:| ..  | |       |.|. | .||:..  | :  : |
 38  VVALVDTDATLRCSFSPEPGFSLAQLNLIWQLTDTKQLVHSFTEGRDQG.   86

100  NVDSSYKNRGHLSLDSMKQGNFSLYLKNVTPQDTQEFTCRVFMNTATELV  149
     |·| ||   |  | : ||| || |·|    |   :|| |           :
 87  ...SAYSNRTALFPDLLVQGNASLRLQRVRVTDEGSYTCFV......SIQ  127

150  KILEEVVRLRVAANFSTPVISTSDSSN..PGQERTYTCMSKNGYPEPNLY  197
     | |·||| :| |  ..  || | || | ||||  ·:
128  DFDSAAVSLQVAAPYSKPSMTLEPNKDLRPGNMVTITCSSYQGYPEAEVF  177

198  WINTTDNSLIDTALQNNTVYLNKLGLYDVISTLRLPWTSRGDVLCCVENV  247
     |   |   :     ·  |· ||:|| | ||·   ·|   |||
178  W...KDGQGVPLTGNVTSQMANERGLFDVHSVLRVVLGANGTYSCLVRNP  224

248  ALHQNITSISQAESFTGNNTKNPQETHNNELKVLVPVLAVLAAAAFVSFI  297
     | |·       ·· ||    | |    ·· |  ··  | | ||| ·
225  VLQQDAHG...SVTITGQPLTFPPEALWVTVGLSVCLVVLLVALAFVCWR  271

298  IYRRTRPHRSYTGPKTVQLELTDHA.................          322
     :··   ·  | |    :
272  KIKQSCEEEN.AGAKDQDGDGEGSKTALRPLKPSENKEDDGQEIA       315
```

FIG. 23.

B7-H2 NUCLEIC ACIDS, MEMBERS OF THE B7 FAMILY

FIELD OF THE INVENTION

The invention relates to the field of immunology and the development of adaptive immunity. More specifically the invention involves B7-related co-stimulatory molecules that are involved in the T lymphocyte response.

BACKGROUND OF THE INVENTION

Induction of a T lymphocyte response is a critical initial step in a host's immune response. Activation of T cells results in cytokine production by T cells, T cell proliferation, and generation of T-cell-mediated effector functions.

The cytokines are a diverse group of structurally dissimilar and genetically unrelated molecules. Cytokines serve as crucial intercellular-signaling molecules that are responsible for the multidirectional communication among immune and inflammatory cells engaged in host defense, repair, and restoration of homeostasis, as well as among other somatic cells in the connective tissues, skin, nervous system, and other organs. More particularly, this diverse group of intercellular-signaling proteins regulates local and systemic immune and inflammatory responses as well as wound healing, hematopoiesis, and many other biological processes.

Each cytokine is secreted by particular cell types in response to a variety of stimuli and produces a characteristic constellation of effects on the growth, motility, differentiation, or function of its target cells. In fact, cytokines regulate one another's production and activities. Other types of biological mediators, such as corticosteroids and prostaglandins, have agonistic or antagonistic effects on cytokine activities.

Interleukin-2 (IL-2) is an autocrine and paracrine growth factor that is secreted by activated T lymphocytes. IL-2 is a critical immunoregulatory cytokine as it is essential for clonal T-cell proliferation, is involved in cytokine production, and influences the functional properties of B cells, macrophages, and NK cells. IL-2 enhances proliferation and antibody secretion by normal B cells. However, the concentration required for the B-cell response is two- to three-fold higher than is required to obtain T-cell responses. Higher concentrations of IL-2 can also activate neutrophils. IL-2 exhibits a short half-life in the circulation. Thus, it generally acts only on the cell that secreted it or on cells in the immediate vicinity.

The IL-2 receptor is not expressed in resting T cells but is induced to maximal levels within two or three days after the cells become activated. A decline in receptor expression occurs up to 6–10 days after activation. This transient nature of IL-2 receptor expression maintains the cyclical, self-limiting pattern of normal T-cell growth in vivo.

During the course of an immune response, T cells differentiate into Th phenotypes defined by their pattern of cytokine secretion and immunomodulatory properties (Abbas et al. (1996) *Nature* 383:787). Th cells are composed of at least two distinct subpopulations, termed Th1 and Th2 cell subpopulations (Mosmann et al. (1989) *Ann. Rev. Immunol.* 7:145; Del Prete et al. (1991) *J. Clin. Invest.* 88:346; Wiernenga et al. (1990) *J. Immunol.* 144:4651; Yamamura et al. (1991) *Science* 254:277; Robinson et al. (1993) *J. Allergy Clin. Immunol.* 92:313). Th1 and Th2 cells appear to function as part of the different effector functions of the immune system (Mosmann et al. (1989) *Ann. Rev. Immunol.* 7:145). Specifically, Th1 cells direct the development of cell-mediated immunity, triggering phagocyte-mediated host defenses, and are associated with delayed hypersensitivity. Accordingly, infections with intracellular microbes tend to induce Th1-type responses. Th2 cells drive humoral immune responses, which are associated with, for example, defenses against certain helminthic parasites, and are involved in antibody and allergic responses.

Th1 cells secrete interleukin-2 (IL-2), interferon-γ (IFN-γ), and tumor neucrosis factor-α (TNF-α). These cytokines enhance inflammatory cell-mediated responses and have a pathogenic role in the development of autoimmune disease. Th2 cells secrete interleukin-4 (IL-4), interleukin-5 (IL-5), interleukin-10 (IL-10), and interleukin-13 (IL-13). These cytokines suppress inflammatory responses while potentiating humoral immunity and control and reverse disease evolution (Scott et al. (1994) *Immunity* 1:73; Smith et al. (1998) *J. Immunol.* 160:4841; Abbas et al. (1996) *Nature* 383:787). The different type of cytokines released upon stimulation has been demonstrated to be central to disease evolution (Chu and Londei (1996) *J. Immunol.* 157:2685; Hsieh et al. (1993) *Science* 260:547).

T-cell activation requires two signals. The first is an antigen-specific signal, often called a primary activation signal, which results from stimulation of a T-cell receptor present on the surface of the T cell. This antigen-specific signal is usually in the form of an antigenic peptide bound either to a major histocompatibility complex (hereafter MHC) class I protein or an MHC class II protein present on the surface of an antigen presenting cell (hereafter APC). For a review see Germain (1986) *Nature* 322:687–691.

In addition to an antigen-specific primary activation signal, T cells also require a second, non-antigen specific signal, to induce T-cell proliferation and/or cytokine production. This phenomenon has been termed co-stimulation (Mueller et al. (1989) *Annu. Rev. Immunol.* 7:445–480). This "two signal" concept explains why adaptive immunity is elicited by microbes and not by self-antigens, which do not induce second signals.

Like the antigen-specific signal, the co-stimulatory signal is triggered by a molecule on the surface of the antigen presenting cell (APC). The B7 molecules are an emerging family of immunoglobulin co-stimulatory molecules, first identified on B lymphocytes (Linsley et al. (1990) *Proc. Natl. Acad. Sci.* 87:5031–5035). Both B7-1 (CD80) and B7-2 (CD86) bind to the T cell receptors CD28 and CTLA4, resulting in co-stimulation of the T cell (Peach et al. (1995) *J. Biol. Chem.* 270:21181–21187; Fargeas et al. (1995) *J. Exp. Med.* 182:667–675; Bajorath et al. (1994) *Protein Sci.* 3:2148–2150; U.S. Pat. No. 5,942,607; and PCT Application No. WO 96/40915). Depending upon which receptor is bound, the activated T-cell immune response is enhanced (CD28) or inhibited (CTLA4) in a negative feedback loop. Additional B7 homologs have been identified including B7-H1, and B7RP-1 and its mouse ortholog B7h (Swallow et al. (1999) *Immunity* 11:423–432; Dong et al. (1999) *Nature Med.* 5:1365–1369; Yoshinaga et al. (1999) *Nature* 402:827–832). Although both B7RP-1 and B7-H1 co-stimulate T-cell proliferation, neither of these molecules binds to either CD28 or CTLA4 (Abbas and Sharpe (1999) *Nature Med.* 5:1345–1346; Yoshinaga et al. (1999) *Nature* 402:827–832). Unlike B7-1 and B7-2, B7-H1 has little effect on IL-2 production, but considerably increases T-cell production of IL-10, a B-cell differentiation factor that inhibits macrophages and cell-mediated immunity.

Ligation of the CD28 family member ICOS (inducible co-stimulator) increases IL-10 production. B7RP-1 has been shown to bind to this receptor (Yoshinaga et al. (1999) *Nature* 402:827–832) while B7-H1 does not appear to bind to ICOS (Dong et al. (1999) *Nature Med.* 5:1365–1369), although this result is not definitive. Like CD28, ICOS enhances all basic T-cell responses to a foreign antigen, namely, proliferation, secretion of lymphokines, up-regulation of molecules that mediate cell—cell interaction, and effective help for antibody secretion by B-cell. Unlike the constitutively expressed CD28, ICOS has to be de novo induced on the T-cell surface, does not up-regulate the production of IL-2, but superinduces the synthesis of IL-10 (Hutloff et. al. (1999) *Nature* 397:263–266). The inducible expression of ICOS shortly after T-cell activation indicates that ICOS may be particularly important in providing co-stimulatory signals to activated T cells, in contrast to CD28, which is essential in the activation and differentiation of naïve T cells (McAdam et al. (1998) *Immunol. Rev.* 165:231–247). ICOS may down-regulate immune responses by stimulating development of regulatory T cells, which normally function to control the injurious side effects of cell-mediated immunity. As ICOS signaling induces IL-10, which can also down-regulate B7-1 and B7-2 expression (Ding et al. (1993) *J. Immunol.* 151:1224–1234), ICOS co-stimulation may indirectly reduce or inhibit B7 expression and thereby inhibit B7-mediated CD28 co-stimulation. Therefore, whereas B7-1 and B7-2 function in the initiation and development of immune responses, B7RP-1 and B7-H1 may function to return the immune system to its resting state.

Another receptor belonging to the immunoglobulin gene superfamily, designated PD-1, also appears to be involved in the negative regulation of certain immune responses. PD-1 knockout mice develop Lupus-like autoimmune diseases (Nishimura et al. (1999) *Immunity* 11:141–151). In addition, the identification of a novel member of the B7 family (PD-L) that binds to the PD-1 receptor but not CD28, CTLA4, or ICOS has been reported (Freeman et al. (2000) *FASEB J.* 14(6):Abstract 153.34).

The profile of the natural immune response, specifically cytokine production, may determine the phenotype of the subsequent immune response. Therefore, methods are needed to regulate an immune response. There is great interest in the possibility that in disease situations in which antigens are either unknown or difficult to manipulate, immune responses may be either enhanced or terminated by manipulating the co-stimulation signals such as those signals affected by the B7 family of proteins. For example, modulating the co-stimulation signals may promote tumor immunity and reduce graft rejection, autoimmune, inflammatory, and infectious diseases (Abbas and Sharpe (1999) *Nature Med.* 5:1345–1346; Schweiter and Sharpe (1998) *J. Immunol.* 161:2762–2771; Wallace et al. (1994) *Transplantation* 58:602; Sayegh (1995) *J. Exp. Med.* 181:1869; Lenschow et al. (1995) *J. Exp. Med.* 181:1145; Finck et al. (1994) *Science* 265:1225; Cross et al. (1995) *J. Clin. Invest.* 95:2783; Perrin et al. (1995) *J. Immunol.* 154:1481; Corry et al. (1994) *J. Immunol.* 153:4142; U.S. Pat. Nos. 5,968,510, 5,861,310, and 5,521,288; and PCT Application No. WO 90/05541 and European Patent No. EP445228B 1).

SUMMARY OF THE INVENTION

Isolated nucleic acid molecules, hB7-H2 long (hB7-H21) and hB7-H2 short (hB7-H2s), corresponding to B7-like nucleic acid sequences are provided. Additionally, amino acid sequences corresponding to the polynucleotides are encompassed. In particular, the present invention provides for isolated nucleic acid molecules comprising nucleotide sequences encoding the amino acid sequences shown in SEQ ID NO:2 and SEQ ID NO:4, the nucleotide sequence encoding the DNA sequence deposited in a bacterial host as ATCC Accession Number PTA-2084, or the nucleotide sequence encoding the DNA sequence deposited in a bacterial host as ATCC Accession Number PTA-2085. Further provided are B7-like polypeptides having amino acid sequences encoded by the nucleic acid molecules described herein.

The present invention also provides vectors and host cells for recombinant expression of the nucleic acid molecules described herein, as well as methods of making such vectors and host cells and for using them for production of the polypeptides or peptides of the invention by recombinant techniques.

Another aspect of this invention features isolated or recombinant B7-like proteins and polypeptides. Preferred B7-like proteins and polypeptides possess at least one biological activity possessed by naturally occurring B7-like proteins.

Variant nucleic acid molecules and polypeptides substantially homologous to the nucleotide and amino acid sequences set forth in the Sequence Listing are encompassed by the present invention. Additionally, fragments and substantially homologous fragments of the nucleotide and amino acid sequences are provided.

Antibodies and antibody fragments that selectively bind B7-like polypeptides and fragments are provided. Such antibodies are useful in detecting B7-like polypeptides as well as in regulating the T-cell immune response and cellular activity.

The B7-like molecules of the present invention are useful for modulating immune responses. The molecules of the invention are useful for the treatment and diagnosis of T-lymphocyte-related disorders, including, but not limited to, atopic conditions, such as asthma and allergy, including allergic rhinitis, psoriasis, the effects of pathogen infection, chronic inflammatory diseases, autoimmune diseases, graft rejection, graft versus host disease and neoplasia. Compositions of the invention are useful in the treatment and diagnosis of disorders related to bone-metabolism, and in the treatment and diagnosis of cancers such as B7 lymphomas, carcinomas, and T cell leukemias, and useful for treatment of viral diseases and cancers such as herpes, Kaposi's sarcoma, genital warts, hairy cell leukemia, melanoma, and renal cell carcinoma.

In addition, the molecules of the invention are useful as modulating agents in a variety of cellular processes including growth promoting activity, particularly the antigen-independent proliferation of T helper cell clones, and direct effects on normal hemopoietic progenitors, human T cells, B cells, thymocytes, thymic lymphomas, and neuronal cell lines.

This invention provides isolated nucleic acid molecules encoding B7-like proteins or biologically active portions thereof, as well as nucleic acid fragments suitable as primers or hybridization probes for the detection of B7-like-encoding nucleic acids.

In another aspect, the present invention provides a method for detecting the presence of B7-like activity or expression in a biological sample by contacting the biological sample with an agent capable of detecting an indicator of B7-like activity such that the presence of B7-like activity is detected in the biological sample.

In yet another aspect, the invention provides a method for modulating B7-like activity comprising contacting a cell with an agent that modulates (inhibits or stimulates) B7-like activity or expression such that B7-like activity or expression in the cell is modulated. In one embodiment, the agent is an antibody that specifically binds to a B7-like protein. In another embodiment, the agent modulates expression of B7-like proteins by modulating transcription of a B7-like gene, splicing of a B7-like mRNA, or translation of a B7-like mRNA. In yet another embodiment, the agent is a nucleic acid molecule having a nucleotide sequence that is antisense to the coding strand, or to a portion thereof, of the B7-like mRNA or the B7-like gene.

In another aspect, the invention provides a method for identifying a compound that binds to or modulates the activity of a B7-like protein and/or its binding partner. In general, such methods entail measuring a biological activity of a B7-like protein in the presence and absence of a test compound and identifying those compounds that alter the activity of the B7-like protein.

In one embodiment, the methods of the present invention are used to treat a subject having a disorder that involves B7-like protein activity or nucleic acid expression by administering an agent that is a B7-like modulator to the subject. In one embodiment, the B7-like modulator is a B7-like protein. In another embodiment, the B7-like modulator is a B7-like nucleic acid molecule. In other embodiments, the B7-like modulator is a peptide, peptidomimetic, or other small molecule. In another embodiment the B7-like modulator is an antibody specific for B7-like proteins.

The present invention also provides a diagnostic assay for identifying the presence or absence of a genetic lesion or mutation characterized by at least one of the following: (1) aberrant modification or mutation of a gene encoding a B7-like protein; (2) misregulation of a gene encoding a B7-like protein; and (3) aberrant post-translational modification of a B7-like protein, wherein a wild-type form of the gene encodes a protein with a B7-like activity.

The invention also features methods for identifying a compound that modulates the expression of B7-like genes by measuring the expression of the B7-like sequences in the presence and absence of the compound.

Other features and advantages of the invention will be apparent from the following detailed description and claims.

BRIEF DESCRIPTION OF THE DRAWINGS

FIG. 4 shows a GAP alignment of the open reading frame of hB7-H1 (SEQ ID NO:22) with the open reading frame of hB7-H2 short (SEQ ID NO:21). The sequences share approximately 59.8% identity over the open reading frame of hB7-H2 short.

FIG. 5 shows a GAP alignment of the amino acid sequence of hB7-H2 long (SEQ ID NO:2) with the amino acid sequence of hB7-H2 (SEQ ID NO:8). The sequences share approximately 37.4% identity over the 273 amino acid residues of hB7-H2 long.

FIG. 6 shows a GAP alignment of the amino acid sequence of hB7-H2 short (SEQ ID NO:4) with the amino acid sequence of hB7-H1 (SEQ ID NO:8). The sequences share approximately 28.2% identity over the 183 amino acid residues of hB7-H2 short.

FIG. 7 shows a GAP alignment of the open reading frame for hB7-H2 long (SEQ ID NO:20) with the open reading frame for hB7-H2 short (SEQ ID NO:21).

FIG. 8 shows a GAP alignment of the amino acid sequence of hB7-H2 long (SEQ ID NO:2) with the amino acid sequence of hB7-H2 short (SEQ ID NO:4).

FIG. 11 shows the amino acid sequence alignment for the human protein B7-H2 long (hB7-H2 long; SEQ ID NO:2) and the human protein B7-H2 short (hB7-H2 short; SEQ ID NO:4) with human B7-1 (hB7-1; SEQ ID NO:5), human B7-2 (hB7-2; SEQ ID NO:6), human B7RP-1 (hB7RP-1; SEQ ID NO:7), human B7RP-2 (hLB7RP-2; SEQ ID NO: 24), and human B7-H1 (hB7-H1 ; SEQ ID NO:8). The sequence alignment was generated using the Clustal method with PAM 250 residue weight table. Residues that match the consensus sequence exactly are shaded. hB7-1 and hB7RP-2 share approximately 32.7% similarity and 24.8% identity; hB7-2 and hB7RP-2 share approximately 31.2% similarity and 21.7% identity; hB7RP-1 and hB7RP-2 share approximately 35.8% similarity and 30.8% identity; hB7RP-2 and hB7-H1 share approximately 37.5% similarity and 28.8% identity; and hB7RP-2 and hB7-H2 share approximately 30.5% similarity and 21.7% identity. Percent identities were determined using the scoring matrix BLOSUM62 with a gap open penalty of 12 and a gap extend penalty of 4.

FIG. 12 shows the amino acid sequence alignment for hB7RP-1 (SEQ ID NO:7) with hB7RP-2 (SEQ ID NO:24), hB7-1 (SEQ ID NO:5), and hB7-2 (SEQ ID NO:6). The alignment was generated using the Clustal method with PAM 250 residue weight table. Signal sequences, extracellular domains, transmembrane regions, and intracellular domains are denoted by the boxes as described in the legend. The signal sequence consists of the first approximately 19 amino acids in hB7RP-1, approximately 33 amino acids in hB7RP-2, approximately 34 amino acids in hB7-1, and approximately 17 amino acids in hB7-2. The extracellular portion ranges from about amino acid (aa) 20–257 in hB7RP-1, about aa 34–246 in hB7RP-2, about aa 35–242 in hB7-1, and about aa 18–241 in hB7-2. The transmembrane region spans approximately aa 258–277 in hB7RP-1, approximately aa 247–272 in hB7RP-2, approximately aa 243–262 in hB7-1, and approximately aa 242–263 in aa hB7-2. For each protein, the remaining residues represent the intracellular domain.

FIG. 13 shows the amino acid sequence alignment for hB7-1 (SEQ ID NO:5), hB7-2 (SEQ ID NO: 6), hB7RP-1 (SEQ ID NO:7), and hB7RP-2 (SEQ ID NO:24). The alignment is based on the MegAlign program. Residues that match the consensus sequence exactly are shaded.

FIG. 14 shows a GAP alignment of the amino acid sequence of hB7RP-2 (SEQ ID NO:24) with the amino acid sequence of hB7-1 (SEQ ID NO:5). The sequences share approximately 24.8% identity over the 288 amino acid residues of hB7-1.

FIG. 15 shows a GAP alignment of the amino acid sequence of hB7RP-2 (SEQ ID NO:24) with the amino acid sequence of hB7-2 (SEQ ID NO:6). The sequences share approximately 21.7% identity over the 323 amino acid residues of hB7-2.

FIG. 16 shows a GAP alignment of the amino acid sequence of hB7RP-1 (SEQ ID NO:7) with the amino acid sequence of hB7-2 (SEQ ID NO:6). The sequences share approximately 21.2% identity over the 323 amino acid residues of hB7-2.

FIG. 17 shows a GAP alignment of the, amino acid sequence of hB7RP-1 (SEQ ID NO:7) with the amino acid sequence of hB7-1 (SEQ ID NO:5). The sequences share approximately 24.1 % identity over the 288 amino acid residues of hB7- 1.

FIG. 18 shows a GAP alignment of the amino acid sequence of hB7RP-1 (SEQ ID NO:7) with the amino acid sequence of hB7RP-2 (SEQ ID NO:24). The sequences share approximately 30.8% identity over the 316 amino acid residues of hB7RP-2.

FIG. 19 shows a GAP alignment of the amino acid sequence of hB7-1 (SEQ ID NO:5) with the amino acid sequence of hB7-2 (SEQ ID NO:6). The sequences share approximately 22.9% identity over the 323 amino acid residues of hB7-2.

FIG. 20 sets forth the open reading frame for the murine ortholog of hB7RP-2 (mB7RP-2; SEQ ID NO:27).

FIG. 21 sets forth the amino acid sequence of the murine B7RP-2 protein (mB7RP-2; SEQ ID NO:28) encoded by SEQ ID NO:27.

FIG. 22 shows a GAP alignment of the amino acid sequence of mB7RP-2 (SEQ ID NO:28) with the amino acid sequence of hB7RP-2 (SEQ ID NO:24). The sequences share approximately 88.3% identity.

FIG. 23 shows a GAP alignment of the amino acid sequence of murine B7RP-1 (mB7RP-1; GenBank Accession No. AAF45149; SEQ ID NO:29) with the amino acid sequence of mB7RP-2 (SEQ ID NO:28). The sequences share approximately 27.7% identity.

DETAILED DESCRIPTION OF THE INVENTION

The present invention provides methods and compositions for the use of novel B7-like family members. The B7-like proteins function as co-stimulators of T-cells and have the important function of regulating the adaptive immune response. While some B7 family members enhance the T-cell functions that are essential for an effective antigen-immune response, others counterbalance the CD28-mediated signals, and thus prevent an otherwise fatal over-stimulation of the lymphoid system. There is great interest in the possibility that, in disease situations in which antigens are either unknown or difficult to manipulate, immune responses may be either enhanced or terminated by manipulating the co-stimulation signals such as those signals affected by the B7 family of proteins. For example, modulating the co-stimulation signals can promote tumor immunity and reduce graft rejection, autoimmune, inflammatory, and infectious diseases.

Figures 1, 1A, 2, 3:
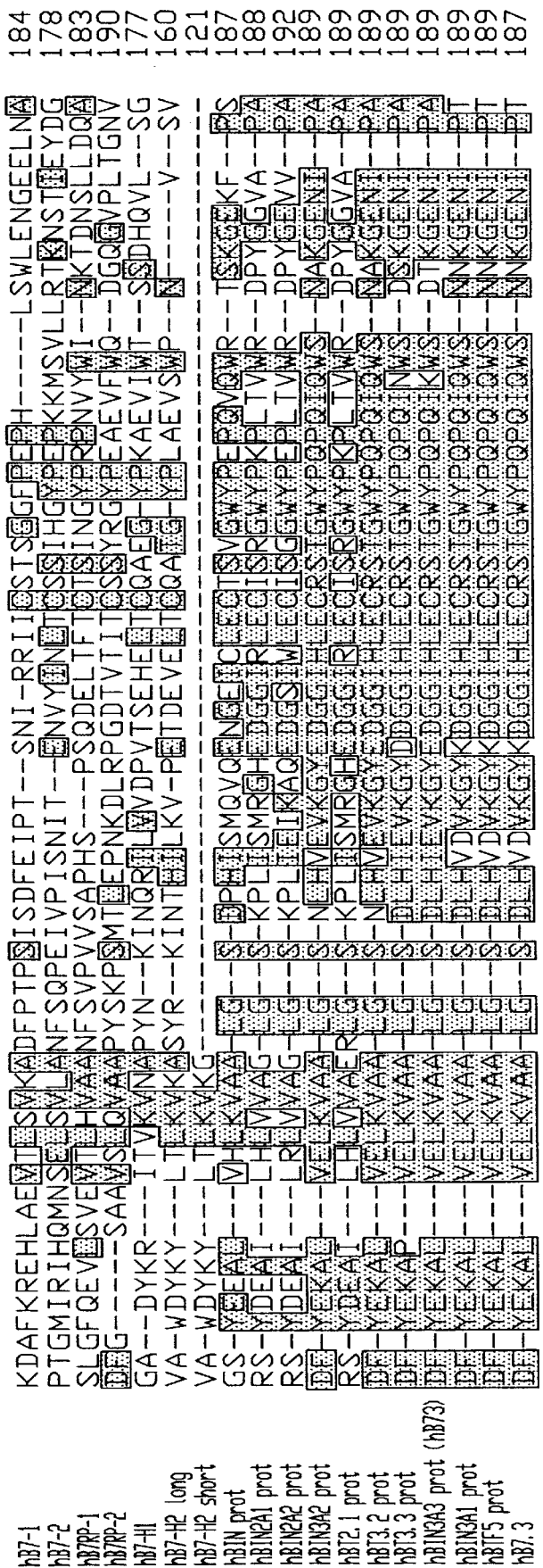
FIG. 1 shows the amino acid sequence alignment for the human protein B7-H2 long (hB7-H2 long; SEQ ID NO:2) encoded by SEQ ID NO:1 and the human protein B7-H2 short (hB7-H2 short; SEQ ID NO:4) encoded by SEQ ID NO:3 with human B7-1 (hB7-1; SP Accession Number P33681; SEQ ID NO:5), human B7-2 (hB7-2; SP Accession Number P42081; SEQ ID NO:6), human B7RP-1 (hB7RP-1 ; Accession Number AAF34739; SEQ ID NO:7), human B7RP-2 (hB7RP-2; SEQ ID NO:24), human B7-H1(hB7-H1; Accession Number AF177937; SEQ ID NO:8), human butyrophilin precursor (hBTN prot; SP Accession Number Q13410; SEQ ID NO:9), human butyrophilin, subfamily 2, member A1 (hBTN2A1 prot; Accession Number NP_008980; SEQ ID NO:10), human butyrophilin, subfamily 2, member A2 (hBTN2A2 prot; Accession Number NP_008926; SEQ ID NO: 11), human butyrophilin, subfamily 3, member A2 (hBTN3A2 prot; Accession Number NP_008978; SEQ ID NO: 12), human BT2.1 similar to butyrophilin protein (hBT2.1 prot; Accession Number AAC02650; SEQ ID NO: 13), human butyrophilin BT3.2 (hBT3.2 prot; Accession Number AAC02655; SEQ ID NO:14), human butyrophilin BT3.3 (hBT3.3 prot; Accession Number AAC02656; SEQ ID NO:15), human butyrophilin BTN3a3 (hBTN3A3 prot (B7-3); Accession Number AAB53426; SEQ ID NO:16), human butyrophilin, subfamily 3, member A1 (hBTN3A1 prot; Accession Number NP_008979; SEQ ID NO:17), human butyrophilin BTF5 (hBTF5 prot; Accession Number AAB53430; SEQ ID NO:18), and human B7.3 molecule of CD80-CD86 (hB7.3; EMBL Accession Number CAA69164; SEQ ID NO:19). The sequence alignment was generated using the Clustal method with PAM 250 residue weight table hB7-1 and hB7-2 share approximately 33.6% similarity and 22.9% identity; hB7-1 and hB7RP-1 share approximately 30.3% similarity and 24.1% identity; hB7-1 and hB7RP-2 share approximately 32.7% similarity and 24.8% identity; hB7-2 and hB7RP-1 share approximately 31.3% similarity and 21.2% identity; hB7-2 and hB7RP-2 share approximately 31.2% similarity and 21.7% identity; hB7-H1 and hB7-H2 share approximately 46.8% similarity and 37.4% identity; hB7-1 and hB7-H1 share approximately 31.1% similarity and 19.5% identity; hB7-1 and hB7-H2 share approximately 30.1% similarity and 20.8% identity; hB7-2 and hB7-H1 share approximately 28.8% similarity and 19.1% identity; hB7RP-1 and hB7-H1 share approximately 31.4% similarity and 22.3% identity; hB7RP-2 and hB7-H1 share approximately 37.5% similarity and 28.8% identity; and hB7RP-2 and hB7-H2 share approximately 30.5% similarity and 21.7% identity.
FIG. 2 shows the alignment of the open reading frame for hB7-H2 long (SEQ ID NO:20) and hB7-H2 short (SEQ ID NO:21) with the open reading frame for human B7-H1 (hB7-H1; Accession Number AF177937; SEQ ID NO:22). The sequence alignment was generated using the Clustal method noted above.
FIG. 3 shows a GAP alignment of the open reading frame of hB7-H1 (SEQ ID NO:22) with the open reading frame of hB7-H2 long (SEQ ID NO:20). The sequences share approximately 58.3% identity over the open reading frame of hB7-H2 long.

The B7 molecules are an emerging family of immunoglobulin co-stimulatory molecules, first identified on B lymphocytes. They do not share high levels of homology with each other (see FIGS. 1, 9, and 13). For example, human and mouse B7-1 have 45% identity and mouse and human B7-2 have 51% identity, which is less than normally observed for such orthologs. However, as members of the immunoglobulin superfamily, the B7 proteins share the general structural properties of immunoglobulin-like domains, for example, residues conserved throughout the immunoglobulin superfamily that are important to the immunoglobulin fold. Characteristic conserved residues can include the cysteines in the B and F strands, the tryptophane in the C strand, or the hydrophobic residues two positions ahead of the cysteines, as well as conserved patterns characteristic of immunoglobulin V(variable)-like or C(constant)-like domains (Williams and Barclay (1988) *Annu. Rev. Immunol.* 6:381–405, as cited in Fargeas (1995) *J. Exp. Med.*182:667–675).

Generally, B7 family members have the most homology occurring within their extracellular region, which consists of one amino-terminal immunoglobulin V-like domain and one membrane-proximal immunoglobulin C-like domain (Peach et al. (1995) *J. Biol. Chem.* 270:21181–21187; Dong et al. (1999) *Nature Medicine* 5(12):1365–1369; Fargeas et al. (1995) *J. Exp. Med.* 182:667–675). For example, hB7-1 (SEQ ID NO:5) has its V-like domain at approximately amino acid (aa) residues 34–139 and its C-like domain at approximately aa 140–240 (Peach et al. (1995) *J. Biol. Chem.* 270:21181–21187). hB7-2 (SEQ ID NO:6) has its V-like domain at approximately aa 18–127 and its C-like domain at approximately aa 128–235 (Peach et al. (1995) *J. Biol. Chem.* 270:21181–21187). hB7RP-1 (SEQ ID NO:7) has its V-like domain at approximately aa 20–135 and its C-like domain at approximately aa 136–246. hB7-H1 (SEQ ID NO:8) has its V-like domain at approximately aa 26–131 and its C-like domain at approximately aa 132–234 (Dong et al. (1999) *Nature Medicine* 5(12):1365–1369). These immunoglobulin-like domains may be involved in protein-protein and protein-ligand interactions.

Another common structural feature of the B7 family members is the presence of four structural cysteines within the extracellular region (see FIG. 11, where asterisks denote these conserved residues in all human B7 family members). These conserved residues are apparently involved in forming the disulfide bonds of the immunoglobulin V-like and C-like domains (see, for example, Freeman et al. (1993) *Science* 262:909–911; Azuma et al. (1993) *Nature* 366:76–79; Fargeas et al. (1995) *J. Exp. Med.* 182:667–675; Bajorath et al. (1994) *Protein Sci.* 3:2148–2150).

The B7 family members are integral proteins, and hence also comprise a signal peptide, transmembrane region, and an intracellular domain. The intracellular domain of the B7 family members tends to be quite diverse in contrast to the extracellular domain (Freeman et al. (1993) *Science* 262:909–911; Azuma et al. (1993) *Nature* 366:76–79).

The B7 molecules, which are expressed on antigen presenting cells (APCs), bind to their natural receptor or binding partner on T-cells. When bound to their natural receptors, the B7 molecules send a co-stimulatory signal to the T-cell that results in either amplification (i.e., stimulation) or blockage (i.e., inhibition) of the activated-T-cell-mediated immune response. By "activated-T-cell-mediated immune response" is intended any or all of the immune response-related activities including, but not limited to, T-cell proliferation and/or cytokine production and/or release by T-cells that have received a primary activation signal.

Previously identified members of the B7 family include the human proteins B7-1, B7-2, B7RP-1, B7-H1, and a recently reported novel member designated PD-L, as well as their mouse orthologs, such as mB7RP-1. These B7 family members also share homology with members of the butyrophilin family, a class of Type-I membrane proteins belonging to the immunoglobulin superfamily and which also contain a V-like domain.

Both B7-1 and B7-2 bind to the T cell receptors CD28 and CTLA4, thereby up-regulating (CD28) or down-regulating (CTLA4) the activated-T-cell-mediated immune response. B7RP-1 binds to the T-cell receptor ICOS, and PD-L binds to T-cell receptor PD-1. The binding partner for B7-H1, the closest homolog of the B7 molecules of the present invention, is not known. However, B7-H1 has been shown to increase production of the cytokine IL-10, which is also produced upon ligation of ICOS and PD-1 with their binding partners, making these receptors potential binding partners for B7-H2l and B7-H2s. ICOS and PD-1 may be involved in the negative regulation of various effector functions in the immune response. For example, PD-1 knockout mice develop Lupus-like autoimmune diseases (Nishimura et al. (1999) *Immunity* 11:141–151).

The present invention provides novel B7-like molecules, which are most homologous to the B7-H1 family member. By "B7-like molecules" is intended novel human sequences referred to as human B7-H2 long (hLB7-H21) and human B7-H2 short (hB7-H2s), and variants and fragments thereof. Also provided is the B7-like molecule referred to herein as human B7RP-2 (hB7RP-2; amino acid sequence set forth in SEQ ID NO:24, encoded by the nucleotide sequence set forth in SEQ ID NO:23). This protein, previously identified as PRO352 and classified as a member of the butyrophilin family of immunoglobulins (see PCT Publication No. WO 99/46281, FIG. 50 (nucleotide sequence) and FIG. 51 (amino acid sequence), herein incorporated by reference), is recognized herein as a new member of the B7 family of molecules. Further provided is the novel murine sequence referred to herein as mB7RP-2, the murine ortholog of hB7RP-2. The open-reading frame nucleotide and amino acid sequences for mB7RP-2 are set forth in FIG. 20 (SEQ ID NO:27) and FIG. 21 (SEQ ID NO:28), respectively. These novel sequences, the hB7RP-2 sequences, or variants or fragments thereof are referred to as "B7-like" sequences, indicating they share sequence similarity with B7 genes of the B7 family of immunoglobulins. The novel human and mouse B7-like sequences, the human B7-like sequences designated hB7RP-2 herein, and variants and fragments thereof are useful in the methods of the invention described elsewhere herein.

Specifically, isolated nucleic acid molecules comprising nucleotide sequences encoding the polypeptides whose amino acid sequences are given in SEQ ID NO:2 and SEQ ID NO:4, or variants or fragments thereof, are provided. The nucleotide sequences encoding these polypeptides are set forth in SEQ ID NO:1 and SEQ ID NO:3. hB7-H2 long (SEQ ID NO:1) and hB7-H2 short (SEQ ID NO:3) are different splice variants of the same gene as shown in GAP alignments (see FIGS. 7 and 8). The sequences of the present invention are members of the B7 family of immunoglobulins. The hB7-H2 long and hB7-H2 short proteins are most homologous to the family member, human B7-H1 (hB7-H1; SEQ ID NO:8). The hB7-H2 long protein displays approximately 37.4% amino acid sequence identity with hB7-H1 (see FIG. 5), while the hB7-H2 short protein shares approximately 28.2% identity with hB7-H1 (see FIG. 6).

The B7-like genes, hB7-H2 long and hB7-H2 short, were identified in a human osteoblast library. Clone hB7-H2 long encodes an approximately 2.23 Kb transcript having the corresponding cDNA set forth in SEQ ID NO:1. This transcript has an 819 nucleotide open reading frame (SEQ ID NO:20), which encodes a 273 amino acid protein (SEQ ID NO:2) having a molecular weight of approximately 30.9 kDa. An analysis of the polypeptide predicts that the N-terminal 19 amino acids represent a signal peptide. A transmembrane segment for the presumed mature peptide was predicted for amino acids (aa) 202–224 by MEMSAT. Prosite program analysis was used to predict various sites within the protein. N-glycosylation sites were predicted at aa 37–40, 64–67, 157–160, 163–166, and 189–192. Protein kinase C phosphorylation sites were predicted at aa 116–118, 122–124, 253–255, 257–259, and 264–266. Casein kinase II phosphorylation sites were predicted at aa 74–77, 211–214, 253–256, and 265–268. A tyrosine kinase phosphorylation site was predicted at aa 168–174. N-myristoylation sites were predicted at aa 35–40, 47–52, 53–58, and 98–103.

The hB7-H2 long protein possesses two immunoglobulin domains, from aa 35–104 and 136–194, as predicted by HMMer, Version 2. The predicted immunoglobulin domains reside within the extracellular domain of this protein (i.e., about aa 20–218 with respect to SEQ ID NO:2; see FIG. 9) and occupy relative positions within this region that are similar to the positions identified for the immunoglobulin V-like (approximately aa 26–131 of SEQ ID NO:8) and C-like (approximately aa 132–234 of SEQ ID NO:8) domains of hB7-H1 , the most homologous B7 family member. For a description of these V-like and C-like regions of hB7-H1, see particularly Dong et al. (1999) *Nature Medicine* 5(12):1365–1369, herein incorporated by reference. An amino acid sequence alignment of hB7-H2 long with other previously known B7 family members indicates the V-like and C-like domains of this novel protein are located at approximately aa 28–120 and aa 121–215, respectively (FIG. 11; aa residues correspond to those set forth in SEQ ID NO:2). In addition, the extracellular domain of hB7-H2 long comprises the four conserved structural cysteine residues characteristic of other B7 family members (see FIG. 11, where conserved cysteine residues are denoted by asterisks), with two of these residues occurring within the V-like domain, and two occurring within the C-like domain.

Figure 9:
FIG. 9 shows the amino acid sequence alignment for hB7-H2 long (SEQ ID NO:2) and hB7-H2 short (SEQ ID NO:4) with hB7-H1 (SEQ ID NO:8). The sequence alignment was generated using the Clustal method. Residues that match hB7-H1 exactly are shaded. The hB7-H2 long (hB7-H2l) and short (hB7-H2s) proteins are different splice variants of the same gene. The hB7-H2 long protein shares approximately 37.4% identity with the hB7-H1 protein, and approximately 71.7% identity with the hB7-H2 short protein, while the hB7-H2 short protein shares approximately 28.2% identity with the hB7-H1 protein. The proteins are type 1 transmembrane proteins and belong to the immunoglobulin superfamily (the major protein structural domains are blocked off in the figure). These proteins contain the conserved cysteine residues of immunoglobulins (marked with an asterisk) and have the highest homology in the extracellular domain. Signal sequences, extracellular domains, transmembrane regions, and intracellular domains are denoted by the boxes as described in the legend. The signal sequences consist of the first approximately 17 amino acids in hB7-H1 and approximately 19 amino acids in hB7-H2 long and short; the extracellular portion ranges from about amino acid (aa) 18–240 in hB7-H1, from about aa 20–218 in hB7-H2 long, and from about aa 20–128 in hB7-H2 short; the transmembrane region spans the next approximately 18 amino acid residues in hB7-H1 and the next approximately 19 amino acid residues in hB7-H2 long and hB7-H2 short; and the intracellular domain consists of the remaining residues. The extracellular domain of the hB7-H1 and hB7-H2 long proteins comprises an immunoglobulin V(variable)-like domain and an immunoglobulin C(constant)-like domain, while the extracellular domain of the hB7-H2 short protein comprises only the immunoglobulin V(variable)-like domain.
Figure 10:
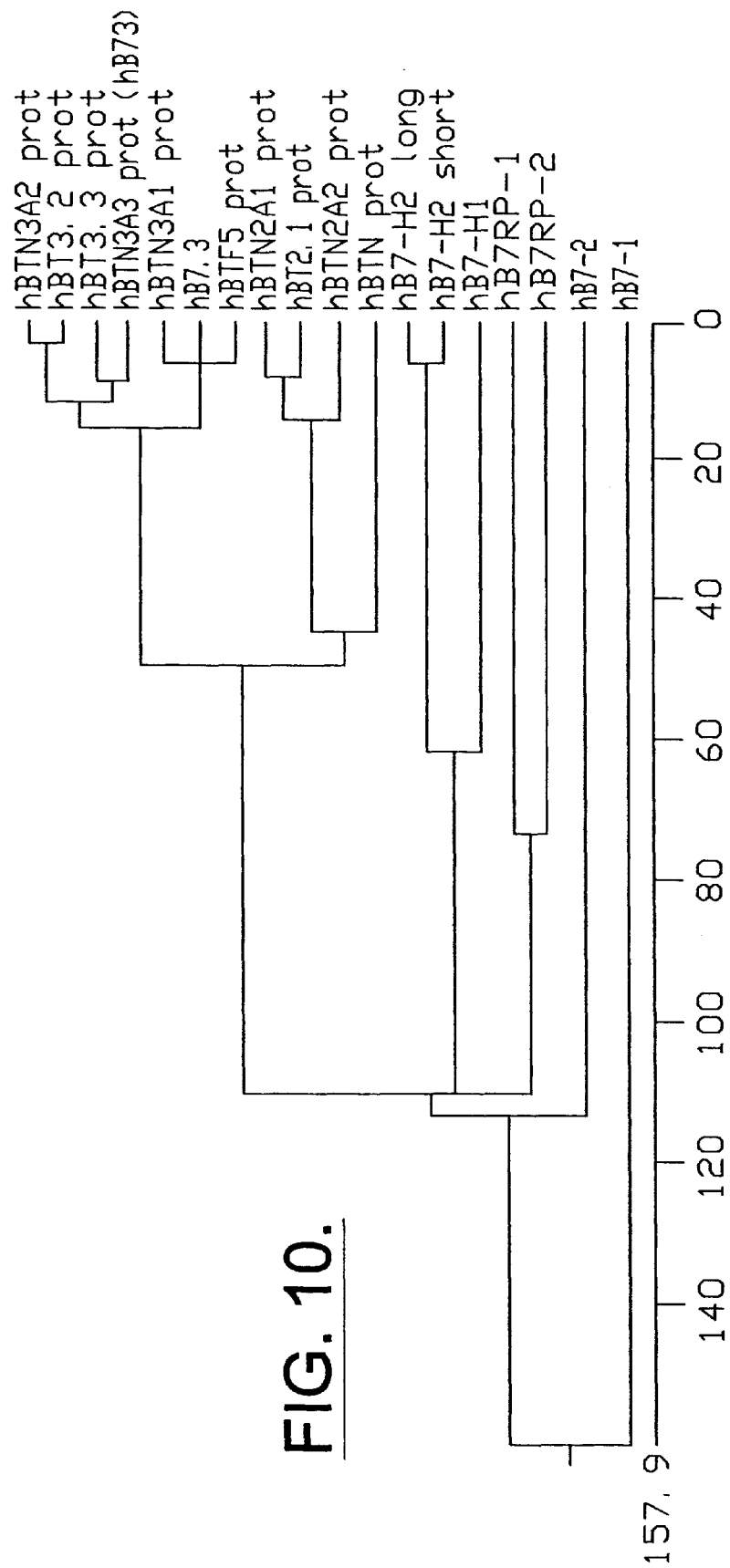
FIG. 10 shows the phylogenetic tree of the hB7 family of molecules. The hB7-H2 long and short proteins are most closely related to the hB7-H1 member of this family.

An alignment of this protein with other B7 family members shows other similar structural features within hB7-H2 long and these B7 family members, including a signal sequence, transmembrane region, and intracellular region (see FIG. 9; cross-reference FIG. 12 for an alignment of additional B7 family members showing these features).

A plasmid containing the hB7-H2 long cDNA insert was deposited with American Type Culture Collection (ATCC), 10801 University Boulevard, Manassas, Va., on Jun. 14, 2000, and assigned Accession Number PTA-2084. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Clone hB7-H2 short encodes an approximately 1.98 Kb transcript having the corresponding cDNA set forth in SEQ ID NO:3. This transcript has a 549 nucleotide open reading frame (SEQ ID NO:21), which encodes a 183 amino acid protein (SEQ ID NO:4) having a molecular weight of approximately 20.8 kDa. An analysis of the polypeptide predicts that the N-terminal 19 amino acids represent a signal peptide. A transmembrane segment for the presumed mature peptide was predicted for amino acids (aa) 112–134 by MEMSAT. Prosite program analysis was used to predict various sites within the protein. N-glycosylation sites were predicted at aa 37–40 and 64–67. Protein kinase C phosphorylation sites were predicted at aa 116–118, 163–165, 167–169, and 174–176. Casein kinase II phosphorylation sites were predicted at aa 74–77, 163–166, and 175–178. N-myristoylation sites were predicted at aa 35–40, 47–52, 53–58, and 98–103.

The hB7-H2 short protein possesses an immunoglobulin domain from aa 35–104 as predicted by HMMer, Version 2. The predicted immunoglobulin domain resides within the extracellular domain of this protein (i.e., about aa 20–128 with respect to SEQ ID NO:4; see FIG. 9). As for hB7-H2 long, an alignment of hB7-H2 short with other B7 family members indicates the immunoglobulin V-like domain in this protein resides at approximately aa 28–120 (see FIG. 11; aa residues correspond to those set forth in SEQ ID NO:4). However, unlike hB7-H2 long and other B7 family members, hB7-H2 short is missing the immunoglobulin C-like domain. The two conserved cysteine residues within the V-like domain of other B7 family members are also present within the V-like domain of hB7-H2 short (FIG. 11). As for the other B7 family members, hB7-H2 short possesses a signal sequence, transmembrane region, and an intracellular domain (see FIG. 9; cross-reference FIG. 12).

A plasmid containing the hB7-H2 short cDNA insert was deposited with American Type Culture Collection (ATCC), 10801 University Boulevard, Manassas, Va., on Jun. 14, 2000, and assigned Accession Number PTA-2085. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Isolated sequences and modulators thereof for use in methods of the present invention further encompass the human B7RP-2 (hB7RP-2) amino acid sequence set forth in SEQ ID NO:24, the novel murine B7RP-2 (mB7RP-2) amino acid sequence set forth in SEQ ID NO:28, and variants or fragments thereof, as well as nucleotide sequences encoding these polypeptides, or variants or fragments thereof. Such nucleotide sequences include the hB7RP-2 nucleotide sequence set forth as SEQ ID NO:23 and the mB7RP-2 nucleotide sequence set forth as SEQ ID NO:27. The hB7RP-2 protein shares closest homology with the previously identified B7 family member hB7RP-1 (approximately 30.8% identity; see FIG. 18).

The hB7RP-2 protein (SEQ ID NO:24) possesses two immunoglobulin domains, the first from about aa 43–124, and the second from about aa 158–222 as predicted by HMMer, Version 2. The predicted immunoglobulin domains reside within the extracellular domain of this protein (i.e., about amino acids 34–246 with respect to SEQ ID NO:24; see FIG. 12) and occupy relative positions within this region that are similar to those identified for the immunoglobulin V-like (approximately aa 20–135 of SEQ ID NO:7) and C-like (approximately aa 136–246 of SEQ ID NO:7) domains of hB7RP-1, the most homologous B7 family member. An amino acid sequence alignment of hB7RP-2 with other previously known B7 family members indicates the V-like and C-like domains of this protein are located at approximately aa 33–139 and aa 140–241, respectively (FIG. 11; aa residues correspond to those set forth in SEQ ID NO:24). In addition, the extracellular domain of hB7RP-2 also comprises the four conserved structural cysteine residues characteristic of other B7 family members (see FIG. 11, where conserved cysteine residues are denoted by asterisks), with two of these residues occurring within the V-like domain, and two occurring within the C-like domain.

An alignment of this protein with other B7 family members shows other similar structural features within hB7RP-2 and these B7 family members, including a signal sequence, transmembrane region, and intracellular region (see FIG. 12; cross-reference FIG. 9 for an alignment of additional B7 family members showing these features).

The novel murine ortholog mB7R-P-2 (SEQ ID NO:28) shares approximately 89.8% similarity and 88.3% identity with hB7RP-2 (see FIG. 22). This B7 family member shares approximately 32.3% similarity and approximately 27.7% identity with murine B7RP-1 (see FIG. 23).

The B7-like sequences of the invention are members of a family of molecules "B7 immunoglobulins" having conserved structural and/or functional features. For example, when the term "family" is used to refer to the proteins and nucleic acid molecules of the invention, it is intended to mean two or more proteins or nucleic acid molecules having sufficient amino acid or nucleotide sequence identity over their full length or within selected domains (e.g., the extracellular domain, immunoglobulin domain, immunoglobulin V-like and/or C-like domains) as defined herein. Such family members can be naturally ocurring and can be from either the same or different species. For example, a family can contain a first protein of murine origin and a homologue of that protein of human origin, as well as a second, distinct protein of human origin and a murine homologue of that protein. Common functional features of the molecules of the invention include, for example, the ability to modulate (i.e., increase or decrease) the activated-T-cell-mediated immune response following binding with their native or naturally occurring binding partners on activated T cells. Such binding partners include, but are not limited to, CD28, CTLA4, ICOS, PD-1, and other related activated T-cell receptors expressed following exposure of a T cell to a primary activation signal.

Preferred B7-like polypeptides of the present invention have an amino acid sequence sufficiently identical to the amino acid sequences of SEQ ID NO:2 and SEQ ID NO:4. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain (e.g., the extracellular domain, immunoglobulin domain, immunoglobulin V-like and/or C-like domains) and/or common functional activity. For example, amino acid or nucleotide sequences that contain a common structural domain having at least about 45%, 55%, or 65% identity, preferably 75% or 80% identity, more preferably 85% or 90%, and most preferably 91%, 92%, 93%, 94%, 95%, 96%, 97%, 98%, or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to B7-like nucleic acid molecules of the invention. BLAST protein searches can be performed with the XBLAST program, score=50, wordlength=3, to obtain amino acid sequences homologous to B7-like protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See www.ncbi.nlm.nih.gov. Another preferred, non-limiting example of a mathematical algorithm utilized for the comparison of sequences is the algorithm of Myers and Miller (1988) *CABIOS* 4:11–17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

The novel human B7-like gene sequences hB7-H21 and hB7-H2s and variants and fragments thereof are encompassed by the term "B7-like" molecules or sequences as used herein. The B7-like sequences find use in modulating T cell response. By "modulating" is intended the up-regulating or down-regulating of a response. That is, the compositions of the invention can affect the targeted activity in either a positive or negative fashion. The activation of T cells is manifested by, for example, cytokine production, cellular proliferation, signaling events, and other effector functions.

The function of T-cells is defined by the type of cytokines released upon antigenic challenge. Such cytokines are central to disease evolution in animal models of autoimmunity and infection. Proteins and/or antibodies of the invention are also useful in modulating immune and inflammatory responses.

Accordingly, another embodiment of the invention features isolated B7-like proteins and polypeptides having a B7-like protein activity. As used interchangeably herein, a "B7-like protein activity", "biological activity of a B7-like protein", or "functional activity of a B7-like protein" refers to an activity exerted by a B7-like protein, polypeptide, or nucleic acid molecule on a B7-like responsive cell as determined in vivo, or in vitro, according to standard assay techniques. A B7-like activity can be a direct activity, such as an association with or an enzymatic activity on a second protein, or an indirect activity, such as a cellular signaling activity mediated by interaction of the B7-like protein with a second protein.

In one embodiment, a B7-like activity includes the ability to provide a co-stimulatory signal to T-cells and to modulate (stimulate and/or enhance or inhibit) cellular proliferation, differentiation, morphology, and/or function, particularly that of immune cells, for example lymphocytes, such as B cells, plasma cells, T cells, and null cells, macrophages, histiocytes, dendritic cells, and granulocytes, such as neutrophils, eosinophils, basophils, and tissue mast cells. A B7-like molecule of the invention can bind to and/or modulate the function of ICOS, PD-1, CD28, CTLA-4, or a related known or unknown receptor molecule. This binding to and/or modulating of these molecules can lead to modulation of the activity of a T-cell. Examples of modulation of immune cell function through such receptors include, but are not limited to, T-cell proliferation, modulation of cytokine production and/or release (such as IL-2, IL-4, IL-5, IL-10, interferon-gamma, tumor necrosis factor-alpha, or granulocyte/macrophage colony stimulating factor production and/or release), up-regulation of molecules such as LFA-3, ICAM-1, CD154, CD69, CD25, or CD71 that mediate cell-cell interaction, and modulation of antibody secretion by B-cells.

Methods for measuring the effects resulting from interaction of a B7-like molecule with ICOS, PD-1, CD28, CTLA-4, or other related receptor are well known in the art. For example, a method for in vitro T-cell co-stimulation consists of providing purified T-cells that express ICOS, PD-1, CD28, CTLA-4, or a related receptor with a first or primary activation signal by anti-T3 monoclonal antibody (e.g., anti-CD3) or phorbol ester, or by antigen in association with class II MHC. The ability of an agent, such as the B7-like molecules of the present invention, to provide the secondary or co-stimulatory signal, necessary to modulate immune function, to these T-cells can then be assayed by any one of the several conventional assays well known in the art.

For example, with this in vitro co-stimulation assay, thymidine incorporation can be used to measure T-cell proliferation (Dong et al (1999) Nature 5:1365–1369). In this particular assay, T-cell growth is monitored by culturing the purified T-cells expressing ICOS, PD-1, DC28, CTLA-4, or a related receptor with the B7-like protein of the invention, a primary activation signal as described above, and $^3$H-thymidine. The level of T-cell proliferation is determined by measuring thymidine incorporation.

Cytokine production can be measured using a similar approach. Purified T-cells are cultured in the presence of the B7-like protein and a primary activation signal. The level of various cytokines in the supernatant can be determined by sandwich enzyme-linked immunosorbent assays or other conventional assays. See, for example, Dong et al (1999) Nature 5:1365–1369.

Up-regulation of molecules such as LFA-3, ICAM-1, CD154, CD25, CD69, or CD71 that mediate cell-cell interaction can also be measured with this co-stimulation assay as described in Hutloff et al. (1999) Nature 397:263–266. In this case, stimulated CD4$^+$ T-cells are incubated in the presence of a control monoclonal antibody such as MOPC-21 or an antibody to the receptor molecule being studied (ICOS, PD-1, DC28, CTLA-4, or a related-receptor) and in the presence of the B7-like protein of the invention. The level of expression of the cell surface molecule of interest is measured by flow cytometry with an FITC-labeled antibody specific for this antigen (Kroczek et al. (1994) Immunol. Rev. 138:39–59).

Modulation of antibody secretion by B-cells as a result of B7-like interaction with an ICOS, PD-1, CD28, CTLA-4, or other related receptor can be measured using the co-stimulation assay. For example, CD4$^+$ T-cells can be cultured with tonsillar B-cells and provided with a primary signal as described and a secondary B7-like molecule of the invention for co-stimulation. IgM and IgG levels in the supernatant at subsequent points in time are then determined by ELISA (Hutloff et al. (1999) Nature 397:263–266).

In view of the biological function of the B7-like molecules of the invention, these molecules and modulators thereof can be used to monitor, detect, modulate, and/or act as targets for identifying agents that modulate T-cell function, and are thus useful in methods directed to modulation, diagnosis, and treatment of T-cell-related or T-lymphocyte-related disorders, including, but not limited to, atopic conditions, such as asthma and allergy, including allergic rhinitis, psoriasis, the effects of pathogen infection, chronic inflammatory diseases, chronic obstructive pulmonary diseases, autoimmune diseases, graft rejection, graft versus host disease and neoplasia.

Other diseases and disorders that can be treated using the molecules of the invention include, but are not limited to, such immune disorders as inflammatory bowel diseases such as Crohn's disease and ulcerative colitis, reactive arthritis, including Lyme disease, rheumatoid arthritis, insulin-dependent diabetes, organ-specific autoimmunity, including multiple sclerosis, Hashimoto's thyroiditis and Grave's disease, Lupus-erythematosus, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, and glomerular nephritis and certain pathogen susceptibilities such as helminthic (e.g., leishmaniasis), certain viral infections, including HIV, and bacterial infections, including tuberculosis and lepromatous leprosy.

Compositions of the invention are useful to inhibit the function of malignant B- and T-cells in cancers such as B lymphoblastic leukemia/lymphoma and carcinomas, and T lymphoblastic leukemia/lymphoma and are useful for treatment of viral diseases and cancers such as herpes, Kaposi's sarcoma, genital warts, hairy cell leukemia, melanoma, and renal cell carcinoma.

In addition, compositions of the invention are useful in the modulation, diagnosis, and treatment of disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by the effects of B7-like molecule activity in bone cells, e.g., osteoclasts and osteoblasts, that may in turn result in bone formation and degeneration. For example, B7-like molecules may support different activities of bone resorbing osteoclasts such as the stimulation of differentiation of monocytes and mononuclear phagocytes into osteoclasts. Accordingly, B7-like molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anticonvulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

An "isolated" or "purified" B7-like nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated B7-like nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A B7-like protein that is substantially free of cellular material includes preparations of B7-like protein having less than about 30%, 20%, 10%, or 5% (by dry weight) of non-B7-like protein (also referred to herein as a "contaminating protein"). When the B7-like protein or biologically active portion thereof is recombinantly produced, preferably, culture medium represents less than about 30%, 20%, 10%, or 5% of the volume of the protein preparation. When B7-like protein is produced by chemical synthesis, preferably the protein preparations have less than about 30%, 20%, 10%, or 5% (by dry weight) of chemical precursors or non-B7-like chemicals.

Various aspects of the invention are described in further detail in the following subsections.

I. Isolated Nucleic Acid Molecules

One aspect of the invention pertains to isolated nucleic acid molecules comprising nucleotide sequences encoding B7-like proteins and polypeptides or biologically active portions thereof, as well as nucleic acid molecules sufficient for use as hybridization probes to identify B7-like-encoding nucleic acids (e.g., B7-like mRNA) and fragments for use as PCR primers for the amplification or mutation of B7-like nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the B7-like proteins of the present invention include sequences set forth in SEQ ID NO:1 and SEQ ID NO:3, the nucleotide sequence of the cDNA insert of the plasmid deposited with the ATCC as Accession Number PTA-2084 (the "cDNA of ATCC 2084"), the nucleotide sequence of the cDNA insert of the plasmid deposited with the ATCC as Accession Number PTA-2085 (the "cDNA of ATCC 2085"), and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the B7-like proteins encoded by these nucleotide sequences are set forth in SEQ ID NO:2 and SEQ ID NO:4. Further provided are nucleotide sequences encoding the novel murine B7-like protein designated mB7RP-2, including the sequence set forth in SEQ ID NO:27, and complements thereof. The corresponding amino acid sequence for the B7-like protein encoded by SEQ ID NO:27 is set forth in SEQ ID NO:28.

Nucleic acid molecules that are fragments of these B7-like nucleotide sequences are also encompassed by the present invention. By "fragment" is intended a portion of the nucleotide sequence encoding a B7-like protein. A fragment of a B7-like nucleotide sequence may encode a biologically active portion of a B7-like protein, or it may be a fragment that can be used as a hybridization probe or PCR primer using methods disclosed below. A biologically active portion of a B7-like protein can be prepared by isolating a portion of one of the nucleotide sequences of the invention, expressing the encoded portion of the B7-like protein (e.g., by recombinant expression in vitro), and assessing the activity of the encoded portion of the B7-like protein. Nucleic acid molecules that are fragments of a B7-like nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 nucleotides, or up to the number of nucleotides present in a full-length B7-like nucleotide sequence disclosed herein (for example, up to 2229, 1975, or 948 nucleotides for SEQ ID NO:1, SEQ ID NO:3, or SEQ ID NO:27, respectively), depending upon the intended use.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of a B7-like nucleotide sequence that encodes a biologically active portion of a B7-like protein of the invention will encode at least about 20, 25, 30, 50, 75, 100, 125, 150, or 175 contiguous amino acids, or up to the total number of amino acids present in a full-length B7-like protein of the invention (for example, 273 amino acids for SEQ ID NO:2, 183 amino acids for SEQ ID NO:4, and 315 amino acids for SEQ ID NO:28). Fragments of a B7-like nucleotide sequence that are useful as hybridization probes for PCR primers generally need not encode a biologically active portion of a B7-like protein.

Nucleic acid molecules that are variants of the B7-like nucleotide sequences disclosed herein are also encompassed by the present invention. "Variants" of the B7-like nucleotide sequences include those sequences that encode the B7-like proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the B7-like proteins disclosed in the present invention as discussed below. Generally, nucleotide sequence variants of the invention will have at least about 45%, 55%, 65%, 70%, 75%, 80%, 85%, 90%, 91%, 92%, 93%, 94%, 95%, 96%, 97%, 98%, or 99% identity to a particular nucleotide sequence disclosed herein. A variant B7-like nucleotide sequence will encode a B7-like protein that has an amino acid sequence having at least about 45%, 55%, 65%, 70%, 75%, 80%, 85%, 90%, 91%, 92%, 93%, 94%, 95%, 96%, 97%, 98%, or 99% identity to the amino acid sequence of a B7-like protein disclosed herein.

In addition to the B7-like nucleotide sequences shown in SEQ ID NOs:1, 3, and 27, the nucleotide sequence of the cDNA of ATCC 2084, and the nucleotide sequence of the cDNA of ATCC 2085, it will be appreciated by those skilled in the art that DNA sequence polymorphisms that lead to changes in the amino acid sequences of B7-like proteins may exist within a population (e.g., the human population). Such genetic polymorphism in a B7-like gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a B7-like protein, preferably a mammalian B7-like protein. As used herein, the phrase "allelic variant" refers to a nucleotide sequence that occurs at a B7-like locus or to a polypeptide encoded by the nucleotide sequence. Such natural allelic variations can typically result in 1–5% variance in the nucleotide sequence of the B7-like gene. Any and all such nucleotide variations and resulting amino acid polymorphisms or variations in a B7-like sequence that are the result of natural allelic variation and that do not alter the functional activity of B7-like proteins are intended to be within the scope of the invention.

Moreover, nucleic acid molecules encoding B7-like proteins from other species (B7-like homologues), which have a nucleotide sequence differing from that of the B7-like sequences disclosed herein, are intended to be within the scope of the invention. For example, nucleic acid molecules corresponding to natural allelic variants and homologues of the human B7-like cDNA of the invention can be isolated based on their identity to the human B7-like nucleic acid disclosed herein using the human cDNA, or a portion thereof, as a hybridization probe according to standard hybridization techniques under stringent hybridization conditions as disclosed below.

In addition to naturally occurring allelic variants of the B7-like sequences that may exist in the population, the skilled artisan will further appreciate that changes can be introduced by mutation into the nucleotide sequences of the invention thereby leading to changes in the amino acid sequence of the encoded B7-like proteins, without altering the biological activity of the B7-like proteins. Thus, an isolated nucleic acid molecule encoding a B7-like protein having a sequence that differs from that of SEQ ID NO:2, SEQ ID NO:4, or SEQ ID NO:28 can be created by introducing one or more nucleotide substitutions, additions, or deletions into the corresponding nucleotide sequence disclosed herein (i.e., SEQ ID NO:1, 3, or 27), such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a B7-like protein (e.g., the sequence of SEQ ID NO:2, SEQ ID NO:4, or SEQ ID NO:28) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, such as the four structural cysteines (FIG. 1, stars), which are apparently involved in forming the disulfide bonds of the immunoglobulin V and C domains (Freeman et al. (1993) *Science* 262:909–911; Azuma et al. (1993) *Nature* 366:76–79; Peach et al. (1995) *J. Biol. Chem.* 270:21181–21187; Fargeas et al. (1995) *J. Exp. Med.* 182:667–675; Bajorath et al. (1994) *Protein Sci.* 3:2148–2150), and are well conserved in all B7 family members.

Alternatively, variant B7-like nucleotide sequences can be made by introducing mutations randomly along all or part of a B7-like coding sequence, such as by saturation mutagenesis, and the resultant mutants can be screened for B7-like biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof. The B7-like nucleotide sequences of the invention, and fragments and variants thereof, can be used as probes and/or primers to identify and/or clone B7-like homologues in other cell types, e.g., from other tissues, as well as B7-like homologues from other mammals. Such probes can be used to detect transcripts or genomic sequences encoding the same or identical proteins. These probes can be used as part of a diagnostic test kit for identifying cells or tissues that misexpress a B7-like protein, such as by measuring levels of a B7-like-encoding nucleic acid in a sample of cells from a subject, e.g., detecting B7-like mRNA levels or determining whether a genomic B7-like gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications*(Academic Press, N.Y.). B7-like nucleotide sequences isolated based on their sequence identity to the B7-like nucleotide sequences set forth herein or to fragments and variants thereof are encompassed by the present invention.

In a hybridization method, all or part of a known B7-like nucleotide sequence can be used to screen cDNA or genomic libraries. Methods for construction of such cDNA and genomic libraries are generally known in the art and are disclosed in Sambrook et al. (1989) *Molecular Cloning: A*

*Laboratory Manual* (2d ed., Cold Spring Harbor Laboratory Press, Plainview, N.Y.). The so-called hybridization probes may be genomic DNA fragments, cDNA fragments, RNA fragments; or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known B7-like nucleotide sequence disclosed herein. Degenerate primers designed on the basis of conserved nucleotides or amino acid residues in a known B7-like nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a B7-like nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified B7-like nucleic acid molecule hybridizes under stringent conditions to a probe that is a nucleic acid molecule comprising one of the B7-like nucleotide sequences of the invention or a fragment thereof. In another embodiment, the previously unknown B7-like nucleic acid molecule is at least about 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising one of the B7-like nucleotide sequences disclosed herein or a fragment thereof.

Accordingly, in another embodiment, an isolated previously unknown B7-like nucleic acid molecule of the invention is at least about 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising one of the nucleotide sequences of the invention, preferably the coding sequence set forth in SEQ ID NO:1, SEQ ID NO:3, SEQ ID NO:27, the cDNA of ATCC 2084, the cDNA of ATCC 2085, or a complement, fragment, or variant thereof.

As used herein, the term "hybridizes under stringent conditions" is intended to describe conditions for hybridization and washing under which nucleotide sequences having at least about 60%, 65%, 70%, preferably 75% identity to each other typically remain hybridized to each other. Such stringent conditions are known to those skilled in the art and can be found in *Current Protocols in Molecular Biology* (John Wiley & Sons, New York (1989)), 6.3.1–6.3.6. A preferred, non-limiting example of stringent hybridization conditions is hybridization in 6× sodium chloride/sodium citrate (SSC) at about 45° C., followed by one or more washes in 0.2 ×SSC; 0.1% SDS at 50–65° C. In another preferred embodiment, stringent conditions comprise hybridization in 6×SSC at 42° C., followed by washing with 1×SSC at 55° C. Preferably, an isolated nucleic acid molecule that hybridizes under stringent conditions to a B7-like sequence of the invention corresponds to a naturally occurring nucleic acid molecule. As used herein, a "naturally occurring" nucleic acid molecule refers to an RNA or DNA molecule having a nucleotide sequence that occurs in nature (e.g., encodes a natural protein).

Thus, in addition to the B7-like nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the B7-like nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire B7-like coding strand, or to only a portion thereof, e.g., all or part of the protein coding region (or open reading frame). An antisense nucleic acid molecule can be antisense to a noncoding region of the coding strand of a nucleotide sequence encoding a B7-like protein. The noncoding regions are the 5' and 3' sequences that flank the coding region and are not translated into amino acids.

Given the coding-strand sequence encoding a B7-like protein disclosed herein (e.g., SEQ ID NO:1, SEQ ID NO:3, and SEQ ID NO:27), antisense nucleic acids of the invention can be designed according to the rules of Watson and Crick base pairing. The antisense nucleic acid molecule can be complementary to the entire coding region of B7-like mRNA, but more preferably is an oligonucleotide that is antisense to only a portion of the coding or noncoding region of B7-like mRNA. For example, the antisense oligonucleotide can be complementary to the region surrounding the translation start site of B7-like mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

When used therapeutically, the antisense nucleic acid molecules of the invention are typically administered to a subject or generated in situ such that they hybridize with or bind to cellular mRNA and/or genomic DNA encoding a B7-like protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585–591)) can be used to catalytically cleave B7-like mRNA transcripts to thereby inhibit translation of B7-like mRNA. A ribozyme having specificity for a B7-like-encoding nucleic acid can be designed based upon the nucleotide sequence of a B7-like cDNA disclosed herein (e.g., SEQ ID NO:1 and SEQ ID NO:3). See, e.g., Cech et al., U.S. Pat. No. 4,987,071; and Cech et al., U.S. Pat. No. 5,116,742. Alternatively, B7-like mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules that form triple helical structures. For example, B7-like gene expression can be inhibited by targeting nucleotide sequences complementary to the regulatory region of the B7-like protein (e.g., the B7-like promoter and/or enhancers) to form triple helical structures that prevent transcription of the B7-like gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described, for example, in Hyrup et al. (1996), supra; Perry-O'Keefe et al. (1996) *Proc. Natl. Acad. Sci. USA* 93:14670.

PNAs of a B7-like molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra); or as probes or primers for DNA sequence and hybridization (Hyrup (1996), supra; Perry-O'Keefe et al. (1996), supra).

In another embodiment, PNAs of a B7-like molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63; Mag et al. (1989) *Nucleic Acids Res.* 17:5973; and Peterson et al. (1975) *Bioorganic Med. Chem. Lett.* 5:1119.

II. Isolated B7-like Proteins and Anti B7-like Antibodies

B7-like proteins are also encompassed within the present invention. By "B7-like protein" is intended a protein having the amino acid sequence set forth in SEQ ID NO: 2, SEQ ID NO:4, or SEQ ID NO:28, as well as fragments, biologically active portions, and variants thereof.

"Fragments" or "biologically active portions" include polypeptide fragments suitable for use as immunogens to raise anti-B7-like antibodies. Fragments include peptides comprising amino acid sequences sufficiently identical to or derived from the amino acid sequence of a B7-like protein, or partial-length protein, of the invention and exhibiting at least one activity of a B7-like protein, but which include fewer amino acids than the full-length SEQ ID NO:2, SEQ ID NO:4, or SEQ ID NO:28 B7-like proteins disclosed herein. Typically, biologically active portions comprise a domain or motif with at least one activity of the B7-like protein. A biologically active portion of a B7-like protein can be a polypeptide which is, for example, 17, 25, 50, 100 or more amino acids in length. Such biologically active portions can be prepared by recombinant techniques and evaluated for one or more of the functional activities of a native B7-like protein. As used here, a fragment comprises at least 17 contiguous amino acids of SEQ ID NO:2, SEQ ID NO:4, or SEQ ID NO:28. The invention encompasses other fragments, however, such as any fragment in the protein greater than 17, 18, 19, or 20 amino acids.

By "variants" is intended proteins or polypeptides having an amino acid sequence that is at least about 45%, 55%, 65%, 70%, 75%, 80%, 85%, 90%, 91%, 92%, 93%, 94%, 95%, 96%, 97%, 98%, or 99% identical to the amino acid sequence of SEQ ID NO:2, SEQ ID NO:4, or SEQ ID NO:28. Variants also include polypeptides encoded by the cDNA insert of the plasmid deposited with ATCC as Accession Number 2084, the cdna insert of the plasmid deposited with ATCC as Accession Number 2085, or polypeptides encoded by a nucleic acid molecule that hybridizes to the nucleic acid molecule of SEQ ID NO:1, SEQ ID NO:3, or SEQ ID NO:27, or a complement thereof, under stringent conditions. Such variants generally retain the functional activity of the B7-like proteins of the invention. Variants include polypeptides that differ in amino acid sequence due to natural allelic variation or mutagenesis.

The invention also provides B7-like chimeric or fusion proteins. As used herein, a B7-like "chimeric protein" or "fusion protein" comprises a B7-like polypeptide operably linked to a non-B7-like polypeptide. A "B7-like polypeptide" refers to a polypeptide having an amino acid sequence corresponding to a B7-like protein, whereas a "non-B7-like polypeptide" refers to a polypeptide having an amino acid sequence corresponding to a protein that is not substantially identical to the B7-like protein, e.g., a protein that is different from the B7-like protein and which is derived from the same or a different organism. Within a B7-like fusion protein, the B7-like polypeptide can correspond to all or a portion of a B7-like protein, preferably at least one biologically active portion of a B7-like protein. Within the fusion protein, the term "operably linked" is intended to indicate that the B7-like polypeptide and the non-B7-like polypeptide are fused in-frame to each other. The non-B7-like polypeptide can be fused to the N-terminus or C-terminus of the B7-like polypeptide.

One useful fusion protein is a GST-B7-like fusion protein in which the B7-like sequences are fused to the C-terminus of the GST sequences. Such fusion proteins can facilitate the purification of recombinant B7-like proteins.

In yet another embodiment, the fusion protein is a B7-like-immunoglobulin fusion protein in which all or part of a B7-like protein is fused to sequences derived from a member of the immunoglobulin protein family. For example, a fusion protein comprising a first peptide that includes the B7-like protein fused to a second peptide, such as an immunoglobulin constant region, that alters the solubility, binding affinity, stability and/or valency of the first peptide are provided. In one embodiment, a fusion protein is produced comprising a first peptide having the amino acid residues of the extracellular region of the B7-like protein joined to a second peptide that includes an immunoglobulin constant region. Such immunoglobulin constant regions include, for example, a human Cγ1 domain or Cγ4 domain (e.g., the hinge, CH2 and CH3 regions of human IgCγ1, or human IgCγ4, see e.g., Capon et al. U.S. Pat. No. 5,116,964, incorporated herein by reference). Fusion proteins and peptides produced by recombinant technique may be secreted and isolated from a mixture of cells and medium containing the protein or peptide. Alternatively, the protein or peptide may be retained cytoplasmically and the cells harvested, lysed and the protein isolated.

The B7-like-immunoglobulin fusion proteins of the invention can be incorporated into pharmaceutical compositions and administered to a subject to modulate B7-like-activity in vivo. The B7-like-immunoglobulin fusion proteins can be used to either up-regulate or inhibit the expression of one or more B7-like proteins, or to increase or block binding of one or more B7-like proteins to their natural target molecules on T cells, to thereby provide enhancement or suppression of cell-mediated immune responses in vivo. Modulation of the B7-like protein/B7-like target molecule interaction may be useful therapeutically, both for treating proliferative and differentiative disorders and for modulating (e.g., promoting or inhibiting) cell survival. Moreover, the B7-like-immunoglobulin fusion proteins of the invention can be used as immunogens to produce anti-B7-like antibodies in a subject, to purify B7-like ligands including the B7-like natural target molecules, and in screening assays to identify molecules that inhibit the interaction of a B7-like protein with a B7-like ligand and/or natural target molecule.

Preferably, a B7-like chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a B7-like-encoding nucleic acid can be cloned into a commercially available expression vector such that it is linked in-frame to an existing fusion moiety.

Variants of the B7-like proteins can function as either B7-like agonists (mimetics) or as B7-like antagonists. Variants of the B7-like protein can be generated by mutagenesis, e.g., discrete point mutation or truncation of the B7-like protein. An agonist of the B7-like protein can retain substantially the same, or a subset, of the biological activities of the naturally occurring form of the B7-like protein. An antagonist of the B7-like protein can inhibit one or more of the activities of the naturally occurring form of the B7-like protein by, for example, competitively binding to a downstream or upstream member of a cellular signaling cascade that includes the B7-like protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the B7-like proteins.

Variants of a B7-like protein that function as either B7-like agonists or as B7-like antagonists can be identified by screening combinatorial libraries of mutants, e.g., truncation mutants, of a B7-like protein for B7-like protein agonist or antagonist activity. In one embodiment, a variegated library of B7-like variants is generated by combinatorial mutagenesis at the nucleic acid level and is encoded by a variegated gene library. A variegated library of B7-like variants can be produced by, for example, enzymatically ligating a mixture of synthetic oligonucleotides into gene sequences such that a degenerate set of potential B7-like sequences is expressible as individual polypeptides, or alternatively, as a set of larger fusion proteins (e.g., for phage display) containing the set of B7-like sequences therein. There are a variety of methods that can be used to produce libraries of potential B7-like variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential B7-like sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a B7-like protein coding sequence can be used to generate a variegated population of B7-like fragments for screening and subsequent selection of variants of a B7-like protein. In one embodiment, a library of coding sequence fragments can be generated by treating a double-stranded PCR fragment of a B7-like coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the B7-like protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of B7-like proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify B7-like variants (Arkin and Yourvan (1992) *Proc. Natl. Acad. Sci. USA* 89:7811–7815; Delgrave et al. (1993) *Protein Engineering* 6(3):327–331).

An isolated B7-like polypeptide of the invention can be used as an immunogen to generate antibodies that bind B7-like proteins using standard techniques for polyclonal and monoclonal antibody preparation. The full-length B7-like protein can be used or, alternatively, the invention provides antigenic peptide fragments of B7-like proteins for use as immunogens. The antigenic peptide of a B7-like protein comprises at least 8, preferably 10, 15, 20, 25, or 30 amino acid residues of the amino acid sequence shown in SEQ ID NO:2, SEQ ID NO:4, or SEQ ID NO:28 and encompasses an epitope of a B7-like protein such that an antibody raised against the peptide forms a specific immune complex with the B7-like protein. Preferred epitopes encompassed by the antigenic peptide are regions of a B7-like protein that are located on the surface of the protein, e.g., hydrophilic regions. For example, an analysis of a hydropathy plot of the open reading frame of hB7-H21 indicates that the regions corresponding to amino acids 60–75, 95–105, 165–175, and 210–220 may be useful antigenic peptides for the generation of antibodies.

Accordingly, another aspect of the invention pertains to anti-B7-like polyclonal and monoclonal antibodies that bind a B7-like protein. Polyclonal anti-B7-like antibodies can be prepared by immunizing a suitable subject (e.g., rabbit, goat, mouse, or other mammal) with a B7-like immunogen. The anti-B7-like antibody titer in the immunized subject can be monitored over time by standard techniques, such as with an enzyme linked immunosorbent assay (ELISA) using immobilized B7-like protein. At an appropriate time after immunization, e.g., when the anti-B7-like antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.,* 54:387–402).

Alternative to preparing monoclonal antibody-secreting hybridomas, a monoclonal anti-B7-like antibody can be identified and isolated by screening a recombinant combinatorial immunoglobulin library (e.g., an antibody phage display library) with a B7-like protein to thereby isolate immunoglobulin library members that bind the B7-like protein. Kits for generating and screening phage display libraries are commercially available (e.g., the Pharmacia *Recombinant Phage Antibody System*, Catalog No. 27–9400-01; and the Stratagene SurfZAP™ *Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-B7-like antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86/101533 and WO 87/02671; European Patent Application Nos. 184,187, 171,496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-B7-like antibody (e.g., monoclonal antibody) can be used to isolate B7-like proteins by standard techniques, such as affinity chromatography or immunoprecipitation. An anti-B7-like antibody can facilitate the purification of natural B7-like protein from cells and of recombinantly produced B7-like protein expressed in host cells. Moreover, an anti-B7-like antibody can be used to detect B7-like protein (e.g., in a cellular lysate or cell supernatant) in order to evaluate the abundance and pattern of expression of the B7-like protein. Anti-B7-like antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^3H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody hetcroconjugate as described by Segal in U.S. Pat. No. 4,676,980.

III. Recombinant Expression Vectors and Host Cells

Another aspect of the invention pertains to vectors, preferably expression vectors, containing a nucleic acid encoding a B7- like protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., B7-like proteins, mutant forms of B7-like proteins, fusion proteins, etc.).

The recombinant expression vectors of the invention can be designed for expression of B7-like protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, Calif.), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cereivisiae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufmnan et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (e.g., liver-specific promoter; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Patent Publication No. 264,166). Developmentally-regulated promoters are also encompassed, for example the murine hox homeobox promoters (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to B7-like mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics, Vol.* 1 (1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboraty Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding a B7-like protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) B7-like protein. Accordingly, the invention further provides methods for producing B7-like protein using the host cells of the invention. In one embodiment, the method comprises culturing the host cell of the invention, into which a recombinant expression vector encoding a B7-like protein has been introduced, in a suitable medium such that B7-like protein is produced. In another embodiment, the method further comprises isolating B7-like protein from the medium or the host cell.

The host cells of the invention can also be used to produce nonhuman transgenic animals. For example, in one embodiment, a host cell of the invention is a fertilized oocyte or an embryonic stem cell into which B7-like-coding sequences have been introduced. Such host cells can then be used to create nonhuman transgenic animals in which exogenous B7-like sequences have been introduced into their genome or homologous recombinant animals in which endogenous B7-like sequences have been altered. Such animals are useful for studying the function and/or activity of B7-like genes and proteins and for identifying and/or evaluating modulators of B7-like activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous B7-like gene has been altered by homologous recombination between the endogenous gene and an exogenous DNA molecule introduced into a cell of the animal, e.g., an embryonic cell of the animal, prior to development of the animal.

A transgenic animal of the invention can be created by introducing B7-like-encoding nucleic acid into the male pronuclei of a fertilized oocyte, e.g., by microinjection, retroviral infection, and allowing the oocyte to develop in a pseudopregnant female foster animal. The B7-like cDNA sequence can be introduced as a transgene into the genome of a nonhuman animal. Alternatively, a homologue of the mouse B7-like gene can be isolated based on hybridization and used as a transgene. Intronic sequences and polyadenylation signals can also be included in the transgene to increase the efficiency of expression of the transgene. A tissue-specific regulatory sequence(s) can be operably linked to the B7-like transgene to direct expression of B7-like protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) Manipulating the Mouse Embryo (Cold Spring Harbor Laboratory Press, Cold Spring Harbor, N.Y., 1986). Similar methods are used for production of other transgenic animals. A transgenic founder animal can be identified based upon the presence of the B7-like transgene in its genome and/or expression of B7-like mRNA in tissues or cells of the animals. A transgenic founder animal can then be used to breed additional animals carrying the transgene. Moreover, transgenic animals carrying a transgene encoding B7-like gene can further be bred to other transgenic animals carrying other transgenes.

To create a homologous recombinant animal, one prepares a vector containing at least a portion of a B7-like gene or a homolog of the gene into which a deletion, addition, or substitution has been introduced to thereby alter, e.g., functionally disrupt, the B7-like gene. In a preferred embodiment, the vector is designed such that, upon homologous recombination, the endogenous B7-like gene is functionally disrupted (i.e., no longer encodes a functional protein; also referred to as a "knock out" vector). Alternatively, the vector can be designed such that, upon homologous recombination, the endogenous B7-like gene is mutated or otherwise altered but still encodes functional protein (e.g., the upstream regulatory region can be altered to thereby alter the expression of the endogenous B7-like protein). In the homologous recombination vector, the altered portion of the B7-like gene is flanked at its 5' and 3' ends by additional nucleic acid of the B7-like gene to allow for homologous recombination to occur between the exogenous B7-like gene carried by the vector and an endogenous B7-like gene in an embryonic stem cell. The additional flanking B7-like nucleic acid is of sufficient length for successful homologous recombination with the endogenous gene. Typically, several kilobases of flanking DNA (at both the 5' and 3' ends) are included in the vector (see, e.g., Thomas and Capecchi (1987) Cell 51:503 for a description of homologous recombination vectors). The vector is introduced into an embryonic stem cell line (e.g., by electroporation), and cells in which the introduced B7-like gene has homologously recombined with the endogenous B7-like gene are selected (see, e.g., Li et al. (1992) Cell 69:915). The selected cells are then injected into a blastocyst of an animal (e.g., a mouse) to form aggregation chimeras (see, e.g., Bradley (1987) in Teratocarcinomas and Embryonic Stem Cells: A Practical Approach, ed. Robertson (IRL, Oxford pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in BioTechnology 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) Nature 385:810–813 and PCT Publication Nos. WO 97/07668 and WO 97/07669.

IV. Pharmaceutical Compositions

The B7-like nucleic acid molecules, B7-like proteins, and modulators thereof, e.g., anti-B7-like antibodies (also referred to herein as "active compounds") of the invention can be incorporated into pharmaceutical compositions suitable for administration. Such compositions typically comprise the nucleic acid molecule, protein, or modulators thereof, e.g., antibody or small molecule, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a B7-like protein or anti-B7-like antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 $\mu$g/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 $\mu$g/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in PCT Publication No. WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express B7-like protein (e.g., via a recombinant expression vector in a host cell in gene therapy applications), to detect B7-like mRNA (e.g., in a biological sample) or a genetic lesion in a B7-like gene, and to modulate B7-like activity. In addition, the B7-like proteins can be used to screen drugs or compounds that modulate immune response as well as to treat disorders characterized by insufficient or excessive production of B7-like protein or production of B7-like protein forms that have decreased or aberrant activity compared to B7-like wild type protein. In addition, the anti-B7-like antibodies of the invention can be used to detect and isolate B7-like proteins and modulate B7-like activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to B7-like proteins or have a stimulatory or inhibitory effect on, for example, B7-like expression or B7-like activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to a B7-like protein of the invention or to a B7-like binding partner can be accomplished, for example, by coupling the test compound with a radioisotope or enzymatic label such that binding of the test compound to the B7-like protein or biologically active portion thereof can be determined by detecting the labeled compound in a complex. For example, test compounds can be labeled with $^{125}$I, $^{35}$S, $^{14}$C, or $^3$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

The invention also features methods of identifying the natural binding partner(s) of the novel B7-like molecules of the invention. Methods of identifying a binding partner for a novel ligand are known in the art. A B7-like molecule of the invention modulates the activity of a T-cell through the interaction with (i.e., co-stimulation) such a receptor molecule. The measurement of this activity can be used to determine whether the B7-like molecule of the invention interacts with such a receptor. Examples of modulation of immune cell function through receptors such as ICOS, PD-1, CD28, CTLA-4, or other related receptors include, but are not limited to, T-cell proliferation, modulation of cytokine production and/or release (such as IL-2, IL-4, IL-5, IL-10, interferon-gamma, tumor necrosis factor-alpha, or granulocyte/macrophage colony stimulating factor production and/or release), up-regulation of molecules such as LFA-3, ICAM-1, CD154, CD69, CD25, or CD71 that mediate cell-cell interaction, and modulation of antibody secretion by B-cells. Assays for measuring these activities are well known in the art and have been described elsewhere herein.

In another embodiment of the invention methods are provided for identifying modulators of B7-like activity. The molecules that are identified can either inhibit the interaction of the B7-like molecules of the invention with their binding partners or interfere with intracellular signaling through their binding partners. These methods can be used once the known binding partner is identified as well as if its identity is unknown. In this manner new molecules can be identified that can modulate the activity of B7-like molecules of the invention, and are thus potentially useful as therapeutic agents for the diseases associated with B7-like activity as described elsewhere herein.

The methods of this embodiment of the invention take advantage of the biological activity of the B7-like molecules of the invention. As previously described herein, the ability of T-cells to synthesize cytokines depends not only on the primary activation signal provided by, for example, anti-CD3, phorbol ester, or by antigen in association with class II MHC to produce an activated T-cell, but also on the induction of a co-stimulatory signal, in this case, by interaction with a B7-like molecule of the invention. The binding of the B7-like molecules of the present invention to their natural binding partner (ICOS, PD-1, CD28, CTLA-4, or a related receptor) on, for example, an ICOS$^+$ T-cell, co-stimulates the T-cell and induces the production of increased levels of cytokines, particularly likely the production of interleukin-10 in this case, but may also include production of IL-2, IL-4, IL-5, interferon-gamma, tumor necrosis factor-alpha, or macrophage/granulocyte colony stimulating factor or other known or unknown cytokines. Cytokine production stimulates effects such as increased T-cell response to antigen, T-cell proliferation, T-cell differentiation, and T-cell and B-cell interactions. Assays for cytokines and T cell proliferation are known in the art and have been described elsewhere herein. Any of these assays can be utilized in this embodiment of the invention.

In this embodiment of the invention, the ability of a test molecule to inhibit the B7-like molecule's co-stimulatory activity is measured. B7-like co-stimulatory activity is measured as follows: T-cells expressing ICOS, PD-1, CD28, CTLA-4, or a related receptor are provided in vitro with a first or primary activation signal by anti-T3 monoclonal antibody (e.g. anti-CD3) or phorbol ester or, by antigen in association with class II MHC. B7-like molecule function is assayed by adding a source of B7-like protein of the invention (e.g., cells expressing a B7-like molecule or a fragment or variant thereof or a soluble form of a B7-like molecule such as a fusion protein as described herein). The B7-like activity that can be measured includes, but is not limited to, T-cell proliferation, modulation of cytokine production and/or release (such as IL-2, IL-4, IL-5, IL-10, interferon-gamma, tumor necrosis factor-alpha, or granulocyte/macrophage colony stimulating factor production and/or release), up-regulation of molecules such as LFA-3, ICAM-1, CD154, CD69, CD25, or CD71 that mediate cell-cell interaction, and modulation of antibody secretion by B-cells. A test molecule is included in this assay and its ability to decrease or inhibit any of the B7-activities described above is measured. In this manner, novel molecules with B7-like modulating activity can be identified.

In another embodiment, the above-described assay is modified such that the interference of a B7-like molecule binding to its binding partner is measured directly, rather than through measurement of a biological response as described above. As described in the previous embodiment, the source of the B7-like molecule can be cells expressing a B7-like molecule or a fragment or variant thereof, or a soluble form of a B7-like molecule such as a fusion protein as described elsewhere herein. The binding partner could also be provided in a soluble form such as in the form of a fusion protein, expressed on the surface of a cell, or bound to another matrix of choice. The ability of a test molecule to inhibit binding of the B7-like molecule to its binding partner is determined. Binding of the above-described molecules can be determined by a variety of methods, as such binding assays are well known in the art.

In one embodiment, the B7-like molecule of the invention is labeled with a radioisotope (methods for which are described elsewhere herein) and incubated with a binding partner provided in a soluble form such as in the form of a fusion protein, expressed on the surface of a cell, or bound to another matrix of choice. Quantification of the amount of complexed B7-like molecule of the invention and binding partner is measured by any number of standard assays known in the art. The ability of a test molecule to reduce the binding complex between the B7-like molecule of the invention and the binding partner is then measured by its inclusion in the assay.

In these assays it may be desirable to immobilize either a B7-like protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/B7-like fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the non-adsorbed binding partner or B7-like protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of B7-like binding or activity determined using standard techniques.

Other techniques for immobilizing proteins on matrices can also be used in the screening assays of the invention. For example, either B7-like protein or its target molecule can be immobilized utilizing conjugation of biotin and streptavidin. Biotinylated B7-like molecules or target molecules can be prepared from-biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a B7-like protein or target molecules but which do not interfere with binding of the B7-like protein to its target molecule can be derivatized to the wells of the plate, and unbound target or B7-like protein trapped in the wells by antibody conjugation. Methods for detecting such complexes, in addition to those described above for the GST-immobilized complexes, include immunodetection of complexes using antibodies reactive with the B7-like protein or binding partner, as well as enzyme-linked assays that rely on detecting an enzymatic activity associated with the B7-like protein or binding partner.

Once other natural binding partner(s) of the B7-like molecules of the present invention have been identified, the co-stimulation assay described previously herein can be used to screen for other molecules that possess B7-like activity. In this embodiment, T-cells that express the binding partner of a B7-like molecule are provided with a primary activation signal. These cells are then contacted with test molecules and the ability of the test molecule to provide a B7-like co-stimulatory signal is determined with an assay as described previously herein for any of the following activities: T-cell proliferation, modulation of cytokine production and/or release (such as IL-2, IL-4, IL-5, IL-10, interferon-gamma, tumor necrosis factor-alpha, or granulocyte/macrophage colony stimulating factor production and/or release), up-regulation of molecules such as LFA-3, ICAM-1, CD 154, CD69, CD25, or CD71that mediate cell-cell interaction, and modulation of antibody secretion by B-cells.

Confirmation that the B7-like activity elicited by a test molecule is due to interaction with the binding partner of the B7-like molecule of the invention can be obtained using a binding assay described previously herein. In this assay the B7-like molecule of the invention is labeled with a radio-isotope for detection and the ability of the test molecule to reduce the level of complexed B7-like protein and binding partner is measured. Specificity of the test molecule for a B7-like binding partner is indicated when the concentrations of test molecule necessary to elicit the measured biological response and to disrupt B7-like binding to its partner are similar.

In another embodiment, modulators of B7-like expression are identified in a method in which a cell that expresses a B7-like molecule is contacted with a candidate compound and the expression of B7-like mRNA or protein in the cell is determined relative to expression of B7-like mRNA or protein in a cell in the absence of the candidate compound. When expression is greater (statistically significantly greater) in the presence of the candidate compound than in its absence, the candidate compound is identified as a stimulator of B7-like mRNA or protein expression. Alternatively, when expression is less (statistically significantly less) in the presence of the candidate compound than in its absence, the candidate compound is identified as an inhibitor of B7-like mRNA or protein expression. The level of B7-like mRNA or protein expression in the cells can be determined by methods described herein for detecting B7-like mRNA or protein.

In yet another aspect of the invention, the B7-like proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with B7-like protein ("B7-like-binding proteins" or "B7-like-bp") and modulate B7-like activity. Such B7-like-binding proteins are also likely to be involved in the propagation of signals by the B7-like proteins as, for example, upstream or downstream elements of the B7-like pathway.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial B7-like gene sequences of the invention can be used to map their respective B7-like genes on a chromosome, thereby facilitating the location of gene regions associated with genetic disease. Computer analysis of B7-like sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the B7-like sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919–924). Somatic cell hybrids containing only fragments of human chromosomes can also be produced by using human chromosomes with translocations and deletions.

Other mapping strategies that can similarly be used to map a B7-like sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma eta a. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Another strategy to map the chromosomal location of B7-like genes uses B7-like polypeptides and fragments and sequences of the present invention and antibodies specific thereto. This mapping can be carried out by specifically detecting the presence of a B7-like polypeptide in members of a panel of somatic cell hybrids between cells of a first species of animal from which the protein originates and cells from a second species of animal, and then determining which somatic cell hybrid(s) expresses the polypeptide and noting the chromosomes(s) from the first species of animal that it contains. For examples of this technique, see Pajunen et al. (1988) *Cytogenet. Cell. Genet.* 47:37–41 and Van Keuren et al. (1986) *Hum. Genet.* 74:34–40. Alternatively, the presence of a B7-like polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the B7-like gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The B7-like sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described, e.g., in U.S. Pat. No. 5,272,057).

Furthermore, the sequences of the present invention can be used to provide an alternative technique for determining the actual base-by-base DNA sequence of selected portions of an individual's genome. Thus, the B7-like sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The B7-like sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO: 1 or SEQ ID NO:3 can comfortably provide positive individual identification with a panel of perhaps 10 to 1,000 primers that each yield a noncoding amplified sequence of 100 bases. If a predicted coding sequence, such as that in SEQ ID NO:1 or SEQ ID NO:3, is used, a more appropriate number of primers for positive individual identification would be 500 to 2,000.

3. Use of Partial B7-like Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO: 1 or SEQ ID NO:3 are particularly appropriate for this use as greater numbers of polymorphisms occur in the noncoding regions, making it easier to differentiate individuals using this technique. Examples of polynucleotide reagents include the B7-like sequences or portions thereof, e.g., fragments derived from the noncoding regions of SEQ ID NO: 1 or SEQ ID NO:3 having a length of at least 20 or 30 bases.

The B7-like sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such B7-like probes, can be used to identify tissue by species and/or by organ type.

In a similar fashion, these reagents, e.g., B7-like primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting B7-like protein and/or nucleic acid expression as well as B7-like activity, in the context of a biological sample. An exemplary method for detecting the presence or absence of B7-like proteins in a biological sample involves obtaining a biological sample from a test subject and contacting the biological sample with a compound or an agent capable of detecting B7-like protein or nucleic acid (e.g., mRNA, genomic DNA) that encodes B7-like protein such that the presence of B7-like protein is detected in the biological sample. Results obtained with a biological sample from the test subject may be compared to results obtained with a biological sample from a control subject.

A preferred agent for detecting B7-like mPNA or genomic DNA is a labeled nucleic acid probe capable of hybridizing to B7-like mRNA or genomic DNA. The nucleic acid probe can be, for example, a full-length B7-like nucleic acid, such as the nucleic acid of SEQ ID NO:1, SEQ ID NO:3, SEQ ID NO:27, or a portion thereof, such as a nucleic acid molecule of at least 25, 30, 50, 100, 250, or 500 nucleotides in length and sufficient to specifically hybridize under stringent conditions to B7-like mRNA or genomic DNA. Other suitable probes for use in the diagnostic assays of the invention are described herein.

A preferred agent for detecting B7-like protein is an antibody capable of binding to B7-like protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect B7-like mRNA, protein, or genomic DNA in a biological sample in vitro as well as in vivo. For example, in vitro techniques for detection of B7-like mRNA include Northern hybridizations and in situ hybridizations. In vitro techniques for detection of B7-like protein include enzyme linked immunosorbent assays (ELISAs), Western blots, immunoprecipitations, and immunofluorescence. In vitro techniques for detection of B7-like genomic DNA include Southern hybridizations. Furthermore, in vivo techniques for detection of B7-like protein include introducing into a subject a labeled anti-B7-like antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is one containing lymphocytes isolated from the affected tissue(s) and/or organ(s) of the test subject.

The invention also encompasses kits for detecting the presence of B7-like proteins in a biological sample (a test sample). Such kits can be used to determine if a subject is suffering from or is at increased risk of developing a disorder associated with aberrant expression of B7-like protein (e.g., an immunological or cell proliferative disorder). For example, the kit can comprise a labeled compound or agent capable of detecting B7-like protein or mRNA in a biological sample and means for determining the amount of a B7-like protein in the sample (e.g., an anti-B7-like antibody or an oligonucleotide probe that binds to DNA encoding a B7-like protein, e.g., SEQ ID NO:1, SEQ ID NO:3, or SEQ ID NO:27). Kits can also include instructions for observing that the tested subject is suffering from or is at risk of developing a disorder associated with aberrant expression of B7-like sequences if the amount of B7-like protein or mRNA is above or below a normal level.

For antibody-based kits, the kit can comprise, for example: (1) a first antibody (e.g., attached to a solid support) that binds to B7-like protein; and, optionally, (2) a second, different antibody that binds to B7-like protein or the first antibody and is conjugated to a detectable agent. For oligonucleotide-based kits, the kit can comprise, for example: (1) an oligonucleotide, e.g., a detectably labeled oligonucleotide, that hybridizes to a B7-like nucleic acid sequence or (2) a pair of primers useful for amplifying a B7-like nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of B7-like proteins.

2. Other Diagnostic Assays

In another aspect, the invention features a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a B7-like nucleic acid, preferably purified, polypeptide, preferably purified, or antibody, and thereby evaluating the plurality of capture probes. Binding, e.g., in the case of a nucleic acid, hybridization, with a capture probe at an address of the plurality, is detected, e.g., by signal generated from a label attached to the B7-like nucleic acid, polypeptide, or antibody. The capture probes can be a set of nucleic acids from a selected sample, e.g., a sample of nucleic acids derived from a control or non-stimulated tissue or cell.

The method can include contacting the B7-like nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of a B7-like sequence of the invention. Such methods can be used to diagnose a subject, e.g., to evaluate risk for a disease or disorder, to evaluate suitability of a selected treatment for a subject, to evaluate whether a subject has a disease or disorder. Thus, for example, the sequences set forth in SEQ ID NO:1, 3, and SEQ ID NO:27 encode B7-like polypeptides that are associated with the T cell response and, therefore, are useful for evaluating immune response disorders.

The method can be used to detect single nucleotide polymorphisms (SNPs), as described below.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express a B7-like polypeptide of the invention or from a cell or subject in which a B7-like-mediated response has been elicited, e.g., by contact of the cell with a B7-like nucleic acid or protein of the invention, or administration to the cell or subject a B7-like nucleic acid or protein of the invention; contacting the array with one or more inquiry probes, wherein an inquiry probe can be a nucleic acid, polypeptide, or antibody (which is preferably other than a B7-like nucleic acid, polypeptide, or antibody of the invention); providing a two dimensional array having a plurality of addresses, each address of the plurality being positionally distinguishable from each other address of the plurality, and each address of the plurality having a unique capture probe, e.g., wherein the capture probes are from a cell or subject which does not express a B7-like sequence of the invention (or does not express as highly as in the case of the B7-like positive plurality of capture probes) or from a cell or subject in which a B7-like-mediated response has not been elicited (or has been elicited to a lesser extent than in the first sample); contacting the array with one or more inquiry probes (which is preferably other than a B7-like nucleic acid, polypeptide, or antibody of the invention), and thereby evaluating the plurality of capture probes. Binding, e.g., in the case of a nucleic acid, hybridization, with a capture probe at an address of the plurality, is detected, e.g., by signal generated from a label attached to the nucleic acid, polypeptide, or antibody.

In another aspect, the invention features a method of analyzing a B7-like sequence of the invention, e.g., analyzing structure, function, or relatedness to other nucleic acid or amino acid sequences. The method includes: providing a B7-like nucleic acid or amino acid sequence, e.g., the sequence set forth in SEQ ID NO:1, SEQ ID NO:3, or SEQ ID NO:27, or a portion thereof; comparing the B7-like sequence with one or more preferably a plurality of sequences from a collection of sequences, e.g., a nucleic acid or protein sequence database; to thereby analyze the B7-like sequence of the invention.

The method can include evaluating the sequence identity between a B7-like sequence of the invention, e.g., the sequence, and a database sequence. The method can be performed by accessing the database at a second site, e.g., over the internet.

In another aspect, the invention features, a set of oligonucleotides, useful, e.g., for identifying SNP's, or identifying specific alleles of a B7-like sequence of the invention, e.g., the sequence. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

3. Prognostic Assays

The methods described herein can furthermore be utilized as diagnostic or prognostic assays to identify subjects having or at risk of developing a disease or disorder associated with B7-like protein, B7-like nucleic acid expression, or B7-like activity. Prognostic assays can be used for prognostic or predictive purposes to thereby prophylactically treat an individual prior to the onset of a disorder characterized by or associated with B7-like protein, B7-like nucleic acid expression, or B7-like activity.

Thus, the present invention provides a method in which a test sample is obtained from a subject, and B7-like protein or nucleic acid (e.g., mRNA, genomic DNA) is detected, wherein the presence of B7-like protein or nucleic acid is diagnostic for a subject having or at risk of developing a disease or disorder associated with aberrant B7-like expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease B7-like activity) to effectively treat a disease or disorder associated with aberrant B7-like expression or activity. In this manner, a test sample is obtained and B7-like protein or nucleic acid is detected. The presence of B7-like protein or nucleic acid is diagnostic for a subject that can be administered the agent to treat a disorder associated with aberrant B7-like expression or activity.

The methods of the invention can also be used to detect genetic lesions or mutations in a B7-like gene, thereby determining if a subject with the lesioned gene is at risk for a disorder characterized by aberrant immune response or cell proliferation. In preferred embodiments, the methods include detecting, in a sample of cells from the subject, the presence or absence of a genetic lesion or mutation characterized by at least one of an alteration affecting the integrity of a gene encoding a B7-like-protein, or the misexpression of the B7-like gene. For example, such genetic lesions or mutations can be detected by ascertaining the existence of at least one of: (1) a deletion of one or more nucleotides from a B7-like gene; (2) an addition of one or more nucleotides to a B7-like gene; (3) a substitution of one or more nucleotides of a B7-like gene; (4) a chromosomal rearrangement of a B7-like gene; (5) an alteration in the level of a messenger RNA transcript of a B7-like gene; (6) an aberrant modification of a B7-like gene, such as of the methylation pattern of the genomic DNA; (7) the presence of a non-wild-type splicing pattern of a messenger RNA transcript of a B7-like gene; (8) a non-wild-type level of a B7-like-protein; (9) an allelic loss of a B7-like gene; and (10) an inappropriate post-translational modification of a B7-like-protein. As described herein, there are a large number of assay techniques known in the art that can be used for detecting lesions in a B7-like gene. Any cell type or tissue, in which B7-like proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the B7-like-gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a B7-like gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a B7-like molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the B7-like gene and detect mutations by comparing the sequence of the sample B7-like gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the B7-like gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in B7-like cDNAs obtained from samples of cells. See, e.g., Hsu et al. (1994) *Carcinogenesis* 15:1657–1662.

According to an exemplary embodiment, a probe based on a B7-like sequence, e.g., a wild-type B7-like sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in B7-like genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving a B7-like gene.

4. Pharmacogenomics

Agents, or modulators that have a stimulatory or inhibitory effect on B7-like activity (e.g., B7-like gene expression) as identified by a screening assay described herein, can be administered to individuals to treat (prophylactically or therapeutically) disorders associated with aberrant B7-like activity as well as to modulate the phenotype of an immune response. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of B7-like protein, expression of B7-like nucleic acid, or mutation content of B7-like genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, an "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a B7-like protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a B7-like molecule or B7-like modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a B7-like molecule or B7-like modulator of the invention, such as a modulator identified by one of the exemplary screening assays described herein.

The present invention further provides methods for identifying new agents, or combinations, that are based on identifying agents that modulate the activity of one or more of the gene products encoded by one or more of the B7-like genes of the present invention, wherein these products may be associated with resistance of the cells to a therapeutic agent. Specifically, the activity of the proteins encoded by the B7-like genes of the present invention can be used as a basis for identifying agents for overcoming agent resistance. By blocking the activity of one or more of the resistance proteins, target cells will become sensitive to treatment with an agent that the unmodified target cells were resistant to.

Monitoring the influence of agents (e.g., drugs) on the expression or activity of a B7-like protein can be applied in clinical trials. For example, the effectiveness of an agent determined by a screening assay as described herein to increase B7-like gene expression, protein levels, or up-regulate B7-like activity, can be monitored in clinical trials of subjects exhibiting decreased B7-like gene expression, protein levels, or down-regulated B7-like activity. Alternatively, the effectiveness of an agent determined by a screening assay to decrease B7-like gene expression, protein levels, or down-regulate B7-like activity, can be monitored in clinical trials of subjects exhibiting increased B7-like gene expression, protein levels, or up-regulated B7-like activity. In such clinical trials, the expression or activity of a B7-like gene, and preferably, other genes that have been implicated in, for example, a B7-like-associated disorder can be used as a "read out" or markers of the phenotype of a particular cell.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of B7-like protein, expression of B7-like nucleic acid, or mutation content of B7-like genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a B7-like modulator, such as a modulator identified by one of the exemplary screening assays described herein.

5. Monitoring of Effects During Clinical Trials

Monitoring the influence of agents (e.g., drugs, compounds) on the expression or activity of B7-like genes (e.g., the ability to modulate aberrant immune response or cell proliferation) can be applied not only in basic drug screening but also in clinical trials. For example, the effectiveness of an agent, as determined by a screening assay as described herein, to increase or decrease B7-like gene expression, protein levels, or protein activity, can be monitored in clinical trials of subjects exhibiting decreased or increased B7-like gene expression, protein levels, or protein activity. In such clinical trials, B7-like expression or activity and preferably that of other genes that have been implicated in for example, a cellular proliferation disorder, can be used as a marker of the immune responsiveness of a particular cell.

For example, and not by way of limitation, genes that are modulated in cells by treatment with an agent (e.g., compound, drug, or small molecule) that modulates B7-like activity (e.g., as identified in a screening assay described herein) can be identified. Thus, to study the effect of agents on immune disorders, for example, in a clinical trial, cells can be isolated and RNA prepared and analyzed for the levels of expression of B7-like genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of B7-like genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a B7-like protein, mRNA, or genomic DNA in the preadministration sample; (3) obtaining one or more post-administration samples from the subject; (4) detecting the level of expression or activity of the B7-like protein, mRNA, or genomic DNA in the postadministration samples; (5) comparing the level of expression or activity of the B7-like protein, mRNA, or genomic DNA in the preadministration sample with the B7-like protein, mRNA, or genomic DNA in the postadministration sample or samples; and (vi) altering the administration of the agent to the subject accordingly to bring about the desired effect, i.e., for example, an increase or a decrease in the expression or activity of a B7-like protein.

C. Methods of Treatment

The present invention provides for both prophylactic and therapeutic methods of treating a subject at risk of (or susceptible to) a disorder or having a disorder associated with aberrant B7-like expression or activity. Additionally, the compositions of the invention find use in the treatment of disorders described herein. Thus, therapies for disorders associated with B7-like molecules are encompassed herein.

1. Prophylactic Methods

In one aspect, the invention provides a method for preventing in a subject a disease or condition associated with an aberrant B7-like expression or activity by administering to the subject an agent that modulates B7-like expression or at least one B7-like gene activity, and/or modulates the interaction of the abberrant B7-like molecule with its natural ligand, such as by administering an antibody that binds to the aberrant B7-like molecule thereby altering the binding of its natural ligand. Subjects at risk for a disease that is caused, or contributed to, by aberrant B7-like expression or activity can be identified by, for example, any or a combination of diagnostic or prognostic assays as described herein. Administration of a prophylactic agent can occur prior to the manifestation of symptoms characteristic of the B7-like aberrancy, such that a disease or disorder is prevented or, alternatively, delayed in its progression. Depending on the type of B7-like aberrancy, for example, a B7-like agonist or B7-like antagonist agent can be used for treating the subject. The appropriate agent can be determined based on screening assays described herein.

2. Therapeutic Methods

Another aspect of the invention pertains to methods of modulating B7-like expression or activity for therapeutic purposes. The modulatory method of the invention involves contacting a cell with an agent that modulates one or more of the activities of B7-like protein activity associated with the cell. An agent that modulates B7-like protein activity can be an agent as described herein, such as a nucleic acid or a protein, a naturally occurring cognate ligand of a B7-like protein, a peptide, a B7-like peptidomimetic, or other small molecule. In one embodiment, the agent stimulates one or more of the biological activities of B7-like protein. Examples of such stimulatory agents include active B7-like protein and a nucleic acid molecule encoding a B7-like protein that has been introduced into the cell. In another embodiment, the agent inhibits one or more of the biological activities of B7-like protein. Examples of such inhibitory agents include antisense B7-like nucleic acid molecules and anti-B7-like antibodies.

These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a B7-like protein or nucleic acid molecule, or a disease or disorder described herein. In one embodiment, the method involves administering an agent (e.g., an agent identified by a screening assay described herein), or a combination of agents, that modulates (e.g., up-regulates or down-regulates) B7-like expression or activity. In another embodiment, the method involves administering a B7-like protein or nucleic acid molecule as therapy to compensate for reduced or aberrant B7-like expression or activity.

Stimulation of B7-like activity is desirable in situations in which a B7-like protein is abnormally down-regulated and/or in which increased B7-like activity is likely to have a beneficial effect. For example, stimulation of PD-L activity in patients with Lupus-erythematosus is desirable, as transgenic mice in which expression of the receptor to which PD-L binds, PD-1, has been knocked out develop Lupus-like symptoms (Nishimura et al. (1999) *Immunity* 11:141–151). Conversely, inhibition of B7-like activity is desirable in situations in which B7-like activity is abnormally up-regulated and/or in which decreased B7-like activity is likely to have a beneficial effect. For example, interference of B7-like T-cell co-stimulation through CD28-like and/or CTLA-4-like receptors may be useful for the treatment of antibody-mediated autoimmune disease such as collagen-induced arthritis, dermatitis, and psoriasis *vulgaris* (Takiguchi et al. (1999) *Lab. Invest.* 79:317–326, Linsley et al. (1992) *Science* 257:792–795, Tada et al. (1999) *J. Immunol.* 162:203–208, Tang et al. (1996) *J. Immunol.* 157:117–125, Abrams et al. (1999) *J. Clin. Invest.* 103:1243–1252).

This invention is further illustrated by the following examples, which should not be construed as limiting.

EXPERIMENTAL

EXAMPLE 1

Isolation of hB7-H2 Long and hB7-H2 Short

The hB7-H2 long and hB7-H2 short sequences were identified in a human osteoblast library. The identified clones hB7-H21 and hB7-H2s encode transcripts of approximately 2.23 Kb and 1.98 Kb, and the corresponding cDNA's are set forth in SEQ ID NO:1 and SEQ ID NO:3, respectively. The open reading frames (nt 78–896 and 70–618) of these transcripts encode a predicted 273 amino acid protein (SEQ ID NO:2) and a 183 amino acid protein (SEQ ID NO:4) having a molecular weights of approximately 30.9 kDa and 20.8 kDa, respectively. The cDNA's, SEQ ID NO:1 and SEQ ID NO:3, are two different splice variants of the same gene. A search of the nucleotide and protein databases revealed that these cDNA's encode proteins belonging to the B7 family of immunoglobulins. The highest scoring blast hit that represented a human protein with known function at that time was human B7-H1 (Accession Number AAF25807.1; SEQ ID NO:8). The polypeptides set forth in SEQ ID NO:2 and SEQ ID NO:4, encoded by SEQ ID NO:1 and SEQ ID NO:3, respectively, were designated hB7-H2 long (hB7-H21) and hB7-H2 short (hB7-H2s) based on this homology. An alignment of all three of these protein sequences is shown in FIG. 9. The hB7-H21 protein (SEQ ID NO:2) shares approximately 37.4% identity to human B7-H1 (SEQ ID NO:8) (see FIG. 5), while hB7-H2s shares approximately 28.2% identity to hB7-H1 (see FIG. 6). The alignment was generated using the Clustal method with PAM250 residue weight table.

EXAMPLE 2 mRNA Expression of hB7-H2 Long

Northern blot analysis was performed for hB7-H2 long. Standard PCR protocol (i.e., (1) 95° C. for 1 min, (2) 95° C. for 1 min, (3) 55° C. for 1 min, (4) 72° C. for 1 min, (5) 72° C. for 5 min, (6) 14° C. forever, steps 2–4: 35 cycles) and the following primers were used to amplify the full-length open reading frame for hB7-H21:

hB7-H21 5' primer (SEQ ID NO:25):

5' CTCGAGGAATTCGCCGCC<u>ATGATCTTCCTCCTGCTAAT</u> 3' hB7-H21 3' primer (SEQ ID NO:26):

3' <u>GGGAAGTGAACAGTGCTATC</u>GCGGCCGCAAAAAA 5'

PCR products were run on a 1% agarose gel and bands were purified using the QIAEX-II kit. Sequence in bold is restriction enzyme sites. Sequence in italics is Kozak sequence. Sequence underlined represents those bases that match the ORF of the hB7-H2 gene of interest.

The Northern blot was done as follows. The probe was radiolabeled using $^{32}$PdCTP using standard procedures and hybridized to a Clonetech (Palo Alto, Calif.) human immune system multiple tissue northern (Catalogue #7768-1). This immune blot contains RNA from human spleen, lymph node, thymus, peripheral blood leukocyte, bone marrow and fetal liver. The hybridization and wash conditions used were as described in the Clontech Multiple Tissue Northern (MTN) Blot User Manual (Catalogue number PT1200-1). Kodak biomax film was exposed to the Northern blot membrane for 72 hours, which was then developed. An approximately 2.4 kb band was observed in all RNAs on the blot, the highest being in spleen and the lowest, which was nearly undetectable, in the peripheral blood leukocytes.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

---

SEQUENCE LISTING

```
<160> NUMBER OF SEQ ID NOS:  29

<210> SEQ ID NO 1
<211> LENGTH: 2229
<212> TYPE: DNA
<213> ORGANISM: Homo sapiens
<220> FEATURE:
<221> NAME/KEY: misc_feature
<222> LOCATION: (1)...(2229)
<223> OTHER INFORMATION: n = A,T,C or G
<221> NAME/KEY: CDS
<222> LOCATION: (78)...(896)
<221> NAME/KEY: misc_feature
<222> LOCATION: (1)...(2229)
<223> OTHER INFORMATION: B7-2H Long

<400> SEQUENCE: 1
tagggagtcg  acccacgcgt  ccgcttttgc  atctttactt  gtggagctgt  ggcaagtcct         60
catatcaaat  acagaac atg atc ttc ctc ctg cta atg ttg agc ctg gaa          110
                    Met Ile Phe Leu Leu Leu Met Leu Ser Leu Glu
                      1               5                  10 ttg cag ctt cac cag ata gca gct tta ttc aca gtg aca gtc cct aag         158
Leu Gln Leu His Gln Ile Ala Ala Leu Phe Thr Val Thr Val Pro Lys
             15                  20                  25 gaa ctg tac ata ata gag cat ggc agc aat gtg acc ctg gaa tgc aac         206
Glu Leu Tyr Ile Ile Glu His Gly Ser Asn Val Thr Leu Glu Cys Asn
         30                  35                  40 ttt gac act gga agt cat gtg aac ctt gga gca ata aca gcc agt ttg         254
Phe Asp Thr Gly Ser His Val Asn Leu Gly Ala Ile Thr Ala Ser Leu
     45                  50                  55 caa aag gtg gaa aat gat aca tcc cca cac cgt gaa aga gcc act ttg         302
Gln Lys Val Glu Asn Asp Thr Ser Pro His Arg Glu Arg Ala Thr Leu
 60                  65                  70                  75
```

```
ctg gag gag cag ctg ccc cta ggg aag gcc tcg ttc cac ata cct caa    350
Leu Glu Glu Gln Leu Pro Leu Gly Lys Ala Ser Phe His Ile Pro Gln
                 80                  85                  90 gtc caa gtg agg gac gaa gga cag tac caa tgc ata atc atc tat ggg    398
Val Gln Val Arg Asp Glu Gly Gln Tyr Gln Cys Ile Ile Ile Tyr Gly
                 95                 100                 105 gtc gcc tgg gac tac aag tac ctg act ctg aaa gtc aaa gct tcc tac    446
Val Ala Trp Asp Tyr Lys Tyr Leu Thr Leu Lys Val Lys Ala Ser Tyr
            110                 115                 120 agg aaa ata aac act cac atc cta aag gtt cca gaa aca gat gag gta    494
Arg Lys Ile Asn Thr His Ile Leu Lys Val Pro Glu Thr Asp Glu Val
        125                 130                 135 gag ctc acc tgc cag gct aca ggt tat cct ctg gca gaa gta tcc tgg    542
Glu Leu Thr Cys Gln Ala Thr Gly Tyr Pro Leu Ala Glu Val Ser Trp
140                 145                 150                 155 cca aac gtc agc gtt cct gcc aac acc agc cac tcc agg acc cct gaa    590
Pro Asn Val Ser Val Pro Ala Asn Thr Ser His Ser Arg Thr Pro Glu
                160                 165                 170 ggc ctc tac cag gtc acc agt gtt ctg cgc cta aag cca ccc cct ggc    638
Gly Leu Tyr Gln Val Thr Ser Val Leu Arg Leu Lys Pro Pro Pro Gly
            175                 180                 185 aga aac ttc agc tgt gtg ttc tgg aat act cac gtg agg gaa ctt act    686
Arg Asn Phe Ser Cys Val Phe Trp Asn Thr His Val Arg Glu Leu Thr
        190                 195                 200 ttg gcc agc att gac ctt caa agt cag atg gaa ccc agg acc cat cca    734
Leu Ala Ser Ile Asp Leu Gln Ser Gln Met Glu Pro Arg Thr His Pro
    205                 210                 215 act tgg ctg ctt cac att ttc atc ccc tcc tgc atc att gct ttc att    782
Thr Trp Leu Leu His Ile Phe Ile Pro Ser Cys Ile Ile Ala Phe Ile
220                 225                 230                 235 ttc ata gcc aca gtg ata gcc cta aga aaa caa ctc tgt caa aag ctg    830
Phe Ile Ala Thr Val Ile Ala Leu Arg Lys Gln Leu Cys Gln Lys Leu
                240                 245                 250 tat tct tca aaa gac aca aca aaa aga cct gtc acc aca aca aag agg    878
Tyr Ser Ser Lys Asp Thr Thr Lys Arg Pro Val Thr Thr Thr Lys Arg
            255                 260                 265 gaa gtg aac agt gct atc tgaacctgtg gtcttgggag ccagggtgac           926
Glu Val Asn Ser Ala Ile
        270 ctgatatgac atctaaagaa gcttctggac tctgaacaag aattcggtgg cctgcagagc   986 ttgccatttg cactttttcaa atgcctttgg atgacccagc actttaatct gaaacctgca  1046 acaagactag ccaacacctg gccatgaaac ttgccccttc actgatctgg actcacctct   1106 ggagcctatg gctttaagca agcactactg cactttacaa aattaccccca ctggatcctg   1166 gacccacaga attccttcag gatccttctt gctgccagac tgaaagcaaa aggaattatt   1226 tcccctcaag ttttctaagt gatttccaaa agcagaggtg tgtggaaatt tccagtaaca    1286 gaaacagatg ggttgccaat agagttattt tttatctata gcttcctctg ggtactagaa    1346 gaggctattg agactatgag ctcacagaca gggcttcgca caaactcaaa tcataattga    1406 catgttttat ggattactgg aatcttgata gcataatgaa gttgttctaa ttaacagaga    1466 gcatttaaat atacactaag tgcacaaatt gtggagtaaa gtcatcaagc tctgtttttg    1526 aggtctaagt cacaaagcat ttgttttaac ctgtaatggc accatgttta atggtggttt    1586 tttttttgaa cgacatcttt cctttaaaaa ttattggttt cttttttattt gttttttacct    1646 tagaaatcaa ttatatacag tcaaaaatat ttgatatgct catacgttgt atctgcagca    1706
```

```
atttcagata agtagctaaa atggccaaag ccccaaacta agcctccttt tctggccctc    1766
aatatgactt taaatttgac ttttcagtgc ctcagtttgc acatctgtaa tacagcaatg    1826
ctaagtagtc aaggcctttg ataattggca ctatggaaat cctgcaagat cccactacat    1886
atgtgtggag cagaagggta actcggctac agtaacagct taattttgtt aaatttgttc    1946
tttatactgg agccatgaag ctcagagcat tagctgaccc ttgaactatt caatgggca    2006 cattagctag tataacagac ttcataggt gggcctaaag caagctcctt aactgagcaa    2066
aatttggggc ttatgagaat gaagggtgt gaaattgact aacagacaaa tcatacatct    2126
cagtttctca attctcatgt aaatcagaga atgcctttaa agaataaaac tcaattgtta    2186
ttcttcaaaa aaaaaaaaaa aaaaaaaaaa aaaaagggn ggc                        2229
```

<210> SEQ ID NO 2
<211> LENGTH: 273
<212> TYPE: PRT
<213> ORGANISM: Homo sapiens

<400> SEQUENCE: 2

```
Met Ile Phe Leu Leu Met Leu Ser Leu Glu Leu Gln Leu His Gln
 1               5                  10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile
```

```
<210> SEQ ID NO 3
<211> LENGTH: 1975
<212> TYPE: DNA
<213> ORGANISM: Homo sapiens
<220> FEATURE:
<221> NAME/KEY: CDS
<222> LOCATION: (70)...(618)
<221> NAME/KEY: misc_feature
<222> LOCATION: (1)...(1975)
<223> OTHER INFORMATION: B7-2H Short

<400> SEQUENCE: 3
```

| | | |
|---|---|---:|
| ataggagtc gacccacgcg tccgctttac ttgtggagct gtggcaagtc ctcatatcaa | | 60 |
| atacagaac atg atc ttc ctc ctg cta atg ttg agc ctg gaa ttg cag ctt<br>          Met Ile Phe Leu Leu Leu Met Leu Ser Leu Glu Leu Gln Leu<br>            1               5                  10 | | 111 |
| cac cag ata gca gct tta ttc aca gtg aca gtc cct aag gaa ctg tac<br>His Gln Ile Ala Ala Leu Phe Thr Val Thr Val Pro Lys Glu Leu Tyr<br> 15              20                  25                  30 | | 159 |
| ata ata gag cat ggc agc aat gtg acc ctg gaa tgc aac ttt gac act<br>Ile Ile Glu His Gly Ser Asn Val Thr Leu Glu Cys Asn Phe Asp Thr<br>                 35                  40                  45 | | 207 |
| gga agt cat gtg aac ctt gga gca ata aca gcc agt ttg caa aag gtg<br>Gly Ser His Val Asn Leu Gly Ala Ile Thr Ala Ser Leu Gln Lys Val<br>             50                  55                  60 | | 255 |
| gaa aat gat aca tcc cca cac cgt gaa aga gcc act ttg ctg gag gag<br>Glu Asn Asp Thr Ser Pro His Arg Glu Arg Ala Thr Leu Leu Glu Glu<br> 65                  70                  75 | | 303 |
| cag ctg ccc cta ggg aag gcc tcg ttc cac ata cct caa gtc caa gtg<br>Gln Leu Pro Leu Gly Lys Ala Ser Phe His Ile Pro Gln Val Gln Val<br>             80                  85                  90 | | 351 |
| agg gac gaa gga cag tac caa tgc ata atc atc tat ggg gtc gcc tgg<br>Arg Asp Glu Gly Gln Tyr Gln Cys Ile Ile Ile Tyr Gly Val Ala Trp<br> 95                 100                 105                 110 | | 399 |
| gac tac aag tac ctg act ctg aaa gtc aaa ggt cag atg gaa ccc agg<br>Asp Tyr Lys Tyr Leu Thr Leu Lys Val Lys Gly Gln Met Glu Pro Arg<br>                115                 120                 125 | | 447 |
| acc cat cca act tgg ctg ctt cac att ttc atc ccc tcc tgc atc att<br>Thr His Pro Thr Trp Leu Leu His Ile Phe Ile Pro Ser Cys Ile Ile<br>             130                 135                 140 | | 495 |
| gct ttc att ttc ata gcc aca gtg ata gcc cta aga aaa caa ctc tgt<br>Ala Phe Ile Phe Ile Ala Thr Val Ile Ala Leu Arg Lys Gln Leu Cys<br>         145                 150                 155 | | 543 |
| caa aag ctg tat tct tca aaa gac aca aca aaa aga cct gtc acc aca<br>Gln Lys Leu Tyr Ser Ser Lys Asp Thr Thr Lys Arg Pro Val Thr Thr<br>     160                 165                 170 | | 591 |
| aca aag agg gaa gtg aac agt gct atc tgaacctgtg gtcttgggag<br>Thr Lys Arg Glu Val Asn Ser Ala Ile<br>175             180 | | 638 |
| ccagggtgac ctgatatgac atctaaagaa gcttctggac tctgaacaag aattcggtgg | | 698 |
| cctgcagagc ttgccatttg cacttttcaa atgcctttgg atgacccagc actttaatct | | 758 |
| gaaacctgca acaagactag ccaacacctg gccatgaaac ttgccccttc actgatctgg | | 818 |
| actcacctct ggagcctatg gctttaagca agcactactg cactttacag aattacccca | | 878 |
| ctggatcctg gacccacaga attccttcag gatccttctt gctgccagac tgaaagcaaa | | 938 |
| aggaattatt tcccctcaag ttttctaagt gatttccaaa agcagaggtg tgtggaaatt | | 998 |
| tccagtaaca gaaacagatg ggttgccaat agagttattt tttatctata gcttcctctg | | 1058 |
| ggtactagaa gaggctattg agactatgag ctcacagaca gggcttcgca caaactcaaa | | 1118 |

```
tcataattga catgttttat ggattactgg aatcttgata gcataatgaa gttgttctaa    1178
ttaacagaga gcatttaaat atacactaag tgcacaaatt gtggagtaaa gtcatcaagc    1238 tctgttttg  aggtctaagt cacaaagcat ttgttttaac ctgtaatggc accatgttta    1298
atggtggttt ttttttttgaa ctacatcttt cctttaaaaa ttattggttt ctttttattt   1358
gtttttacct tagaaatcaa ttatatacag tcaaaaatat ttgatatgct catacgttgt    1418
atctgcagca atttcagata agtagctaaa atggccaaag ccccaaacta agcctccttt    1478
tctggccctc aatatgactt taaatttgac ttttcagtgc ctcagtttgc acatctgtaa    1538
tacagcaatg ctaagtagtc aaggcctttg ataattggca ctatggaaat cctgcaagat    1598
cccactacat atgtgtggag cagaagggta actcggctac agtaacagct taattttgtt    1658
aaatttgttc tttatactgg agccatgaag ctcagagcat tagctgaccc ttgaactatt    1718
caaatgggca cattagctag tataacagac ttacataggt gggcctaaag caagctcctt    1778
aactgagcaa aatttggggc ttatgagaat gaagggtgt  gaaattgact aacagacaaa    1838
tcatacatct cagtttctca attctcatgt aaatcagaga atgcctttaa agaataaaac    1898
tcaattgtta ttcttcaaaa aaaaaaaaaa aaaaaaaaa  aaagggcggc cgctagacta    1958
gtctagagaa aaaacct                                                   1975

<210> SEQ ID NO 4
<211> LENGTH: 183
<212> TYPE: PRT
<213> ORGANISM: Homo sapiens

<400> SEQUENCE: 4

Met Ile Phe Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Gly Gln Met Glu Pro Arg Thr His
        115                 120                 125

Pro Thr Trp Leu Leu His Ile Phe Ile Pro Ser Cys Ile Ile Ala Phe
    130                 135                 140

Ile Phe Ile Ala Thr Val Ile Ala Leu Arg Lys Gln Leu Cys Gln Lys
145                 150                 155                 160

Leu Tyr Ser Ser Lys Asp Thr Thr Lys Arg Pro Val Thr Thr Thr Lys
                165                 170                 175

Arg Glu Val Asn Ser Ala Ile
            180

<210> SEQ ID NO 5
<211> LENGTH: 288
<212> TYPE: PRT
```

<213> ORGANISM: Homo sapiens

<400> SEQUENCE: 5

```
Met Gly His Thr Arg Arg Gln Gly Thr Ser Pro Ser Lys Cys Pro Tyr
 1               5                  10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
        50                  55                  60

Tyr Trp Gln Lys Glu Lys Lys Met Val Leu Thr Met Met Ser Gly Asp
 65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
               100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
        130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285
```

<210> SEQ ID NO 6
<211> LENGTH: 324
<212> TYPE: PRT
<213> ORGANISM: Homo sapiens

<400> SEQUENCE: 6

```
Met Gly Leu Ser Asn Ile Leu Phe Val Met Ala Phe Leu Leu Ser Gly
 1               5                  10                  15

Ala Ala Pro Leu Lys Ile Gln Ala Tyr Phe Asn Glu Thr Ala Asp Leu
                20                  25                  30

Pro Cys Gln Phe Ala Asn Ser Gln Asn Gln Ser Leu Ser Glu Leu Val
            35                  40                  45

Val Phe Trp Gln Asp Gln Glu Asn Leu Val Leu Asn Glu Val Tyr Leu
        50                  55                  60

Gly Lys Glu Lys Phe Asp Ser Val His Ser Lys Tyr Met Gly Arg Thr
```

```
            65                  70                  75                  80
Ser Phe Asp Ser Asp Ser Trp Thr Leu Arg Leu His Asn Leu Gln Ile
                85                  90                  95

Lys Asp Lys Gly Leu Tyr Gln Cys Ile Ile His Lys Lys Pro Thr
                100                 105                 110

Gly Met Ile Arg Ile His Gln Met Asn Ser Glu Leu Ser Val Leu Ala
                115                 120                 125

Asn Phe Ser Gln Pro Glu Ile Val Pro Ile Ser Asn Ile Thr Glu Asn
130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
                180                 185                 190

Val Ser Ile Ser Leu Ser Val Ser Phe Pro Asp Val Thr Ser Asn Met
                195                 200                 205

Thr Ile Phe Cys Ile Leu Glu Thr Asp Lys Thr Arg Leu Leu Ser Ser
                210                 215                 220

Pro Phe Ser Ile Glu Leu Glu Asp Pro Gln Pro Pro Asp His Ile
225                 230                 235                 240

Pro Trp Ile Thr Ala Val Leu Pro Thr Val Ile Ile Cys Val Met Val
                245                 250                 255

Phe Pro Cys Leu Ile Leu Trp Lys Trp Lys Lys Lys Arg Pro Arg
                260                 265                 270

Asn Ser Tyr Lys Cys Gly Thr Asn Thr Met Glu Arg Glu Glu Ser Glu
                275                 280                 285

Gln Thr Lys Lys Arg Glu Lys Ile His Ile Pro Glu Arg Ser Asp Glu
                290                 295                 300

Ala Gln Arg Val Phe Lys Ser Ser Lys Thr Ser Ser Cys Asp Lys Ser
305                 310                 315                 320

Asp Thr Cys Phe

<210> SEQ ID NO 7
<211> LENGTH: 309
<212> TYPE: PRT
<213> ORGANISM: Homo sapiens

<400> SEQUENCE: 7

Met Arg Leu Gly Ser Pro Gly Leu Leu Phe Leu Leu Phe Ser Ser Leu
 1               5                  10                  15

Arg Ala Asp Thr Gln Glu Lys Glu Val Arg Ala Met Val Gly Ser Asp
                20                  25                  30

Val Glu Leu Ser Cys Ala Cys Pro Glu Gly Ser Arg Phe Asp Leu Asn
                35                  40                  45

Asp Val Tyr Val Tyr Trp Gln Thr Ser Glu Ser Lys Thr Val Val Thr
                50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
                100                 105                 110

Cys Leu Val Leu Ser Gln Ser Leu Gly Phe Gln Glu Val Leu Ser Val
```

-continued

```
            115                 120                 125
Glu Val Thr Leu His Val Ala Ala Asn Phe Ser Val Pro Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Val Val Val Ala Val Ala
            260                 265                 270

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Glu Ser Trp Asn Leu
    290                 295                 300

Leu Leu Leu Ser
305

<210> SEQ ID NO 8
<211> LENGTH: 290
<212> TYPE: PRT
<213> ORGANISM: Homo sapiens

<400> SEQUENCE: 8

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175
```

```
Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                    245                 250                 255

Phe Ile Phe Arg Leu Arg Lys Gly Arg Met Met Asp Val Lys Lys Cys
                    260                 265                 270

Gly Ile Gln Asp Thr Asn Ser Lys Lys Gln Ser Asp Thr His Leu Glu
                    275                 280                 285

Glu Thr
    290

<210> SEQ ID NO 9
<211> LENGTH: 526
<212> TYPE: PRT
<213> ORGANISM: Homo sapiens

<400> SEQUENCE: 9

Met Ala Val Phe Pro Ser Ser Gly Leu Pro Arg Cys Leu Leu Thr Leu
1               5                   10                  15

Ile Leu Leu Gln Leu Pro Lys Leu Asp Ser Ala Pro Phe Asp Val Ile
                20                  25                  30

Gly Pro Pro Glu Pro Ile Leu Ala Val Val Gly Glu Asp Ala Glu Leu
            35                  40                  45

Pro Cys Arg Leu Ser Pro Asn Ala Ser Ala Glu His Leu Glu Leu Arg
        50                  55                  60

Trp Phe Arg Lys Lys Val Ser Pro Ala Val Leu Val His Arg Asp Gly
65                  70                  75                  80

Arg Glu Gln Glu Ala Glu Gln Met Pro Glu Tyr Arg Gly Arg Ala Thr
                85                  90                  95

Leu Val Gln Asp Gly Ile Ala Lys Gly Arg Val Ala Leu Arg Ile Arg
            100                 105                 110

Gly Val Arg Val Ser Asp Asp Gly Glu Tyr Thr Cys Phe Phe Arg Glu
        115                 120                 125

Asp Gly Ser Tyr Glu Glu Ala Leu Val His Leu Lys Val Ala Ala Leu
130                 135                 140

Gly Ser Asp Pro His Ile Ser Met Gln Val Gln Glu Asn Gly Glu Ile
145                 150                 155                 160

Cys Leu Glu Cys Thr Ser Val Gly Trp Tyr Pro Glu Pro Gln Val Gln
                165                 170                 175

Trp Arg Thr Ser Lys Gly Glu Lys Phe Pro Ser Thr Ser Glu Ser Arg
            180                 185                 190

Asn Pro Asp Glu Glu Gly Leu Phe Thr Val Ala Ala Ser Val Ile Ile
        195                 200                 205

Arg Asp Thr Ser Thr Lys Asn Val Ser Cys Tyr Ile Gln Asn Leu Leu
    210                 215                 220

Leu Gly Gln Glu Lys Lys Val Glu Ile Ser Ile Pro Ala Ser Ser Leu
225                 230                 235                 240

Pro Arg Leu Thr Pro Trp Ile Val Ala Val Ala Val Ile Leu Met Val
                245                 250                 255
```

```
Leu Gly Leu Leu Thr Ile Gly Ser Ile Phe Phe Thr Trp Arg Leu Tyr
            260                 265                 270

Asn Glu Arg Pro Arg Glu Arg Asn Glu Phe Ser Ser Lys Glu Arg
        275                 280                 285

Leu Leu Glu Glu Leu Lys Trp Lys Lys Ala Thr Leu His Ala Val Asp
        290                 295                 300

Val Thr Leu Asp Pro Asp Thr Ala His Pro His Leu Phe Leu Tyr Glu
305                 310                 315                 320

Asp Ser Lys Ser Val Arg Leu Glu Asp Ser Arg Gln Lys Leu Pro Glu
                325                 330                 335

Lys Thr Glu Arg Phe Asp Ser Trp Pro Cys Val Leu Gly Arg Glu Thr
            340                 345                 350

Phe Thr Ser Gly Arg His Tyr Trp Glu Val Glu Val Gly Asp Arg Thr
            355                 360                 365

Asp Trp Ala Ile Gly Val Cys Arg Glu Asn Val Met Lys Lys Gly Phe
370                 375                 380

Asp Pro Met Thr Pro Glu Asn Gly Phe Trp Ala Val Glu Leu Tyr Gly
385                 390                 395                 400

Asn Gly Tyr Trp Ala Leu Thr Pro Leu Arg Thr Pro Leu Pro Leu Ala
                405                 410                 415

Gly Pro Pro Arg Arg Val Gly Ile Phe Leu Asp Tyr Glu Ser Gly Asp
                420                 425                 430

Ile Ser Phe Tyr Asn Met Asn Asp Gly Ser Asp Ile Tyr Thr Phe Ser
            435                 440                 445

Asn Val Thr Phe Ser Gly Pro Leu Arg Pro Phe Phe Cys Leu Trp Ser
450                 455                 460

Ser Gly Lys Lys Pro Leu Thr Ile Cys Pro Ile Ala Asp Gly Pro Glu
465                 470                 475                 480

Arg Val Thr Val Ile Ala Asn Ala Gln Asp Leu Ser Lys Glu Ile Pro
                485                 490                 495

Leu Ser Pro Met Gly Glu Glu Ser Ala Pro Arg Asp Ala Asp Thr Leu
            500                 505                 510

His Ser Lys Leu Ile Pro Thr Gln Pro Ser Gln Gly Ala Pro
            515                 520                 525

<210> SEQ ID NO 10
<211> LENGTH: 527
<212> TYPE: PRT
<213> ORGANISM: Homo sapiens

<400> SEQUENCE: 10

Met Glu Ser Ala Ala Ala Leu His Phe Ser Arg Pro Ala Ser Leu Leu
 1               5                  10                  15

Leu Leu Leu Leu Ser Leu Cys Ala Leu Val Ser Ala Gln Phe Ile Val
                20                  25                  30

Val Gly Pro Thr Asp Pro Ile Leu Ala Thr Val Gly Glu Asn Thr Thr
            35                  40                  45

Leu Arg Cys His Leu Ser Pro Glu Lys Asn Ala Glu Asp Met Glu Val
        50                  55                  60

Arg Trp Phe Arg Ser Gln Phe Ser Pro Ala Val Phe Val Tyr Lys Gly
65                  70                  75                  80

Gly Arg Glu Arg Thr Glu Glu Gln Met Glu Glu Tyr Arg Gly Arg Thr
                85                  90                  95

Thr Phe Val Ser Lys Asp Ile Ser Arg Gly Ser Val Ala Leu Val Ile
```

```
              100                 105                 110
His Asn Ile Thr Ala Gln Glu Asn Gly Thr Tyr Arg Cys Tyr Phe Gln
            115                 120                 125

Glu Gly Arg Ser Tyr Asp Glu Ala Ile Leu His Leu Val Val Ala Gly
            130                 135                 140

Leu Gly Ser Lys Pro Leu Ile Ser Met Arg Gly His Glu Asp Gly Gly
145                 150                 155                 160

Ile Arg Leu Glu Cys Ile Ser Arg Gly Trp Tyr Pro Lys Pro Leu Thr
                165                 170                 175

Val Trp Arg Asp Pro Tyr Gly Gly Val Ala Pro Ala Leu Lys Glu Val
            180                 185                 190

Ser Met Pro Asp Ala Asp Gly Leu Phe Met Val Thr Thr Ala Val Ile
            195                 200                 205

Ile Arg Asp Lys Ser Val Arg Asn Met Ser Cys Ser Ile Asn Asn Thr
210                 215                 220

Leu Leu Gly Gln Lys Lys Glu Ser Val Ile Phe Ile Pro Glu Ser Phe
225                 230                 235                 240

Met Pro Ser Val Ser Pro Cys Ala Val Ala Leu Pro Ile Ile Val Val
                245                 250                 255

Ile Leu Met Ile Pro Ile Ala Val Cys Ile Tyr Trp Ile Asn Lys Leu
            260                 265                 270

Gln Lys Glu Lys Lys Ile Leu Ser Gly Glu Lys Glu Phe Glu Arg Glu
            275                 280                 285

Thr Arg Glu Ile Ala Leu Lys Glu Leu Glu Lys Glu Arg Val Gln Lys
            290                 295                 300

Glu Glu Glu Leu Gln Val Lys Glu Lys Leu Gln Glu Glu Leu Arg Trp
305                 310                 315                 320

Arg Arg Thr Phe Leu His Ala Val Asp Val Val Leu Asp Pro Asp Thr
                325                 330                 335

Ala His Pro Asp Leu Phe Leu Ser Glu Asp Arg Arg Ser Val Arg Arg
            340                 345                 350

Cys Pro Phe Arg His Leu Gly Glu Ser Val Pro Asp Asn Pro Glu Arg
            355                 360                 365

Phe Asp Ser Gln Pro Cys Val Leu Gly Arg Glu Ser Phe Ala Ser Gly
370                 375                 380

Lys His Tyr Trp Glu Val Glu Val Glu Asn Val Ile Glu Trp Thr Val
385                 390                 395                 400

Gly Val Cys Arg Asp Ser Val Glu Arg Lys Gly Glu Val Leu Leu Ile
                405                 410                 415

Pro Gln Asn Gly Phe Trp Thr Leu Glu Met His Lys Gly Gln Tyr Arg
            420                 425                 430

Ala Val Ser Ser Pro Asp Arg Ile Leu Pro Leu Lys Glu Ser Leu Cys
            435                 440                 445

Arg Val Gly Val Phe Leu Asp Tyr Glu Ala Gly Asp Val Ser Phe Tyr
450                 455                 460

Asn Met Arg Asp Arg Ser His Ile Tyr Thr Cys Pro Arg Ser Ala Phe
465                 470                 475                 480

Ser Val Pro Val Arg Pro Phe Phe Arg Leu Gly Cys Glu Asp Ser Pro
                485                 490                 495

Ile Phe Ile Cys Pro Ala Leu Thr Gly Ala Asn Gly Val Thr Val Pro
            500                 505                 510

Glu Glu Gly Leu Thr Leu His Arg Val Gly Thr His Gln Ser Leu
            515                 520                 525
```

```
<210> SEQ ID NO 11
<211> LENGTH: 523
<212> TYPE: PRT
<213> ORGANISM: Homo sapiens

<400> SEQUENCE: 11

Met Glu Pro Ala Ala Ala Leu His Phe Ser Leu Pro Ala Ser Leu Leu
 1               5                  10                  15

Leu Leu Leu Leu Leu Leu Leu Leu Ser Leu Cys Ala Leu Val Ser Ala
            20                  25                  30

Gln Phe Thr Val Val Gly Pro Ala Asn Pro Ile Leu Ala Met Val Gly
            35                  40                  45

Glu Asn Thr Thr Leu Arg Cys His Leu Ser Pro Glu Lys Asn Ala Glu
 50                  55                  60

Asp Met Glu Val Arg Trp Phe Arg Ser Gln Phe Ser Pro Ala Val Phe
 65                  70                  75                  80

Val Tyr Lys Gly Gly Arg Glu Arg Thr Glu Glu Gln Met Glu Glu Tyr
                 85                  90                  95

Arg Gly Arg Ile Thr Phe Val Ser Lys Asp Ile Asn Arg Gly Ser Val
            100                 105                 110

Ala Leu Val Ile His Asn Val Thr Ala Gln Glu Asn Gly Ile Tyr Arg
            115                 120                 125

Cys Tyr Phe Gln Glu Gly Arg Ser Tyr Asp Glu Ala Ile Leu Arg Leu
130                 135                 140

Val Val Ala Gly Leu Gly Ser Lys Pro Leu Ile Glu Ile Lys Ala Gln
145                 150                 155                 160

Glu Asp Gly Ser Ile Trp Leu Glu Cys Ile Ser Gly Gly Trp Tyr Pro
                165                 170                 175

Glu Pro Leu Thr Val Trp Arg Asp Pro Tyr Gly Glu Val Val Pro Ala
            180                 185                 190

Leu Lys Glu Val Ser Ile Ala Asp Ala Asp Gly Leu Phe Met Val Thr
            195                 200                 205

Thr Ala Val Ile Ile Arg Asp Lys Tyr Val Arg Asn Val Ser Cys Ser
    210                 215                 220

Val Asn Asn Thr Leu Leu Gly Gln Glu Lys Glu Thr Val Ile Phe Ile
225                 230                 235                 240

Pro Glu Ser Phe Met Pro Ser Ala Ser Pro Trp Met Val Ala Leu Ala
                245                 250                 255

Val Ile Leu Thr Ala Ser Pro Trp Met Val Ser Met Thr Val Ile Leu
            260                 265                 270

Ala Val Phe Ile Ile Phe Met Ala Val Ser Ile Cys Cys Ile Lys Lys
            275                 280                 285

Leu Gln Arg Glu Lys Lys Ile Leu Ser Gly Glu Lys Lys Val Glu Gln
        290                 295                 300

Glu Glu Lys Glu Ile Ala Gln Gln Leu Gln Glu Glu Leu Arg Trp Arg
305                 310                 315                 320

Arg Thr Phe Leu His Ala Ala Asp Val Val Leu Asp Pro Asp Thr Ala
                325                 330                 335

His Pro Glu Leu Phe Leu Ser Glu Asp Arg Arg Ser Val Arg Arg Gly
            340                 345                 350

Pro Tyr Arg Gln Arg Val Pro Asp Asn Pro Glu Arg Phe Asp Ser Gln
            355                 360                 365

Pro Cys Val Leu Gly Trp Glu Ser Phe Ala Ser Gly Lys His Tyr Trp
```

```
            370                 375                 380
Glu Val Glu Val Glu Asn Val Met Val Trp Thr Val Gly Val Cys Arg
385                 390                 395                 400

His Ser Val Glu Arg Lys Gly Glu Val Leu Leu Ile Pro Gln Asn Gly
                405                 410                 415

Phe Trp Thr Leu Glu Met Phe Gly Asn Gln Tyr Arg Ala Leu Ser Ser
                420                 425                 430

Pro Glu Arg Ile Leu Pro Leu Lys Glu Ser Leu Cys Arg Val Gly Val
                435                 440                 445

Phe Leu Asp Tyr Glu Ala Gly Asp Val Ser Phe Tyr Asn Met Arg Asp
            450                 455                 460

Arg Ser His Ile Tyr Thr Cys Pro Arg Ser Ala Phe Thr Val Pro Val
465                 470                 475                 480

Arg Pro Phe Phe Arg Leu Gly Ser Asp Asp Ser Pro Ile Phe Ile Cys
                485                 490                 495

Pro Ala Leu Thr Gly Ala Ser Gly Val Met Val Pro Glu Glu Gly Leu
                500                 505                 510

Lys Leu His Arg Val Gly Thr His Gln Ser Leu
                515                 520

<210> SEQ ID NO 12
<211> LENGTH: 319
<212> TYPE: PRT
<213> ORGANISM: Homo sapiens

<400> SEQUENCE: 12

Met Lys Met Ala Ser Ser Leu Ala Phe Leu Leu Leu Asn Phe His Val
1               5                   10                  15

Ser Leu Leu Leu Val Gln Leu Leu Thr Pro Cys Ser Ala Gln Phe Ser
                20                  25                  30

Val Leu Gly Pro Ser Gly Pro Ile Leu Ala Met Val Gly Glu Asp Ala
                35                  40                  45

Asp Leu Pro Cys His Leu Phe Pro Thr Met Ser Ala Glu Thr Met Glu
            50                  55                  60

Leu Lys Trp Val Ser Ser Ser Leu Arg Gln Val Val Asn Val Tyr Ala
65                  70                  75                  80

Asp Gly Lys Glu Val Glu Asp Arg Gln Ser Ala Pro Tyr Arg Gly Arg
                85                  90                  95

Thr Ser Ile Leu Arg Asp Gly Ile Thr Ala Gly Lys Ala Ala Leu Arg
                100                 105                 110

Ile His Asn Val Thr Ala Ser Asp Ser Gly Lys Tyr Leu Cys Tyr Phe
                115                 120                 125

Gln Asp Gly Asp Phe Tyr Glu Lys Ala Leu Val Glu Leu Lys Val Ala
            130                 135                 140

Ala Leu Gly Ser Asn Leu His Val Glu Val Lys Gly Tyr Glu Asp Gly
145                 150                 155                 160

Gly Ile His Leu Glu Cys Arg Ser Thr Gly Trp Tyr Pro Gln Pro Gln
                165                 170                 175

Ile Gln Trp Ser Asn Ala Lys Gly Glu Asn Ile Pro Ala Val Glu Ala
                180                 185                 190

Pro Val Val Ala Asp Gly Val Gly Leu Tyr Glu Val Ala Ala Ser Val
                195                 200                 205

Ile Met Arg Gly Gly Ser Gly Glu Gly Val Ser Cys Ile Ile Arg Asn
                210                 215                 220
```

```
Ser Leu Leu Gly Leu Glu Lys Thr Ala Ser Ile Ser Ile Ala Asp Pro
225                 230                 235                 240

Phe Phe Arg Ser Ala Gln Pro Trp Ile Ala Ala Leu Ala Gly Thr Leu
            245                 250                 255

Pro Ile Leu Leu Leu Leu Leu Ala Gly Ala Ser Tyr Phe Leu Trp Arg
                260                 265                 270

Gln Gln Lys Glu Ile Thr Ala Leu Ser Ser Glu Ile Glu Ser Glu Gln
            275                 280                 285

Glu Met Lys Glu Met Gly Tyr Ala Ala Thr Arg Glu Ile Ser Leu
290                 295                 300

Arg Glu Ser Leu Gln Glu Glu Leu Lys Arg Lys Lys Ser Ser Thr
305                 310                 315

<210> SEQ ID NO 13
<211> LENGTH: 529
<212> TYPE: PRT
<213> ORGANISM: Homo sapiens

<400> SEQUENCE: 13

Met Glu Ser Ala Ala Ala Leu His Phe Ser Arg Pro Ala Ser Leu Leu
1               5                   10                  15

Leu Leu Leu Leu Ser Leu Cys Ala Leu Val Ser Ala His Phe Ile Val
                20                  25                  30

Val Gly Pro Thr Asp Pro Ile Leu Ala Thr Val Gly Glu Asn Thr Thr
            35                  40                  45

Leu Arg Cys His Leu Ser Pro Glu Lys Asn Ala Glu Asp Met Glu Val
    50                  55                  60

Arg Trp Phe Arg Ser Gln Phe Ser Pro Ala Val Phe Val Tyr Lys Gly
65                  70                  75                  80

Gly Arg Glu Arg Thr Glu Glu Gln Met Glu Glu Tyr Arg Gly Arg Thr
                85                  90                  95

Thr Phe Val Ser Lys Asp Ile Ser Arg Gly Ser Val Ala Leu Val Ile
            100                 105                 110

His Asn Ile Thr Ala Gln Gly Asn Gly Thr Tyr Arg Cys Tyr Phe Gln
    115                 120                 125

Glu Gly Arg Ser Tyr Asp Glu Ala Ile Leu His Leu Val Val Ala Glu
130                 135                 140

Arg Leu Gly Ser Lys Pro Leu Ile Ser Met Arg Gly His Glu Asp Gly
145                 150                 155                 160

Gly Ile Arg Leu Glu Cys Ile Ser Arg Gly Trp Tyr Pro Lys Pro Leu
                165                 170                 175

Thr Val Trp Arg Asp Pro Tyr Gly Gly Val Ala Pro Ala Leu Lys Glu
            180                 185                 190

Val Ser Met Pro Asp Ala Asp Gly Leu Phe Met Val Thr Thr Ala Val
    195                 200                 205

Ile Ile Arg Asp Lys Ser Val Arg Asn Met Ser Cys Ser Ile Asn Asn
210                 215                 220

Thr Leu Leu Gly Gln Lys Lys Glu Ser Val Ile Phe Ile Pro Glu Ser
225                 230                 235                 240

Phe Met Pro Ser Val Ser Pro Leu Ala Val Cys Ile Tyr Trp Ile Asn
            245                 250                 255

Lys Leu Gln Lys Glu Lys Lys Ile Leu Ser Gly Glu Lys Glu Phe Glu
                260                 265                 270

Arg Glu Thr Arg Glu Ile Ala Leu Lys Glu Leu Glu Lys Glu Arg Val
            275                 280                 285
```

```
Gln Lys Glu Glu Leu Gln Val Lys Glu Lys Leu Gln Glu Glu Leu
    290                 295                 300

Arg Trp Arg Arg Thr Phe Leu His Ala Val Asp Val Leu Asp Pro
305                 310                 315                 320

Asp Thr Ala His Pro Asp Leu Phe Leu Ser Glu Asp Arg Arg Ser Val
                325                 330                 335

Arg Arg Cys Pro Phe Arg His Leu Gly Glu Ser Val Pro Asp Asn Pro
                340                 345                 350

Glu Arg Phe Asp Ser Gln Pro Cys Val Leu Gly Arg Glu Ser Phe Ala
            355                 360                 365

Ser Gly Lys His Tyr Trp Glu Val Glu Val Asn Val Ile Glu Trp
    370                 375                 380

Thr Val Gly Val Cys Arg Asp Ser Val Glu Arg Lys Gly Glu Val Leu
385                 390                 395                 400

Leu Ile Pro Gln Asn Gly Phe Trp Thr Leu Glu Met His Lys Gly Gln
                405                 410                 415

Tyr Arg Ala Val Ser Ser Pro Asp Arg Ile Leu Pro Leu Lys Glu Ser
                420                 425                 430

Leu Cys Arg Val Gly Val Phe Leu Asp Tyr Glu Ala Gly Asp Val Ser
            435                 440                 445

Phe Tyr Asn Met Arg Asp Arg Ser His Ile Tyr Thr Cys Pro Arg Ser
    450                 455                 460

Ala Phe Ser Gly Pro Asp Thr Ser Gln Ser Gly Asp Pro Glu Pro
465                 470                 475                 480

Ile Glu Ser Ile Pro Trp Ser His Ser His Val Asp Lys Pro Trp Ser
                485                 490                 495

Phe Gln Gln Pro Pro His Asn Thr His Leu Pro Ala Ala Ser Phe Thr
                500                 505                 510

Pro Thr Thr Asp Leu Ser Pro Ser Phe Leu Leu Leu Thr Arg Leu Cys
            515                 520                 525

Phe

<210> SEQ ID NO 14
<211> LENGTH: 357
<212> TYPE: PRT
<213> ORGANISM: Homo sapiens

<400> SEQUENCE: 14

Met Ala Ser Ser Leu Ala Phe Leu Leu Leu Asn Phe His Val Ser Leu
1               5                   10                  15

Leu Leu Val Gln Leu Leu Thr Pro Cys Ser Ala Gln Phe Ser Val Leu
                20                  25                  30

Gly Pro Ser Gly Pro Ile Leu Ala Met Val Gly Glu Asp Ala Asp Leu
            35                  40                  45

Pro Cys His Leu Phe Pro Thr Met Ser Ala Glu Thr Met Glu Leu Lys
    50                  55                  60

Trp Val Ser Ser Ser Leu Arg Gln Val Val Asn Val Tyr Ala Asp Gly
65              70                  75                  80

Lys Glu Val Glu Asp Arg Gln Ser Ala Pro Tyr Arg Gly Arg Thr Ser
                85                  90                  95

Ile Leu Arg Asp Gly Ile Thr Ala Gly Lys Ala Ala Leu Arg Ile His
                100                 105                 110

Asn Val Thr Ala Ser Asp Ser Gly Lys Tyr Leu Cys Tyr Phe Gln Asp
            115                 120                 125
```

```
Gly Asp Phe Tyr Glu Lys Ala Leu Val Glu Leu Lys Val Ala Ala Leu
    130                 135                 140

Gly Ser Asn Leu His Val Glu Val Lys Gly Tyr Glu Asp Gly Gly Ile
145                 150                 155                 160

His Leu Glu Cys Arg Ser Thr Gly Trp Tyr Pro Gln Pro Gln Ile Gln
                165                 170                 175

Trp Ser Asn Ala Lys Gly Glu Asn Ile Pro Ala Val Glu Ala Pro Val
                180                 185                 190

Val Ala Asp Gly Val Gly Leu Tyr Glu Val Ala Ala Ser Val Ile Met
            195                 200                 205

Arg Gly Gly Ser Gly Glu Gly Val Ser Cys Ile Ile Arg Asn Ser Leu
    210                 215                 220

Leu Gly Leu Glu Lys Thr Ala Ser Ile Ser Ile Ala Asp Pro Phe Phe
225                 230                 235                 240

Arg Ser Ala Gln Pro Trp Ile Ala Ala Leu Ala Gly Thr Leu Pro Ile
                245                 250                 255

Leu Leu Leu Leu Leu Ala Gly Ala Ser Tyr Phe Leu Trp Arg Gln Gln
                260                 265                 270

Lys Glu Ile Thr Ala Leu Ser Ser Glu Ile Glu Ser Glu Gln Glu Met
    275                 280                 285

Lys Glu Met Gly Tyr Ala Ala Thr Glu Arg Glu Ile Ser Leu Arg Glu
    290                 295                 300

Ser Leu Gln Glu Glu Leu Lys Arg Lys Lys Ile Gln Tyr Leu Thr Arg
305                 310                 315                 320

Gly Glu Glu Ser Leu Ser Asp Thr Asn Lys Ser Ala Leu Met Leu Lys
                325                 330                 335

Trp Lys Lys Ala Leu Phe Lys Pro Gly Glu Glu Met Leu Gln Met Arg
                340                 345                 350

Leu His Leu Val Lys
                355

<210> SEQ ID NO 15
<211> LENGTH: 731
<212> TYPE: PRT
<213> ORGANISM: Homo sapiens
<220> FEATURE:
<221> NAME/KEY: VARIANT
<222> LOCATION: (1)...(731)
<223> OTHER INFORMATION: Xaa = Any Amino Acid

<400> SEQUENCE: 15

Met Ala Ser Ser Leu Ala Phe Leu Leu Leu Asn Phe His Val Ser Leu
1               5                   10                  15

Phe Leu Val Gln Leu Leu Thr Pro Cys Ser Ala Gln Phe Ser Val Leu
                20                  25                  30

Gly Pro Ser Gly Pro Ile Leu Ala Met Val Gly Glu Asp Ala Asp Leu
            35                  40                  45

Pro Cys His Leu Phe Pro Thr Met Ser Ala Glu Thr Met Glu Leu Arg
    50                  55                  60

Trp Val Ser Ser Leu Arg Gln Val Val Asn Val Tyr Ala Asp Gly
65                  70                  75                  80

Lys Glu Val Glu Tyr Arg Gln Ser Ala Pro Tyr Arg Gly Arg Thr Ser
                85                  90                  95

Ile Leu Arg Asp Gly Ile Thr Ala Gly Lys Ala Ala Leu Arg Ile His
            100                 105                 110
```

-continued

```
Asn Val Thr Ala Ser Asp Ser Gly Lys Tyr Leu Cys Tyr Phe Gln His
        115                 120                 125

Gly Asp Phe Tyr Glu Lys Ala Pro Val Glu Leu Lys Val Ala Ala Leu
        130                 135                 140

Gly Ser Asp Leu His Ile Glu Val Lys Gly Tyr Asp Asp Gly Gly Ile
145                 150                 155                 160

His Leu Glu Cys Arg Ser Thr Gly Trp Tyr Pro Gln Pro Gln Ile Asn
                165                 170                 175

Trp Ser Asp Ser Lys Gly Glu Asn Ile Pro Ala Val Glu Gly Pro Val
            180                 185                 190

Asn Val Tyr Gly Val Gly Leu Tyr Ala Val Pro Pro Val Ile Met
        195                 200                 205

Thr Gly Thr Ser Gly Gly Val Ser Cys Ile Ile Thr Asn Ser Leu
        210                 215                 220

Leu Gly Leu Glu Lys Thr Ala Ser Ile Ser Ile Ala Asp Pro Phe Ile
225                 230                 235                 240

Gln Gly Gly Ala Pro Ala Arg Xaa Xaa Xaa Gly Pro Gly Xaa Gly Thr
                245                 250                 255

Leu Ala Tyr Phe Xaa Val Ala Xaa Ser Trp Gln Gly Ala Ser Tyr Phe
                260                 265                 270

Leu Trp Arg Gln Gln Lys Glu Xaa Ile Gly Leu Ser Arg Glu Thr Glu
        275                 280                 285

Arg Glu Arg Glu Met Lys Glu Met Gly Tyr Xaa Ala Thr Glu Gln Glu
        290                 295                 300

Ile Ser Ala Lys Arg Ser Leu Gln Glu Glu Leu Lys Trp Arg Lys Ile
305                 310                 315                 320

Gln Tyr Met Ala Arg Gly Glu Glu Ser Ser Asp Thr Lys Lys Ser
                325                 330                 335

Ala Leu Met Leu Lys Trp Lys Lys Ala Leu Phe Lys Pro Gly Asp Lys
                340                 345                 350

Met Leu Gln Met Arg Val Ser Pro Cys Lys Ile Asn Trp Met Tyr Ser
            355                 360                 365

Lys Ile Tyr Cys Arg Lys Gly Glu Leu Ile Lys Phe Ile Ser Gly Arg
        370                 375                 380

Val Lys Ile Glu Asn Lys Pro Leu Ser Ile Lys His Gln Trp Ala Xaa
385                 390                 395                 400

Ser Met Trp Gly Gly Lys Gln Gln Lys Cys Xaa Lys Arg Ile Leu Val
                405                 410                 415

Ala Ser Trp Gly Arg Ile Arg Val Leu Gly Lys Ala Xaa Thr Asp Leu
            420                 425                 430

Thr Phe Ile Ser Pro Leu Val Thr Arg Pro Leu Gly Leu Ser Pro Met
        435                 440                 445

Thr Leu Met Arg Glu Ser His Ser Gly Gln Ala Arg Asp Thr Gly Phe
        450                 455                 460

Trp Lys Asp Leu Leu Ser Met Ala Gln Ala Leu His Ala Val Ala Leu
465                 470                 475                 480

Lys Ser Arg Lys Asn Gly Arg Pro His Gly His Leu Leu Lys Leu Ser
                485                 490                 495

Ala Ala Asp Val Ile Leu Tyr Pro Asp Met Ala Asn Ala Ile Leu Leu
            500                 505                 510

Val Ser Glu Asp Gln Arg Ser Val Gln Arg Ala Glu Glu Pro His Asp
        515                 520                 525

Leu Pro Asp Asn Pro Glu Arg Phe Glu Trp Arg Tyr Cys Val Leu Gly
```

```
                530             535             540
Cys Glu Ser Phe Met Ser Glu Arg His Tyr Trp Glu Val Glu Val Gly
545                 550                 555                 560

Asp Arg Lys Glu Trp His Ile Gly Val Cys Ser Lys Asn Val Glu Arg
                565                 570                 575

Lys Lys Val Trp Val Lys Met Thr Pro Glu Asn Gly Tyr Trp Thr Met
            580                 585                 590

Gly Leu Thr Asp Gly Asn Lys Tyr Arg Ala Leu Thr Glu Pro Arg Thr
        595                 600                 605

Asn Leu Lys Leu Pro Glu Pro Pro Arg Lys Val Gly Val Ile Leu Asp
    610                 615                 620

Tyr Glu Thr Gly His Ile Ser Phe Tyr Asn Ala Thr Asp Gly Ser His
625                 630                 635                 640

Ile Tyr Thr Phe Leu His Ala Ser Ser Glu Pro Leu Tyr Pro Val
                645                 650                 655

Phe Arg Ile Leu Thr Leu Glu Pro Thr Ala Leu Thr Val Cys Pro Ile
                660                 665                 670

Pro Lys Val Glu Ser Ser Pro Asp Pro Asp Leu Val Pro Asp His Ser
            675                 680                 685

Leu Glu Ile Pro Leu Thr Pro Gly Leu Ala Asn Glu Ser Gly Glu Pro
690                 695                 700

Gln Ala Glu Val Thr Ser Leu Leu Pro Ala Gln Pro Gly Ala Lys
705                 710                 715                 720

Gly Leu Thr Leu His Asn Ser Gln Ser Glu Pro
                725                 730

<210> SEQ ID NO 16
<211> LENGTH: 584
<212> TYPE: PRT
<213> ORGANISM: Homo sapiens

<400> SEQUENCE: 16

Met Lys Met Ala Ser Ser Leu Ala Phe Leu Leu Leu Asn Phe His Val
 1               5                  10                  15

Ser Leu Phe Leu Val Gln Leu Leu Thr Pro Cys Ser Ala Gln Phe Ser
            20                  25                  30

Val Leu Gly Pro Ser Gly Pro Ile Leu Ala Met Val Gly Glu Asp Ala
        35                  40                  45

Asp Leu Pro Cys His Leu Phe Pro Thr Met Ser Ala Glu Thr Met Glu
    50                  55                  60

Leu Arg Trp Val Ser Ser Ser Leu Arg Gln Val Val Asn Val Tyr Ala
65                  70                  75                  80

Asp Gly Lys Glu Val Glu Asp Arg Gln Ser Ala Pro Tyr Arg Gly Arg
                85                  90                  95

Thr Ser Ile Leu Arg Asp Gly Ile Thr Ala Gly Lys Ala Ala Leu Arg
            100                 105                 110

Ile His Asn Val Thr Ala Ser Asp Ser Gly Lys Tyr Leu Cys Tyr Phe
        115                 120                 125

Gln Asp Gly Asp Phe Tyr Glu Lys Ala Leu Val Glu Leu Lys Val Ala
    130                 135                 140

Ala Leu Gly Ser Asp Leu His Ile Glu Val Lys Gly Tyr Glu Asp Gly
145                 150                 155                 160

Gly Ile His Leu Glu Cys Arg Ser Thr Gly Trp Tyr Pro Gln Pro Gln
                165                 170                 175
```

```
Ile Lys Trp Ser Asp Thr Lys Gly Glu Asn Ile Pro Ala Val Glu Ala
            180                 185                 190

Pro Val Ala Asp Gly Val Gly Leu Tyr Ala Val Ala Ala Ser Val
        195                 200                 205

Ile Met Arg Gly Ser Ser Gly Gly Val Ser Cys Ile Ile Arg Asn
        210                 215                 220

Ser Leu Leu Gly Leu Glu Lys Thr Ala Ser Ile Ser Ile Ala Asp Pro
225                 230                 235                 240

Phe Phe Arg Ser Ala Gln Pro Trp Ile Ala Ala Leu Ala Gly Thr Leu
                245                 250                 255

Pro Ile Ser Leu Leu Leu Ala Gly Ala Ser Tyr Phe Leu Trp Arg
            260                 265                 270

Gln Gln Lys Glu Lys Ile Ala Leu Ser Arg Glu Thr Glu Arg Glu Arg
            275                 280                 285

Glu Met Lys Glu Met Gly Tyr Ala Ala Thr Glu Gln Glu Ile Ser Leu
            290                 295                 300

Arg Glu Lys Leu Gln Glu Leu Lys Trp Arg Lys Ile Gln Tyr Met
305                 310                 315                 320

Ala Arg Gly Glu Lys Ser Leu Ala Tyr His Glu Trp Lys Met Ala Leu
                325                 330                 335

Phe Lys Pro Ala Asp Val Ile Leu Asp Pro Thr Ala Asn Ala Ile
            340                 345                 350

Leu Leu Val Ser Glu Asp Gln Arg Ser Val Gln Arg Ala Glu Glu Pro
            355                 360                 365

Arg Asp Leu Pro Asp Asn Pro Glu Arg Phe Glu Trp Arg Tyr Cys Val
370                 375                 380

Leu Gly Cys Glu Asn Phe Thr Ser Gly Arg His Tyr Trp Glu Val Glu
385                 390                 395                 400

Val Gly Asp Arg Lys Glu Trp His Ile Gly Val Cys Ser Lys Asn Val
                405                 410                 415

Glu Arg Lys Lys Gly Trp Val Lys Met Thr Pro Glu Asn Gly Tyr Trp
            420                 425                 430

Thr Met Gly Leu Thr Asp Gly Asn Lys Tyr Arg Ala Leu Thr Glu Pro
            435                 440                 445

Arg Thr Asn Leu Lys Leu Pro Glu Pro Pro Arg Lys Val Gly Ile Phe
450                 455                 460

Leu Asp Tyr Glu Thr Gly Glu Ile Ser Phe Tyr Asn Ala Thr Asp Gly
465                 470                 475                 480

Ser His Ile Tyr Thr Phe Pro His Ala Ser Phe Ser Glu Pro Leu Tyr
                485                 490                 495

Pro Val Phe Arg Ile Leu Thr Leu Glu Pro Thr Ala Leu Thr Ile Cys
            500                 505                 510

Pro Ile Pro Lys Glu Val Glu Ser Ser Pro Asp Pro Asp Leu Val Pro
            515                 520                 525

Asp His Ser Leu Glu Thr Pro Leu Thr Pro Gly Leu Ala Asn Glu Ser
530                 535                 540

Gly Glu Pro Gln Ala Glu Val Thr Ser Leu Leu Leu Pro Ala His Pro
545                 550                 555                 560

Gly Ala Glu Val Ser Pro Ser Ala Thr Thr Asn Gln Asn His Lys Leu
                565                 570                 575

Gln Ala Arg Thr Glu Ala Leu Tyr
            580
```

-continued

```
<210> SEQ ID NO 17
<211> LENGTH: 350
<212> TYPE: PRT
<213> ORGANISM: Homo sapiens

<400> SEQUENCE: 17

Met Ala Ser Phe Leu Ala Phe Leu Leu Leu Asn Phe Arg Val Cys Leu
 1               5                  10                  15

Leu Leu Leu Gln Leu Leu Met Pro His Ser Ala Gln Phe Ser Val Leu
            20                  25                  30

Gly Pro Ser Gly Pro Ile Leu Ala Met Val Gly Glu Asp Ala Asp Leu
        35                  40                  45

Pro Cys His Leu Phe Pro Thr Met Ser Ala Glu Thr Met Glu Leu Lys
    50                  55                  60

Trp Val Ser Ser Leu Arg Gln Val Val Asn Val Tyr Ala Asp Gly
65                  70                  75                  80

Lys Glu Val Glu Asp Arg Gln Ser Ala Pro Tyr Arg Gly Arg Thr Ser
                85                  90                  95

Ile Leu Arg Asp Gly Ile Thr Ala Gly Lys Ala Ala Phe Arg Ile His
            100                 105                 110

Asn Val Thr Gly Ser Asp Arg Trp Lys Tyr Leu Cys Tyr Phe Gln Asp
        115                 120                 125

Gly Asp Phe Tyr Glu Lys Ala Leu Val Glu Leu Lys Val Ala Ala Leu
    130                 135                 140

Gly Ser Asp Leu His Val Asp Val Lys Gly Tyr Lys Asp Gly Gly Ile
145                 150                 155                 160

His Leu Glu Cys Arg Ser Thr Gly Trp Tyr Pro Gln Pro Gln Ile Gln
                165                 170                 175

Trp Ser Asn Asn Lys Gly Glu Asn Ile Pro Thr Val Glu Ala Pro Val
            180                 185                 190

Val Ala Asp Gly Val Gly Leu Tyr Ala Val Ala Ala Ser Val Ile Met
        195                 200                 205

Arg Gly Ser Ser Gly Glu Gly Val Ser Cys Thr Ile Arg Asn Ser Leu
    210                 215                 220

Leu Gly Leu Glu Lys Thr Ala Ser Ile Ser Ile Ala Arg Pro Phe Phe
225                 230                 235                 240

Arg Ser Ala Gln Arg Trp Ile Ala Ala Leu Ala Gly Thr Leu Pro Val
                245                 250                 255

Leu Leu Leu Leu Leu Gly Gly Ala Gly Tyr Phe Leu Trp Gln Gln Gln
            260                 265                 270

Glu Glu Lys Lys Thr Gln Phe Arg Lys Lys Arg Glu Gln Glu Leu
        275                 280                 285

Arg Glu Met Ala Trp Ser Thr Met Lys Gln Glu Gln Ser Thr Arg Val
    290                 295                 300

Lys Leu Leu Glu Glu Leu Arg Trp Arg Ser Ile Gln Tyr Ala Ser Arg
305                 310                 315                 320

Gly Glu Arg His Ser Ala Tyr Asn Glu Trp Lys Lys Ala Leu Phe Lys
                325                 330                 335

Pro Gly Glu Glu Met Leu Gln Met Arg Leu His Phe Val Lys
            340                 345                 350

<210> SEQ ID NO 18
<211> LENGTH: 513
<212> TYPE: PRT
<213> ORGANISM: Homo sapiens
```

-continued

```
<400> SEQUENCE: 18

Met Lys Met Ala Ser Phe Leu Ala Phe Leu Leu Asn Phe Arg Val
  1               5                  10                  15

Cys Leu Leu Leu Leu Gln Leu Leu Met Pro His Ser Ala Gln Phe Ser
             20                  25                  30

Val Leu Gly Pro Ser Gly Pro Ile Leu Ala Met Val Gly Glu Asp Ala
             35                  40                  45

Asp Leu Pro Cys His Leu Phe Pro Thr Met Ser Ala Glu Thr Met Glu
 50                  55                  60

Leu Lys Trp Val Ser Ser Leu Arg Gln Val Val Asn Val Tyr Ala
 65                  70                  75                  80

Asp Gly Lys Glu Val Glu Asp Arg Gln Ser Ala Pro Tyr Arg Gly Arg
                 85                  90                  95

Thr Ser Ile Leu Arg Asp Gly Ile Thr Ala Gly Lys Ala Ala Leu Arg
                100                 105                 110

Ile His Asn Val Thr Ala Ser Asp Ser Gly Lys Tyr Leu Cys Tyr Phe
            115                 120                 125

Gln Asp Gly Asp Phe Tyr Glu Lys Ala Leu Val Glu Leu Lys Val Ala
130                 135                 140

Ala Leu Gly Ser Asp Leu His Val Asp Val Lys Gly Tyr Lys Asp Gly
145                 150                 155                 160

Gly Ile His Leu Glu Cys Arg Ser Thr Gly Trp Tyr Pro Gln Pro Gln
                165                 170                 175

Ile Gln Trp Ser Asn Asn Lys Gly Glu Asn Ile Pro Thr Val Glu Ala
                180                 185                 190

Pro Val Val Ala Asp Gly Val Gly Leu Tyr Ala Val Ala Ala Ser Val
            195                 200                 205

Ile Met Arg Gly Ser Ser Gly Glu Gly Val Ser Cys Thr Ile Arg Ser
210                 215                 220

Ser Leu Leu Gly Leu Glu Lys Thr Ala Ser Ile Ser Ile Ala Asp Pro
225                 230                 235                 240

Phe Phe Arg Ser Ala Gln Arg Trp Ile Ala Ala Leu Ala Arg Thr Leu
                245                 250                 255

Pro Val Leu Leu Leu Leu Leu Gly Gly Ala Gly Tyr Phe Leu Trp Gln
            260                 265                 270

Gln Gln Glu Glu Lys Lys Thr Gln Phe Arg Lys Lys Arg Glu Gln
                275                 280                 285

Glu Leu Arg Glu Met Ala Trp Ser Thr Met Lys Gln Glu Gln Ser Thr
290                 295                 300

Arg Val Lys Leu Leu Glu Glu Leu Arg Trp Arg Ser Ile Gln Tyr Ala
305                 310                 315                 320

Ser Arg Gly Glu Arg His Ser Ala Tyr Asn Glu Trp Lys Lys Ala Leu
                325                 330                 335

Phe Lys Pro Ala Asp Val Ile Leu Asp Pro Lys Thr Ala Asn Pro Ile
            340                 345                 350

Leu Leu Val Ser Glu Asp Gln Arg Ser Val Gln Arg Ala Lys Glu Pro
            355                 360                 365

Gln Asp Leu Pro Asp Asn Pro Glu Arg Phe Asn Trp His Tyr Cys Val
370                 375                 380

Leu Gly Cys Glu Ser Phe Ile Ser Gly Arg His Tyr Trp Glu Val Glu
385                 390                 395                 400

Val Gly Asp Arg Lys Glu Trp His Ile Gly Val Cys Ser Lys Asn Val
                405                 410                 415
```

```
Gln Arg Lys Gly Trp Val Lys Met Thr Pro Glu Asn Gly Phe Trp Thr
                420                 425                 430
Met Gly Leu Thr Asp Gly Asn Lys Tyr Arg Thr Leu Thr Glu Pro Arg
            435                 440                 445
Thr Asn Leu Lys Leu Pro Lys Pro Pro Lys Lys Val Gly Val Phe Leu
        450                 455                 460
Asp Tyr Glu Thr Gly Asp Ile Ser Phe Tyr Asn Ala Val Asp Gly Ser
465                 470                 475                 480
His Ile His Thr Phe Leu Asp Val Ser Phe Ser Glu Ala Leu Tyr Pro
                485                 490                 495
Val Phe Arg Ile Leu Thr Leu Glu Pro Thr Ala Leu Ser Ile Cys Pro
            500                 505                 510
Ala

<210> SEQ ID NO 19
<211> LENGTH: 290
<212> TYPE: PRT
<213> ORGANISM: Homo sapiens

<400> SEQUENCE: 19

Met Ala Ser Phe Leu Ala Phe Leu Leu Asn Phe Arg Val Cys Leu
1               5                   10                  15
Leu Leu Leu Gln Leu Leu Met Pro His Ser Ala Gln Phe Ser Val Leu
                20                  25                  30
Gly Pro Ser Gly Pro Ile Leu Ala Met Val Gly Glu Asp Ala Asp Leu
            35                  40                  45
Pro Cys His Leu Phe Pro Thr Met Ser Ala Glu Thr Met Glu Leu Lys
        50                  55                  60
Trp Val Ser Ser Ser Leu Arg Gln Val Val Asn Val Tyr Ala Asp Gly
65                  70                  75                  80
Lys Glu Val Glu Asp Arg Gln Ser Ala Pro Tyr Arg Gly Arg Thr Ser
                85                  90                  95
Ile Leu Arg Asp Gly Ile Thr Ala Gly Lys Ala Ala Phe Arg Ile His
                100                 105                 110
Asn Val Thr Gly Ser Asp Arg Trp Lys Tyr Leu Cys Tyr Phe Gln Asp
            115                 120                 125
Gly Asp Phe Tyr Glu Lys Ala Leu Val Glu Leu Lys Val Ala Ala Leu
130                 135                 140
Gly Ser Asp Leu His Val Asp Val Lys Gly Tyr Lys Asp Gly Gly Ile
145                 150                 155                 160
His Leu Glu Cys Arg Ser Thr Gly Trp Tyr Pro Gln Pro Gln Ile Gln
                165                 170                 175
Trp Ser Asn Asn Lys Gly Glu Asn Ile Pro Thr Val Glu Ala Pro Val
            180                 185                 190
Val Ala Asp Gly Val Gly Leu Tyr Ala Val Ala Ser Val Ile Met
        195                 200                 205
Arg Gly Ser Ser Gly Glu Gly Val Ser Cys Thr Ile Arg Asn Ser Leu
        210                 215                 220
Leu Gly Leu Glu Lys Thr Ala Ser Ile Ser Ile Ala Arg Pro Phe Phe
225                 230                 235                 240
Arg Ser Ala Gln Arg Trp Ile Ala Ala Leu Ala Gly Thr Leu Pro Val
                245                 250                 255
Leu Leu Leu Leu Leu Gly Gly Ala Gly Tyr Phe Leu Trp Gln Gln Gln
            260                 265                 270
```

Glu Lys Lys Thr Gln Phe Arg Lys Lys Lys Arg Glu Gln Glu Leu
275              280                285

Arg Glu
    290

<210> SEQ ID NO 20
<211> LENGTH: 819
<212> TYPE: DNA
<213> ORGANISM: Homo sapiens

<400> SEQUENCE: 20

| | | | | | |
|---|---|---|---|---|---|
| atgatcttcc | tcctgctaat | gttgagcctg | gaattgcagc | ttcaccagat | agcagcttta | 60 |
| ttcacagtga | cagtccctaa | ggaactgtac | ataatagagc | atggcagcaa | tgtgaccctg | 120 |
| gaatgcaact | ttgacactgg | aagtcatgtg | aaccttggag | caataacagc | cagtttgcaa | 180 |
| aaggtggaaa | atgatacatc | cccacaccgt | gaaagagcca | ctttgctgga | ggagcagctg | 240 |
| cccctaggga | aggcctcgtt | ccacatacct | caagtccaag | tgagggacga | aggacagtac | 300 |
| caatgcataa | tcatctatgg | ggtcgcctgg | gactacaagt | acctgactct | gaaagtcaaa | 360 |
| gcttcctaca | ggaaaataaa | cactcacatc | ctaaaggttc | cagaaacaga | tgaggtagag | 420 |
| ctcacctgcc | aggctacagg | ttatcctctg | gcagaagtat | cctggccaaa | cgtcagcgtt | 480 |
| cctgccaaca | ccagccactc | caggacccct | gaaggcctct | accaggtcac | cagtgttctg | 540 |
| cgcctaaagc | cacccctgg | cagaaacttc | agctgtgtgt | tctggaatac | tcacgtgagg | 600 |
| gaacttactt | tggccagcat | tgaccttcaa | agtcagatgg | aacccaggac | ccatccaact | 660 |
| tggctgcttc | acattttcat | cccctcctgc | atcattgctt | tcattttcat | agccacagtg | 720 |
| atagccctaa | gaaacaact | ctgtcaaaag | ctgtattctt | caaagacac | aacaaaaaga | 780 |
| cctgtcacca | acaaagag | ggaagtgaac | agtgctatc | | | 819 |

<210> SEQ ID NO 21
<211> LENGTH: 549
<212> TYPE: DNA
<213> ORGANISM: Homo sapiens

<400> SEQUENCE: 21

| | | | | | |
|---|---|---|---|---|---|
| atgatcttcc | tcctgctaat | gttgagcctg | gaattgcagc | ttcaccagat | agcagcttta | 60 |
| ttcacagtga | cagtccctaa | ggaactgtac | ataatagagc | atggcagcaa | tgtgaccctg | 120 |
| gaatgcaact | ttgacactgg | aagtcatgtg | aaccttggag | caataacagc | cagtttgcaa | 180 |
| aaggtggaaa | atgatacatc | cccacaccgt | gaaagagcca | ctttgctgga | ggagcagctg | 240 |
| cccctaggga | aggcctcgtt | ccacatacct | caagtccaag | tgagggacga | aggacagtac | 300 |
| caatgcataa | tcatctatgg | ggtcgcctgg | gactacaagt | acctgactct | gaaagtcaaa | 360 |
| ggtcagatgg | aacccaggac | ccatccaact | tggctgcttc | acattttcat | cccctcctgc | 420 |
| atcattgctt | tcattttcat | agccacagtg | atagccctaa | gaaacaact | ctgtcaaaag | 480 |
| ctgtattctt | caaagacac | aacaaaaaga | cctgtcacca | acaaagag | ggaagtgaac | 540 |
| agtgctatc | | | | | | 549 |

<210> SEQ ID NO 22
<211> LENGTH: 873
<212> TYPE: DNA
<213> ORGANISM: Homo sapiens

<400> SEQUENCE: 22

-continued

```
atgaggatat tgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca agcgaattac tgtgaaagtc aatgccccat acaacaaaat caaccaaaga     420
attttggttg tggatccagt cacctctgaa catgaactga catgtcaggc tgagggctac     480
cccaaggccg aagtcatctg acaagcagt gaccatcaag tcctgagtgg taagaccacc      540
accaccaatt ccaagagaga ggagaagctt ttcaatgtga ccagcacact gagaatcaac     600
acaacaacta atgagatttt ctactgcact tttaggagat tagatcctga ggaaaaccat     660
acagctgaat tggtcatccc agaactacct ctggcacatc ctccaaatga aggactcac      720 ttggtaattc tgggagccat cttattatgc cttggtgtag cactgacatt catcttccgt     780
ttaagaaaag ggagaatgat ggatgtgaaa aaatgtggca tccaagatac aaactcaaag     840
aagcaaagtg atacacattt ggaggagacg taa                                 873
```

<210> SEQ ID NO 23
<211> LENGTH: 951
<212> TYPE: DNA
<213> ORGANISM: Homo sapiens

<400> SEQUENCE: 23

```
atgctgcgtc ggcggggcag ccctggcatg ggtgtgcatg tgggtgcagc cctgggagca      60
ctgtggttct gcctcacagg agccctggag gtccaggtcc ctgaagaccc agtggtggca     120
ctggtgggca ccgatgccac cctgtgctgc tccttctccc ctgagcctgg cttcagcctg     180
gcacagctca acctcatctg cagctgaca gacaccaaac agctggtgca cagctttgct      240
gagggccagg accagggcag cgcctatgcc aaccgcacgg ccctcttccc ggacctgctg     300
gcacagggca atgcatccct gaggctgcag cgcgtgcgtg tggcggacga gggcagcttc     360
acctgcttcg tgagcatccg ggatttcggc agcgctgccg tcagcctgca ggtggccgct     420
ccctactcga agcccagcat gaccctggag cccaacaagg acctgcggcc aggggacacg     480
gtgaccatca cgtgctccag ctaccagggc taccctgagg ctgaggtgtt ctggcaggat     540
gggcagggtg tgcccctgac tggcaacgtg accacgtcgc agatggccaa cgagcagggc     600
ttgtttgatg tgcacagcgt cctgcggtg gtgctgggtg caaatggcac ctacagctgc      660
ctggtgcgca accccgtgct gcagcaggat gcgcacggct ctgtcaccat cacagggcag     720
cctatgacat tcccccccaga ggccctgtgg gtgaccgtgg ggctgtctgt ctgtctcatt     780
gcactgctgg tggccctggc tttcgtgtgc tggagaaaga tcaaacagag ctgtgaggag     840
gagaatgcag gagctgagga ccaggatggg gaggagaag ctccaagac agccctgcag       900 cctctgaaac actctgacag caaagaagat gatggacaag aaatagcctg a              951
```

<210> SEQ ID NO 24
<211> LENGTH: 316
<212> TYPE: PRT
<213> ORGANISM: Homo sapiens

<400> SEQUENCE: 24

Met Leu Arg Arg Arg Gly Ser Pro Gly Met Gly Val His Val Gly Ala

```
            1               5                   10                  15
Ala Leu Gly Ala Leu Trp Phe Cys Leu Thr Gly Ala Leu Glu Val Gln
                    20                  25                  30

Val Pro Glu Asp Pro Val Ala Leu Val Gly Thr Asp Ala Thr Leu
            35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
                100                 105                 110

Arg Val Ala Asp Glu Gly Ser Phe Thr Cys Phe Val Ser Ile Arg Asp
                115                 120                 125

Phe Gly Ser Ala Ala Val Ser Leu Gln Val Ala Ala Pro Tyr Ser Lys
                130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
                180                 185                 190

Ser Gln Met Ala Asn Glu Gln Gly Leu Phe Asp Val His Ser Val Leu
                195                 200                 205

Arg Val Val Leu Gly Ala Asn Gly Thr Tyr Ser Cys Leu Val Arg Asn
210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
                260                 265                 270

Lys Ile Lys Gln Ser Cys Glu Glu Glu Asn Ala Gly Ala Glu Asp Gln
                275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315

<210> SEQ ID NO 25
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 25
ctcgaggaat tcgccgccat gatcttcctc ctgctaat                              38

<210> SEQ ID NO 26
<211> LENGTH: 34
<212> TYPE: DNA
<213> ORGANISM: Artificial Sequence
<220> FEATURE:
<223> OTHER INFORMATION: Oligonucleotide primer
<221> NAME/KEY: misc_feature
```

<222> LOCATION: (0)...(0)
<223> OTHER INFORMATION: This sequence is listed from 3' to 5'.

<400> SEQUENCE: 26
gggaagtgaa cagtgctatc gcggccgcaa aaaa         34

<210> SEQ ID NO 27
<211> LENGTH: 948
<212> TYPE: DNA
<213> ORGANISM: Mus

<400> SEQUENCE: 27

| | | | | | |
|---|---|---|---|---|---|
| atgcttcgag | gatggggtgg | ccccagtgtg | ggtgtgtgtg | tgcgcacagc | gctgggggtg | 60 |
| ctgtgcctct | gcctcacagg | agctgtggaa | gtccaggtct | ctgaagaccc | cgtggtggcc | 120 |
| ctggtggaca | cggatgccac | cctacgctgc | tccttttccc | cagagcctgg | cttcagtctg | 180 |
| gcacagctca | acctcatctg | gcagctgaca | gacaccaaac | agctggtgca | cagcttcacg | 240 |
| gagggccggg | accaaggcag | tgcctactcc | aaccgcacag | cgctcttccc | tgacctgttg | 300 |
| gtgcaaggca | atgcgtcctt | gaggctgcag | cgcgtccgag | taaccgacga | gggcagctac | 360 |
| acctgctttg | tgagcattca | ggactttgac | agcgctgctg | ttagcctgca | ggtggccgcc | 420 |
| ccctactcga | agcccagcat | gaccctggag | cccaacaagg | acctacgtcc | aggaacatg | 480 |
| gtgaccatca | cgtgctctag | ctaccagggc | tatccggagg | ccgaggtgtt | ctggaaggat | 540 |
| ggacagggag | tgcccttgac | tggcaatgtg | acatcccaga | tggccaacga | gcggggcttg | 600 |
| ttcgatgttc | acagcgtgct | gagggtggtg | ctgggtgcta | acggcaccta | cagctgcctg | 660 |
| gtacgcaacc | cggtgttgca | gcaagatgct | cacggctcag | tcaccatcac | agggcagccc | 720 |
| ctgacattcc | cccctgaggc | tctgtgggta | accgtggggc | tctctgtctg | tcttgtggta | 780 |
| ctactggtgg | ccctggcttt | cgtgtgctgg | agaaagatca | agcagagctg | cgaggaggag | 840 |
| aatgcaggtg | ccaaggacca | ggatggagat | ggagaaggat | ccaagacagc | tctacggcct | 900 |
| ctgaaaccct | ctgaaaacaa | agaagatgac | ggacaagaaa | ttgcttga | | 948 |

<210> SEQ ID NO 28
<211> LENGTH: 315
<212> TYPE: PRT
<213> ORGANISM: Mus

<400> SEQUENCE: 28

Met Leu Arg Gly Trp Gly Gly Pro Ser Val Gly Val Cys Val Arg Thr
1               5                   10                  15

Ala Leu Gly Val Leu Cys Leu Cys Leu Thr Gly Ala Val Glu Val Gln
            20                  25                  30

Val Ser Glu Asp Pro Val Val Ala Leu Val Asp Thr Asp Ala Thr Leu
        35                  40                  45

Arg Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Thr
65                  70                  75                  80

Glu Gly Arg Asp Gln Gly Ser Ala Tyr Ser Asn Arg Thr Ala Leu Phe
                85                  90                  95

Pro Asp Leu Leu Val Gln Gly Asn Ala Ser Leu Arg Leu Gln Arg Val
            100                 105                 110

Arg Val Thr Asp Glu Gly Ser Tyr Thr Cys Phe Val Ser Ile Gln Asp
        115                 120                 125

```
Phe Asp Ser Ala Ala Val Ser Leu Gln Val Ala Ala Pro Tyr Ser Lys
        130                 135                 140

Pro Ser Met Thr Leu Glu Pro Asn Lys Asp Leu Arg Pro Gly Asn Met
145                 150                 155                 160

Val Thr Ile Thr Cys Ser Ser Tyr Gln Gly Tyr Pro Glu Ala Glu Val
                165                 170                 175

Phe Trp Lys Asp Gly Gln Gly Val Pro Leu Thr Gly Asn Val Thr Ser
            180                 185                 190

Gln Met Ala Asn Glu Arg Gly Leu Phe Asp Val His Ser Val Leu Arg
        195                 200                 205

Val Val Leu Gly Ala Asn Gly Thr Tyr Ser Cys Leu Val Arg Asn Pro
    210                 215                 220

Val Leu Gln Gln Asp Ala His Gly Ser Val Thr Ile Thr Gly Gln Pro
225                 230                 235                 240

Leu Thr Phe Pro Pro Glu Ala Leu Trp Val Thr Val Gly Leu Ser Val
                245                 250                 255

Cys Leu Val Val Leu Leu Val Ala Leu Ala Phe Val Cys Trp Arg Lys
            260                 265                 270

Ile Lys Gln Ser Cys Glu Glu Asn Ala Gly Ala Lys Asp Gln Asp
        275                 280                 285

Gly Asp Gly Glu Gly Ser Lys Thr Ala Leu Arg Pro Leu Lys Pro Ser
    290                 295                 300

Glu Asn Lys Glu Asp Asp Gly Gln Glu Ile Ala
305                 310                 315

<210> SEQ ID NO 29
<211> LENGTH: 322
<212> TYPE: PRT
<213> ORGANISM: Mus

<400> SEQUENCE: 29

Met Gln Leu Lys Cys Pro Cys Phe Val Ser Leu Gly Thr Arg Gln Pro
  1               5                  10                  15

Val Trp Lys Lys Leu His Val Ser Ser Gly Phe Ser Gly Leu Gly
            20                  25                  30

Leu Phe Leu Leu Leu Leu Ser Ser Leu Cys Ala Ala Ser Ala Glu Thr
            35                  40                  45

Glu Val Gly Ala Met Val Gly Ser Asn Val Val Leu Ser Cys Ile Asp
 50                  55                  60

Pro His Arg Arg His Phe Asn Leu Ser Gly Leu Tyr Val Tyr Trp Gln
 65                  70                  75                  80

Ile Glu Asn Pro Glu Val Ser Val Thr Tyr Tyr Leu Pro Tyr Lys Ser
                85                  90                  95

Pro Gly Ile Asn Val Asp Ser Ser Tyr Lys Asn Arg Gly His Leu Ser
            100                 105                 110

Leu Asp Ser Met Lys Gln Gly Asn Phe Ser Leu Tyr Leu Lys Asn Val
            115                 120                 125

Thr Pro Gln Asp Thr Gln Glu Phe Thr Cys Arg Val Phe Met Asn Thr
        130                 135                 140

Ala Thr Glu Leu Val Lys Ile Leu Glu Glu Val Val Arg Leu Arg Val
145                 150                 155                 160

Ala Ala Asn Phe Ser Thr Pro Val Ile Ser Thr Ser Asp Ser Ser Asn
                165                 170                 175

Pro Gly Gln Glu Arg Thr Tyr Thr Cys Met Ser Lys Asn Gly Tyr Pro
            180                 185                 190
```

```
Glu Pro Asn Leu Tyr Trp Ile Asn Thr Thr Asp Asn Ser Leu Ile Asp
        195                 200                 205

Thr Ala Leu Gln Asn Asn Thr Val Tyr Leu Asn Lys Leu Gly Leu Tyr
        210                 215                 220

Asp Val Ile Ser Thr Leu Arg Leu Pro Trp Thr Ser Arg Gly Asp Val
225                 230                 235                 240

Leu Cys Cys Val Glu Asn Val Ala Leu His Gln Asn Ile Thr Ser Ile
                245                 250                 255

Ser Gln Ala Glu Ser Phe Thr Gly Asn Asn Thr Lys Asn Pro Gln Glu
                260                 265                 270

Thr His Asn Asn Glu Leu Lys Val Leu Val Pro Val Leu Ala Val Leu
            275                 280                 285

Ala Ala Ala Ala Phe Val Ser Phe Ile Ile Tyr Arg Arg Thr Arg Pro
    290                 295                 300

His Arg Ser Tyr Thr Gly Pro Lys Thr Val Gln Leu Glu Leu Thr Asp
305                 310                 315                 320

His Ala
```

What is claimed is:

1. An isolated nucleic acid molecule selected from the group consisting of:
   a) a nucleic acid comprising the nucleotide sequence of SEQ ID NO:1;
   b) a nucleic acid comprising the nucleotide sequence of SEQ ID NO:3;
   c) a nucleic acid comprising the cDNA insert of the plasmid deposited with ATCC as Accession Number 2085,
   d) a nucleic acid molecule which encodes a polypeptide comprising the amino acid sequence of SEQ ID NO:4;
   e) a nucleic acid molecule which encodes a polypeptide comprising the amino acid sequence encoded by the cDNA insert of the plasmid deposited with ATCC as Accession Number 2085.

2. The nucleic acid molecule of claim 1 further comprising vector nucleic acid sequences.

3. The nucleic acid molecule of claim 1 further comprising nucleic acid sequences encoding a heterologous polypeptide.

4. A host cell which contains the nucleic acid molecule of claim 1.

5. The host cell of claim 4 which is a mammalian host cell.

6. A nonhuman mammalian host cell containing the nucleic acid molecule of claim 1.

7. An isolated nucleic acid molecule comprising the nucleotide sequence set forth in SEQ ID NO:1, or the complement thereof.

8. The nucleic acid molecule of claim 7 further comprising vector nucleic acid sequences.

9. The nucleic acid molecule of claim 7 further comprising nucleic acid sequences encoding a heterologous polypeptide.

10. A host cell which contains the nucleic acid molecule of claim 7.

11. The host cell of claim 10 which is a mammalian host cell.

12. A nonhuman mammalian host cell containing the nucleic acid molecule of claim 7.

13. An isolated nucleic acid molecule comprising the nucleotide sequence set forth in SEQ ID NO:3, or the complement thereof.

14. The nucleic acid molecule of claim 13 further comprising vector nucleic acid sequences.

15. The nucleic acid molecule of claim 13 further comprising nucleic acid sequences encoding a heterologous polypeptide.

16. A host cell which contains the nucleic acid molecule of claim 13.

17. The host cell of claim 16 which is a mammalian host cell.

18. A nonhuman mammalian host cell containing the nucleic acid molecule of claim 13.

19. An isolated nucleic acid molecule comprising the nucleotide sequence set forth in the cDNA insert of the plasmid deposited with ATCC as Accession Number 2084, or the complement thereof.

20. The nucleic acid molecule of claim 19 further comprising vector nucleic acid sequences.

21. The nucleic acid molecule of claim 19 further comprising nucleic acid sequences encoding a heterologous polypeptide.

22. A host cell which contains the nucleic acid molecule of claim 19.

23. The host cell of claim 22 which is a mammalian host cell.

24. A nonhuman mammalian host cell containing the nucleic acid molecule of claim 19.

25. An isolated nucleic acid molecule comprising the nucleotide sequence set forth in the cDNA insert of the plasmid deposited with ATCC as Accession Number 2085, or the complement thereof.

26. The nucleic acid molecule of claim 25 further comprising vector nucleic acid sequences.

27. The nucleic acid molecule of claim 25 further comprising nucleic acid sequences encoding a heterologous polypeptide.

28. A host cell which contains the nucleic acid molecule of claim 25.

29. The host cell of claim 28 which is a mammalian host cell.

30. A nonhuman mammalian host cell containing the nucleic acid molecule of claim 25.

31. An isolated nucleic acid molecule which encodes a polypeptide comprising the amino acid sequence of SEQ ID NO:4, or the complement thereof.

32. The nucleic acid molecule of claim 31 further comprising vector nucleic acid sequences.

33. The nucleic acid molecule of claim 31 further comprising nucleic acid sequences encoding a heterologous polypeptide.

34. A host cell which contains the nucleic acid molecule of claim 31.

35. The host cell of claim 34 which is a mammalian host cell.

36. A nonhuman mammalian host cell containing the nucleic acid molecule of claim 31.

37. A kit comprising a nucleic acid molecule of claim 1 and instructions for use.

38. A kit comprising the nucleic acid molecule of claim 7 and instructions for use.

39. A kit comprising the nucleic acid molecule of claim 13 and instructions for use.

40. A kit comprising the nucleic acid molecule of claim 19 and instructions for use.

41. A kit comprising the nucleic acid molecule of claim 25 and instructions for use.

42. A kit comprising the nucleic acid molecule of claim 31 and instructions for use.

43. A method for producing a polypeptide selected from the group consisting of:
   a) a polypeptide comprising the amino acid sequence of SEQ ID NO:4; and
   b) a polypeptide comprising the amino acid sequence encoded by the cDNA insert of the plasmid deposited with ATCC as Accession Number 2085; the method comprising culturing the host cell of claim 4 under conditions in which the nucleic acid molecule is expressed.

44. A method for producing a polypeptide comprising the amino acid sequence of SEQ ID NO:2, the method comprising culturing the host cell of claim 10 under conditions in which the nucleic acid molecule is expressed.

45. A method for producing a polypeptide comprising the amino acid sequence encoded by the cDNA insert of the plasmid deposited with ATCC as Accession Number 2084, the method comprising culturing the host cell of claim 10 or claim 22 under conditions in which the nucleic acid molecule is expressed.

46. A method for producing a polypeptide comprising the amino acid sequence of SEQ ID NO:4, the method comprising culturing the host cell of claim 16 or claim 34 under conditions in which the nucleic acid molecule is expressed.

47. A method for producing a polypeptide comprising the amino acid sequence encoded by the cDNA insert of the plasmid deposited with ATCC as Accession Number 2085, the method comprising culturing the host cell of claim 16 or claim 28 under conditions in which the nucleic acid molecule is expressed.

* * * * *